(12) United States Patent
Meyers et al.

(10) Patent No.: US 6,897,056 B2
(45) Date of Patent: May 24, 2005

(54) 32544, A NOVEL HUMAN PHOSPHOLIPASE C AND USES THEREOF

(75) Inventors: Rachel Meyers, Newton, MA (US); Immaculada Silos-Santiago, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 181 days.

(21) Appl. No.: 09/927,112

(22) Filed: Aug. 10, 2001

(65) Prior Publication Data

US 2002/0106774 A1 Aug. 8, 2002

Related U.S. Application Data

(60) Provisional application No. 60/246,808, filed on Nov. 8, 2000.

(51) Int. Cl.[7] .............................. C12N 9/20; C12N 1/20; C12N 15/00; C12P 21/04; C07H 21/04
(52) U.S. Cl. ................. 435/198; 435/320.1; 435/252.3; 435/71.1; 536/23.2; 536/23.4; 530/350
(58) Field of Search ............................... 435/198, 252.3, 435/320.1, 71.1; 536/23.2, 23.4; 530/350

(56) References Cited

FOREIGN PATENT DOCUMENTS

| WO | WO 01/85956 A2 | 11/2001 |
|---|---|---|
| WO | WO 02/04490 A2 | 1/2002 |
| WO | WO 02/16597 A2 | 2/2002 |
| WO | WO 02/063005 A2 | 8/2002 |

OTHER PUBLICATIONS

Database EMBL Online! Aug. 13, 1998, retrieved from EBI Database Accession No. AB007919, XP002220767.
Seki, N., et al., "Characterization of cDNA Clones in Size–Fractionated cDNA Libraries from Human Brain", *DNA Research*, vol. 4, Sep. 19, 1997, pp: 345–349, XP000870411 *whole document*.
Database EMBL Online! May 1, 2000, retrieved from EBI Database Accession No. Q9UPT3, XP002220768.
Reiko, K., et al., Prediction of the Coding Sequences of Unidentified Human Genes. XIV. The Complete Sequences of 100 new cDNA Clones from Brain Which Code for Large Proteins in vitro, *DNA Research*, vol. 6, May 31, 1999, pp: 197–205, XP000852618 *whole document*.

*Primary Examiner*—Ponnathapu Achutamurthy
*Assistant Examiner*—Yong D. Pak
(74) *Attorney, Agent, or Firm*—Millennium Pharmaceuticals, Inc.

(57) ABSTRACT

The invention provides isolated nucleic acids molecules, designated 32544 nucleic acid molecules, which encode novel phospholipase family members. The invention also provides antisense nucleic acid molecules, recombinant expression vectors containing 32544 nucleic acid molecules, host cells into which the expression vectors have been introduced, and nonhuman transgenic animals in which a 32544 gene has been introduced or disrupted. The invention still further provides isolated 32544 proteins, fusion proteins, antigenic peptides and anti-32544 antibodies. Diagnostic methods utilizing compositions of the invention are also provided.

15 Claims, 8 Drawing Sheets

```
TCGCGATCTAGAACTAGTGGCACGGCTCCTGCACTCCCACTGCCGCAGGAACTGCTCAGGAACCTGCCGGTCTCCGGCT        SEQ ID NO:1
GGGACGGTGGCTGGATCAGCTCAAGCCTCCAGGGCCCTGAGGCTGAGGGGCTGAGTGCTCATTCCAGCCGCCTCGGGGA
ACCCGGGCTGGGAGACCCCATGCCTGGGGGTGAGCCTGGAGCCAGGGCAGTGCGGTGAGAGGCTCCGGAGAGAGGGCTG
GGCACCACCAGGCTTGGGTGTGTGATGCGCTGCTGGCCCAGGCTACACCCCGACAAGGGACACCGGGGGCCCTGGGAGC
AGAGAGACCTCAGAGCAGCCTCCTCCTGCCTCCTGTGGACGGCCGGCCCCAGCTGGTGATCCCAGCCAGTCCCAGCTTT
                                                M   A   P   P   T   A   G   P   L   P      10 SEQ ID NO:2
CAGTTGCTGCCCCCACCGACAGTCCTCAGTCCCTCCATG ATG GCT CCC CCG ACA GCC GGC CCC CTT CCT           30
                                        ↑SEQ ID NO:3→
  G   P   A   L   P   P   E   D   P   G   P   D   P   E   S   R   W   L   F   L           30
GGC CCA GCT CTT CCG CCT GAG GAC CCA GGG CCG GAT CCG GAG AGC AGG TGG CTT TTC TTG           90

S   A   N   I   L   P   V   V   E   R   C   M   G   A   M   Q   E   G   M   Q           50
AGC GCC AAC ATT CTG CCC GTG GTG GAG CGG TGC ATG GGT GCC ATG CAA GAG GGG ATG CAG          150

M   V   K   L   R   G   G   S   K   G   L   V   R   F   Y   Y   L   D   E   H           70
ATG GTG AAG CTG CGT GGC GGC TCC AAG GGC CTG GTC CGC TTC TAC TAC CTG GAC GAG CAC          210

R   S   C   I   R   W   R   P   S   R   K   N   E   K   A   K   I   S   I   D           90
CGC TCC TGC ATC CGC TGG AGG CCC TCA CGC AAG AAC GAG AAG GCC AAG ATC TCC ATC GAC          270

S   I   Q   E   V   S   E   G   R   Q   S   E   V   F   Q   R   Y   P   D   G          110
TCC ATC CAG GAG GTG AGT GAG GGG CGG CAG TCG GAG GTC TTC CAG CGC TAC CCT GAC GGC          330

S   F   D   P   N   C   C   F   S   I   Y   H   G   S   H   R   E   S   L   D          130
AGC TTC GAC CCC AAC TGC TGC TTC AGC ATC TAC CAC GGC AGC CAC CGC GAG TCG CTG GAC          390

L   V   S   T   S   S   E   V   A   R   T   W   V   T   G   L   R   Y   L   M          150
CTG GTC TCC ACC AGC AGC GAG GTG GCG CGC ACC TGG GTC ACT GGC CTG CGC TAC CTC ATG          450

A   G   I   S   D   E   D   S   L   A   R   R   Q   R   T   R   D   Q   W   L          170
GCC GGC ATC AGC GAC GAG GAC AGC CTG GCT CGC CGC CAG CGC ACC AGG GAC CAG TGG CTG          510

K   Q   T   F   D   E   A   D   K   N   G   D   G   S   L   S   I   G   E   V          190
AAG CAG ACG TTT GAC GAG GCC GAC AAG AAC GGG GAT GGC AGC CTG AGC ATT GGC GAG GTC          570

L   Q   L   L   H   K   L   N   V   N   L   P   R   Q   R   V   K   Q   M   F          210
CTG CAG CTG CTG CAC AAG CTC AAC GTG AAC CTG CCC CGG CAG AGG GTG AAG CAG ATG TTC          630

R   E   A   D   T   D   D   H   Q   G   T   L   G   F   E   E   F   C   A   F          230
AGG GAA GCG GAC ACG GAT GAC CAC CAA GGG ACG CTG GGT TTT GAA GAG TTC TGT GCC TTC          690

Y   K   M   M   S   T   R   R   D   L   Y   L   L   M   L   T   Y   S   N   H          250
TAC AAG ATG ATG TCC ACC CGC CGG GAC CTC TAC CTG CTC ATG CTG ACC TAC AGC AAC CAC          750

K   D   H   L   D   A   A   S   L   Q   R   F   L   Q   V   E   Q   K   M   A          270
AAG GAC CAC CTG GAT GCC GCC AGC CTG CAG CGC TTC CTG CAG GTG GAG CAG AAG ATG GCG          810

G   V   T   L   E   S   C   Q   D   I   I   E   Q   F   E   P   C   P   E   N          290
GGT GTG ACC CTC GAG AGC TGC CAG GAC ATC ATC GAG CAG TTT GAG CCA TGC CCA GAA AAC          870

K   S   K   G   L   L   G   I   D   G   F   T   N   Y   T   R   S   P   A   G          310
AAG AGT AAG GGG CTG CTG GGC ATT GAT GGC TTC ACC AAC TAC ACC AGG AGC CCT GCT GGT          930

D   I   F   N   P   E   H   H   H   V   H   Q   D   M   T   Q   P   L   S   H          330
GAC ATC TTC AAC CCT GAG CAC CAC CAT GTG CAC CAG GAC ATG ACG CAG CCG CTG AGC CAC          990

Y   F   I   T   S   S   H   N   T   Y   L   V   G   D   Q   L   M   S   Q   S          350
TAC TTC ATC ACC TCG TCC CAC AAC ACC TAC CTC GTG GGT GAC CAG CTC ATG TCC CAG TCA         1050

R   V   D   M   Y   A   W   V   L   Q   A   G   C   R   C   V   E   V   D   C          370
CGG GTG GAC ATG TAT GCT TGG GTC CTG CAG GCT GGC TGC CGC TGC GTG GAG GTG GAC TGC         1110

W   D   G   P   D   G   E   P   I   V   H   H   G   Y   T   L   T   S   K   I          390
TGG GAT GGG CCC GAC GGG GAG CCC ATT GTG CAC CAT GGC TAC ACT CTG ACT TCC AAG ATC         1170
```

FIGURE 1a

```
L   F   K   D   V   I   E   T   I   N   K   Y   A   F   I   K   N   E   Y   P    410
CTC TTC AAA GAC GTC ATT GAA ACC ATC AAC AAA TAT GCC TTC ATC AAG AAT GAG TAC CCA 1230

V   I   L   S   I   E   N   H   C   S   V   I   Q   Q   K   K   M   A   Q   Y    430
GTG ATC CTG TCC ATC GAA AAC CAC TGC AGT GTC ATC CAG CAG AAG AAA ATG GCC CAG TAT 1290

L   T   D   I   L   G   D   K   L   D   L   S   S   V   S   S   E   D   A   T    450
CTG ACT GAC ATC CTT GGG GAC AAG CTG GAC CTG TCA TCA GTG AGC AGT GAA GAT GCC ACC 1350

T   L   P   S   P   Q   M   L   K   G   K   I   L   V   K   G   K   K   L   P    470
ACA CTC CCC TCT CCA CAG ATG CTC AAG GGC AAG ATC CTC GTG AAG GGG AAG AAG CTC CCA 1410

A   N   I   S   E   D   A   E   G   E   V   S   D   E   D   S   A   D   E        490
GCC AAC ATC AGC GAG GAT GCG GAG GAA GGC GAG GTG TCT GAT GAG GAC AGT GCT GAT GAG 1470

I   D   D   D   C   K   L   L   N   G   D   A   S   T   N   R   K   R   V   E    510
ATT GAC GAT GAC TGC AAG CTC CTC AAT GGG GAT GCA TCC ACC AAT CGA AAG CGT GTA GAA 1530

N   T   A   K   R   K   L   D   S   L   I   K   E   S   K   I   R   D   C   E    530
AAC ACT GCT AAG AGG AAA CTG GAT TCC CTC ATC AAA GAG TCG AAG ATT CGG GAC TGT GAG 1590

D   P   N   N   F   S   V   S   T   L   S   P   S   G   K   L   G   R   K   S    550
GAC CCC AAC AAC TTC TCC GTC TCC ACA CTG TCC CCA TCT GGA AAG CTC GGA CGC AAG AGC 1650

K   A   E   E   D   V   E   S   G   E   D   A   G   A   S   R   R   N   G   R    570
AAG GCT GAA GAG GAC GTG GAG TCT GGG GAG GAT GCC GGG GCC AGC AGA CGC AAT GGC CGC 1710

L   V   V   G   S   F   S   R   R   K   K   K   G   S   K   L   K   K   A   A    590
CTC GTC GTG GGA AGC TTC TCC AGG CGC AAG AAG AAG GGC AGC AAG CTG AAG AAG GCG GCC 1770

S   V   E   E   G   D   E   G   Q   D   S   P   G   G   Q   S   R   G   A   T    610
AGC GTG GAG GAG GGA GAT GAG GGT CAG GAC TCC CCG GGA GGC CAG AGC CGA GGG GCG ACC 1830

R   Q   K   K   T   M   K   L   S   R   A   L   S   D   L   V   K   Y   T   K    630
CGG CAG AAG AAG ACC ATG AAG CTG TCC CGG GCC CTC TCT GAC CTG GTG AAG TAC ACC AAG 1890

S   V   A   T   H   D   I   E   M   E   A   A   S   S   W   Q   V   S   S   F    650
TCC GTG GCC ACC CAC GAC ATA GAG ATG GAG GCG GCG TCC AGC TGG CAG GTG TCG TCC TTC 1950

S   E   T   K   A   H   Q   I   L   Q   Q   K   P   A   Q   Y   L   R   F   N    670
AGC GAG ACC AAG GCC CAC CAG ATT CTG CAG CAG AAG CCG GCG CAG TAC CTA CGC TTC AAC 2010

Q   Q   Q   L   S   R   I   Y   P   S   S   Y   R   V   D   S   S   N   Y   N    690
CAG CAG CAG CTC TCC CGC ATC TAC CCC TCC TCC TAC CGT GTG GAC TCC AGC AAC TAC AAC 2070

P   Q   P   F   W   N   A   G   C   Q   M   V   A   L   N   Y   Q   S   E   G    710
CCG CAG CCC TTC TGG AAC GCC GGC TGC CAA ATG GTT GCC CTG AAC TAC CAG TCA GAG GGG 2130

R   M   L   Q   L   N   R   A   K   F   S   A   N   G   G   C   G   Y   V   L    730
CGG ATG CTG CAG CTG AAC CGA GCC AAG TTC AGC GCC AAC GGT GGC TGC GGC TAC GTA CTC 2190

K   P   G   C   M   C   Q   G   V   F   N   P   N   S   E   D   P   L   P   G    750
AAG CCT GGG TGC ATG TGC CAG GGC GTG TTC AAC CCC AAC TCG GAG GAC CCC CTG CCC GGG 2250

Q   L   K   K   Q   L   V   L   R   I   I   S   G   Q   Q   L   P   K   P   R    770
CAG CTC AAG AAG CAG CTG GTG CTC CGG ATC ATC AGT GGC CAG CAG CTT CCC AAG CCG CGC 2310

D   S   M   L   G   D   R   G   E   I   I   D   P   F   V   E   V   E   I   I    790
GAC TCC ATG CTG GGG GAC CGT GGG GAG ATC ATC GAC CCC TTT GTG GAG GTG GAG ATC ATT 2370

G   L   P   V   D   C   S   R   E   Q   T   R   V   V   D   D   N   G   F   N    810
GGG CTC CCT GTG GAC TGC AGC AGG GAG CAG ACC CGC GTG GTG GAC GAC AAC GGG TTC AAC 2430

P   T   W   E   E   T   L   V   F   M   V   H   M   P   E   I   A   L   V   R    830
CCC ACC TGG GAG GAG ACC CTG GTT TTC ATG GTG CAC ATG CCG GAG ATC GCG CTG GTC CGC 2490

F   L   V   W   D   H   D   P   I   G   R   D   F   I   G   Q   R   T   L   A    850
TTC CTC GTC TGG GAC CAC GAT CCC ATC GGG CGT GAC TTC ATT GGC CAG AGG ACG CTG GCC 2550

F   S   S   M   M   P   G   Y   R   H   V   Y   L   E   G   M   E   E   A   S    870
TTC AGC AGC ATG ATG CCA GGC TAC AGA CAC GTG TAC CTA GAA GGG ATG GAA GAG GCC TCC 2610
```

FIGURE 1b

```
  I   F   V   H   V   A   V   S   D   I   S   G   K   V   K   Q   A   L   G   L    890
 ATC TTC GTG CAT GTG GCT GTC AGT GAC ATC AGC GGT AAG GTC AAG CAG GCT CTG GGC CTA   2670
  K   G   L   F   L   R   G   P   K   P   G   S   L   D   S   H   A   A   G   R    910
 AAA GGC CTC TTC CTC CGA GGC CCA AAG CCC GGC TCG CTG GAC AGT CAT GCT GCT GGG CGG   2730
  P   P   A   R   P   S   V   S   Q   R   I   L   R   R   T   A   S   A   P   T    930
 CCC CCG GCC CGG CCC TCC GTT AGC CAG CGG ATC CTG CGG CGC ACG GCC AGC GCC CCG ACC   2790
  K   S   Q   K   P   G   R   R   G   F   P   E   L   V   L   G   T   R   D   T    950
 AAG AGC CAG AAG CCG GGC CGC AGG GGC TTC CCG GAG CTG GTC CTG GGT ACA CGG GAC ACA   2850
  G   S   K   G   V   A   D   D   V   V   P   P   G   P   G   P   A   P   E   A    970
 GGC TCC AAG GGG GTG GCA GAC GAT GTG GTG CCC CCC GGG CCC GGA CCT GCT CCG GAA GCC   2910
  P   A   Q   E   G   P   G   S   G   S   P   R   G   K   A   P   A   A   V   A    990
 CCA GCC CAG GAG GGG CCC GGC AGC GGC AGC CCC CGA GGT AAG GCG CCA GCT GCG GTG GCA   2970
  E   K   S   P   V   R   V   R   P   P   R   V   L   D   G   P   G   P   A   G   1010
 GAG AAG AGC CCT GTG CGA GTG CGG CCC CCG CGT GTC CTG GAC GGC CCC GGG CCT GCT GGG   3030
  M   A   A   T   C   M   K   C   V   V   G   S   C   A   G   V   N   T   G   G   1030
 ATG GCC GCC ACA TGC ATG AAG TGT GTG GTG GGA TCC TGC GCC GGC GTG AAC ACC GGG GGC   3090
  L   Q   R   E   R   P   P   S   P   G   P   A   S   R   Q   A   A   I   R   Q   1050
 CTG CAG AGG GAG CGG CCA CCC AGC CCG GGG CCT GCA AGC AGG CAG GCA GCC ATT CGC CAG   3150
  Q   P   R   A   R   A   D   S   L   G   A   P   C   C   G   L   D   P   H   A   1070
 CAG CCC CGG GCC CGG GCT GAC TCA CTG GGG GCC CCC TGC TGT GGC CTG GAC CCT CAC GCT   3210
  I   P   G   R   S   R   E   A   P   K   G   P   G   A   W   R   Q   G   P   G   1090
 ATC CCG GGG AGA AGC AGA GAG GCC CCC AAG GGT CCT GGG GCC TGG AGG CAG GGT CCA GGC   3270
  G   S   G   S   M   S   S   D   S   S   S   P   D   S   P   G   I   P   E   R   1110
 GGT AGC GGC TCC ATG TCC TCG GAC TCC AGC AGC CCA GAC AGC CCG GGC ATC CCC GAA AGG   3330
  S   P   R   W   P   E   G   A   C   R   Q   P   G   A   L   Q   G   E   M   S   1130
 TCC CCC CGC TGG CCT GAG GGT GCC TGC AGG CAA CCG GGG GCC CTG CAG GGA GAG ATG AGT   3390
  A   L   F   A   Q   K   L   E   E   I   R   S   K   S   P   M   F   S   A   G   1150
 GCC TTG TTT GCT CAA AAG CTG GAG GAG ATC AGG AGT AAA TCC CCC ATG TTC TCC GCC GGT   3450
  K   P   L   L   P   C   V   V   L   P   H   A   P   G   M   A   G   P   G   S   1170
 AAG CCC CTC TTG CCC TGC GTG GTC CTC CCG CAC GCC CCT GGC ATG GCT GGG CCT GGG TCA   3510
  P   A   A   A   S   A   W   T   V   S   P   R   V   L   V   L   V   A   L   Y   1190
 CCT GCT GCT GCT TCT GCG TGG ACG GTG TCG CCT CGT GTC CTC GTG CTC GTG GCT CTG TAT   3570
  P   W   H   C   L   R   G   T   L   L   P   W   L   A   C   G   P   *           1208
 CCG TGG CAC TGT CTC CGT GGC ACT CTG CTC CCT TGG CTT GCC TGT GGC CCA TAG           3624
                                                                    ←SEQ ID NO:3↑
CCCCAGCCCTCCTGTCTGAGCTTGAGGCCCTGGGACTTGGGTGGAGCTGGTTTGAGGCCCGACAGGCTGGGAAGAACCA

GCTGCTCTTGCTGAGGGTCTGGGGCCGGGACTGTGGCCTGACATGCTGGGCCCCTCCGGCTGGGCGCTTCCCCAAACTC

ACCTCCTGGGCGGCTGGCGACCTGCATGGCCCCTGATGCCTTTCCTGGGACTGGGGGCCATGTACCATCCCATTCCCAC

CTCCCTCTAGGGCAGGCTCCAGGGGTCCCTACTGGGAAGTCTGATGTGGGCAGGTAGTGCAGCTGCTGGGCGTCTCCTG

CGCCCCTGGGACGCCTGGAGCCTGCTGAGTGCTGCGTGGAGTAGATTCCCTGGGCCCCAGGGCTTCGCTGCTTTGGGCT

GAAGCACCCCACTAGAAGGGTGTCTCCTTAGCCTGGAGGGAGGGACATACACGGAGCCCGCCCCACACCACCCTGCCCC

TCCAGACCCCCCTGACCAAGCTTTCCTTTCTGCCCCCACCCACGCTTGCCTCCGTAGTTAGGAACTGAGAGCGGCGAGT

GACAGGTAACGGGGCCCAGCCCCG
```

FIGURE 1c

```
       *->vikeGwLlkks...kswkkRyfvLfn..nvLlyykdskkkpkgsipL  SEQ ID NO:4
          + eG  ++k +++++    R+  L ++++++ +   ++ k+ k +i++
32544  44   AMQEGMQMVKLrggSKGLVRFYYLDEhrSCIRWRPSR-KNEKAKISI  89 sgc.qvek.pd.............kncFeirt.dr..tlllqaeseeer
       +++++V ++   ++    ++ ++++ ++++cF i ++++++l l  +s+e +
32544  90  DSIqEVSEgRQsevfqrypdgsfdpNCCFSIYHgSHreSLDLVSTSSEVA  139 keWvkaiqsair<-*
       ++Wv+ ++++++
32544  140 RTWVTGLRYLMA    151
```

Fig. 3

```
       *->elkeaFkefDkDgDGkIsfeEfkaalkkl<-*  SEQ ID NO:5
          lk+ F+e+Dk+gDG +s+ E +++l+kl
32544  169  WLKQTFDEADKNGDGSLSIGEVLQLLHKL      197
```

Fig. 4a

```
       *->elkeaFkefDk.DgDGkIsfeEfkaalkkl<-*  SEQ ID NO:6
          ++k++F+e+D++D+  G++  feEf+a+ k++
32544  205  RVKQMFREADTdDHQGTLGFEEFCAFYKMM       234
```

Fig. 4b

```
       *->dmsiPLsHYfisSshntYLtgkQlwGkssvesYrqqLdaGcRcvELD  SEQ ID NO:7
          dm +PLsHYfi+SshntYL g+Ql ++s v +Y +L+aGcRcvE D
32544  323   DMTQPLSHYFITSSHNTYLVGDQLMSQSRVDMYAWVLQAGCRCVEVD  369 cwdGkpddepiIyHGhtltleiklkdVleaIkdfafkPtSpyPvIlSlen
       cwdG pd+epi+ HG+tlt++i++kdV+e+I ++af    +yPvIlS+en
32544  370  CWDG-PDGEPIVHHGYTLTSKILFKDVIETINKYAFI-KNEYPVILSIEN  417

HcnsddqQrkmakyfkeiFgdmLltkPtldslttepglpLPslkdlrgKI
       Hc++  qQ+kma+y+ +i+gd+L   + + +t+    LPs+ +l+gKI
32544  418  HCSVI-QQKKMAQYLTDILGDKLDLSSVSSEDATT----LPSPQMLKGKI  462

LLknkk<-*
       L+k+kk
32544  463  LVKGKK    468
```

Fig. 5

```
              *->ElsnLvnYiqsikFrsFelsGeekntsyeisSFsErkvkakkllkes   SEQ ID NO:8
                 ls+Lv Y +s+     ++   e   s ++sSFsE+   ka + l++
32544    621    ALSDLVKYTKSV--ATHDIE-MEAASSWQVSSFSET--KAHQILQQK 662 pvefVkyNkrqLsRvYPkGtRvDSSNfmPqvfWnaGCQmVALNfQTsDlp
              p +  ++N+ qLsR+YP   RvDSSN++Pq+fWnaGCQmVALN+Q+ +
32544    663    PAQYLRFNQQQLSRIYPSSYRVDSSNYNPQPFWNAGCQMVALNYQSEGRM 712 mqiNdGmFeyNggqPdGsfksGYlLKPeflR<-*
              +q+N ++F++Ngg        +GY+LKP ++
32544    713   LQLNRAKFSANGG-------CGYVLKPGCMC        736
```

Fig. 6

```
              *->LtVtvieArnLpkmDk.....vngrlsDPYVkvsllgdkkdlkkfkT  SEQ ID NO:9
                 L+  ++i++++Lpk + +   ++ ++ ++DP+V+v+++g+++d ++ +T
32544    756    LVLRIISGQQLPKPRDsmlgdRGE-IIDPFVEVEIIGLPVDCSREQT 801 kvvkktNGLNPvWneEtFvFekvplpelasktLrfaVyDedrfsrdDfiG
              +vv ++ G+NP+W  Et+vF  v++pe+a   +rf V+D+d ++ DfiG
32544    802   RVVDDN-GFNPTWE-ETLVFM-VHMPEIAL--VRFLVWDHDPIG-RDFIG 845 qvt<-*
              q+t
32544    846   QRT    848
```

Fig. 7

```
Query:   883  KVKQALGLKGLFLRGPKPGSLDSHAAGRPPARPSVSQRILRRTASAPTKSQKPGRRGFPE 942
              +VKQALGLKGLFLRGPKPGSLDSHAAGRPPARPSVSQRILRRTASAPTKSQKPGRRGFPE
Sbjct:   101  QVKQALGLKGLFLRGPKPGSLDSHAAGRPPARPSVSQRILRRTASAPTKSQKPGRRGFPE 160   SEQ ID NO:10

Query:   943  LVLGTRDTGSKXXXXXXXXXXXXXXXXXXXXXXXXXXSGSPRGKAPAAVAEKSPVRVRPPRV 1002
              LVLGTRDTGSK                          SGSPRGKAPAAVAEKSPVRVRPPRV
Sbjct:   161  LVLGTRDTGSKGVADDVVPPGPGPAPEAPAQEGPGSGSPRGKAPAAVAEKSPVRVRPPRV 220

Query:   1003 LDGPGPAGMAATCMKCVVGSCAGVNTGGLQRERPPSPGPASXXXXXXXXXXXXXDSLGAP 1062
              LDGPGPAGMAATCMKCVVGSCAGVNTGGLQRERPPSPGPAS             DSLGAP
Sbjct:   221  LDGPGPAGMAATCMKCVVGSCAGVNTGGLQRERPPSPGPASRQAAIRQQPRARADSLGAP 280

Query:   1063 CCGLDPHAIPGRSREAPKGPGAWRQXXXXXXXXXXXXXXXXXXXIPERSPRWPEGACRQP 1122
              CCGLDPHAIPGRSREAPKGPGAWRQ                   IPERSPRWPEGACRQP
Sbjct:   281  CCGLDPHAIPGRSREAPKGPGAWRQGPGGSGSMSSDSSSPDSPGIPERSPRWPEGACRQP 340

Query:   1123 GALQGEMSALFAQKLEEIRSKSPMFSAGKPLLPCVVLPHXXXXXXXXXXXXXXXWTVSPR 1182
              GALQGEMSALFAQKLEEIRSKSPMFSAGKPLLPCVVLPH                WTVSPR
Sbjct:   341  GALQGEMSALFAQKLEEIRSKSPMFSAGKPLLPCVVLPHAPGMAGPGSPAAASAWTVSPR 400

Query:   1183 VLVLVALYPWHCLRGTLLPWLACGP 1207
              VLVLVALYPWHCLRGTLLPWLACGP
Sbjct:   401  VLVLVALYPWHCLRGTLLPWLACGP 425
```

Fig. 8

```
Query:   307 SPAGDIFNPEHHHVHQDMTQPLSHYFITSSHNTYLVGDQLMS-QSRVDMYAWVLQAGCRC 365
             SP  ++F+PEH  VHQDM QPLSHYFI SSHNTYL G+QL S +S V+MY    L  GCRC
Sbjct:     2 SPDCNVFDPEHKQVHQDMNQPLSHYFINSSHNTYLTGNQLSSGESSVEMYRQALLKGCRC 61   SEQ ID NO:11

Query:   366 VEVDCWDGPDG--EPIVHHGYTLTSKILFKDVIETINKYAFIKNEYPVILSIENHCSVI- 422
             +E+DCWDG DG   EPI+  HG+T+T++I FKD +E I ++AF+ +EYPVILS+ENHC
Sbjct:    62 IELDCWDGKDGDPEPIITHGHTMTTEISFKDCLEAIKEHAFVTSEYPVILSLENHCDSTP 121

Query:   423 -QQKKMAQYLTDILGDKL---DLSSVSSEDATTLPSPQ 456
              QQ KMA+Y  ++ GD L   L   E   LPSP+
Sbjct:   122 QQQAKMAEYCKEVFGDMLFTEPLEESPLEPGKELPSPE 159
```

Fig. 9a

```
Query:   514 KRKLDSLIKESKIRDCEDPNNFSVSTLSPSGKLGRKSKAEEDVESGEDA 562
             KRK+  LIK K+++  +       S   K   ++++EE+ E G DA
Sbjct:   162 KRKI--LIKNKKLKEHSEEKE------SEEKKTDEETESEEEDEMGSDA 202  SEQ ID NO:12
```

Fig. 9b

```
Query:   742 PNSEDPLPGQLKKQLVLR 759
             P  E P P +LK+++++
Sbjct:   151 PGKELPSPEELKRKILIK 168  SEQ ID NO:13
```

Fig. 9c

```
Query:    41 CMGAMQEGMQMVKLRGGSKGLVRFYYLDEHRSCIRWRP---SRKN-EKAKISIDSIQEVS 96
             C+  MQ+G ++ K+R  S     R++ LD+    + W P   S+K+ EK K  I I+E+
Sbjct:    14 CLQFMQKGSELKKVRSNSWKYNRYFTLDDDMQTLWWEPHWFSKKDSEKPKFDISDIKEIR 73   SEQ ID NO:14

Query:    97 EGRQSEVFQRYPDGSF---DP-NCCFSIYHGSH--RESLDLVSTSSEVARTWVTGLRYLM 150
             G+  +E F R    F      +P +CCFSI  G +      ESLDLV+ S++VA  WV+GLRYL+
Sbjct:    74 MGKNTETF-RNNGKEFQIQEPEDCCFSIIFGENYFHESLDLVANSADVANIWVSGLRYLV 132

Query:   151 AGISDEDSLARRQRTRDQWLKQTFDEADKNGDGSLSIGEVLQLLHKLNVNLPRQRVKQMF 210
                +  L  Q   DQWL++  F +AD+N D  +S  E   LL  +NV +  +   +F
Sbjct:   133 DYA--KHMLDNYQEQLDQWLREWFQQADRNKDSRMSFREAQNLLKLMNVQMDEEYAFSIF 190

Query:   211 READ 214
             RE D
Sbjct:   191 RECD 194
```

Fig. 10

```
Query:   174 FDEADKNGDGSLSIGEVLQLLHKLNVNLPRQRVKQMFREAD--TDDHQGT-LGFEEFCAF 230
             FDE D +G+G L     + + LN L   ++   F+E    + + + T +   E F
Sbjct:     2 FDEFDTDGNGHLDEQTAFKCIKHLNPRLKHHKITNKFKEITIKSKEKERTKITKEHFVDL 61   SEQ ID NO:15

Query:   231 YKMMSTRRDLYLLMLTYSNHKDHLDAASLQRFLQVEQKMAGVTLESCQDIIEQFEPCPEN 290
             YK  +  TR ++Y LM+  YS +KD+LD    L   FL+ EQ M  VT ++C DIIEQ+EPC E
Sbjct:    62 YKELGTRPEVYFLMVQYSKNKDYLDCQDLMLFLETEQGMVHVTEDNCLDIIEQYEPCSEG 121

Query:   291 KSKGLLGIDGFTNY 304
              +  G + IDGFT+Y
Sbjct:   122 RENGWMTIDGFTSY 135
```

Fig. 11

```
Query:   851 FSSMMPGYRHVYLEGMEEASIFVHVAVSDISGKVKQALGLKGLFLRGPKPGSLDSHAAGR 910
             FSS++PGYRHVYLEG+ EASIFVH+ +++I GK +Q  GLKGLF + P+  S ++++
Sbjct:     2 FSSLVPGYRHVYLEGLTEASIFVHITINEIYGKNRQLQGLKGLFNKNPRHSSSENNS--H 59   SEQ ID NO:16

Query:   911 PPARPSVSQRILRRTASAPTKSQKPGRRGFPELV 944
              + S+  RILRRTASAP K +K + GF E+V
Sbjct:    60 YVRKRSIGDRILRRTASAPAKGRKKSKMGFQEMV 93
```

Fig. 12

SEQUENCE LISTING

<160> NUMBER OF SEQ ID NOS: 17

<210> SEQ ID NO 1
<211> LENGTH: 4635
<212> TYPE: DNA
<213> ORGANISM: Homo sapiens
<220> FEATURE:

-continued

```
<221> NAME/KEY: CDS
<222> LOCATION: (435)...(4058)

<400> SEQUENCE: 1
tcgcgatcta gaactagtgg cacggctcct gcactccac tgccgcagga actgctcagg      60
aacctgccgg tctccggctg ggacggtggc tggatcagct caagcctcca gggccctgag    120
gctgaggggc tgagtgctca ttccagccgc ctcggggaac ccgggctggg agaccccatg    180
cctgggggtg agcctggagc cagggcagtg cggtgagagg ctccggagag agggctgggc    240 accaccagge ttgggtgtgt gatgcgctgc tggcccaggc tacacccga caagggacac     300 cgggggccct gggagcagag agacctcaga gcagcctcct cctgcctcct gtggacggcc    360
ggccccagct ggtgatccca gccagtccca gctttcagtt gctgccccca ccgacagtcc    420
```

| | | |
|---|---|---|
| tcagtccctc catg atg gct ccc ccg aca gcc ggc ccc ctt cct ggc cca | 470 | |
| Met Ala Pro Pro Thr Ala Gly Pro Leu Pro Gly Pro | | |
| 1              5                   10 | | |
| gct ctt ccg cct gag gac cca ggg ccg gat ccg gag agc agg tgg ctt | 518 | |
| Ala Leu Pro Pro Glu Asp Pro Gly Pro Asp Pro Glu Ser Arg Trp Leu | | |
| 15                  20                  25 | | |
| ttc ttg agc gcc aac att ctg ccc gtg gtg gag cgg tgc atg ggt gcc | 566 | |
| Phe Leu Ser Ala Asn Ile Leu Pro Val Val Glu Arg Cys Met Gly Ala | | |
| 30              35                  40 | | |
| atg caa gag ggg atg cag atg gtg aag ctg cgt ggc ggc tcc aag ggc | 614 | |
| Met Gln Glu Gly Met Gln Met Val Lys Leu Arg Gly Gly Ser Lys Gly | | |
| 45              50                  55                  60 | | |
| ctg gtc cgc ttc tac tac ctg gac gag cac cgc tcc tgc atc cgc tgg | 662 | |
| Leu Val Arg Phe Tyr Tyr Leu Asp Glu His Arg Ser Cys Ile Arg Trp | | |
| 65                  70                  75 | | |
| agg ccc tca cgc aag aac gag aag gcc aag atc tcc atc gac tcc atc | 710 | |
| Arg Pro Ser Arg Lys Asn Glu Lys Ala Lys Ile Ser Ile Asp Ser Ile | | |
| 80              85                  90 | | |
| cag gag gtg agt gag ggg cgg cag tcg gag gtc ttc cag cgc tac cct | 758 | |
| Gln Glu Val Ser Glu Gly Arg Gln Ser Glu Val Phe Gln Arg Tyr Pro | | |
| 95                  100                 105 | | |
| gac ggc agc ttc gac ccc aac tgc tgc ttc agc atc tac cac ggc agc | 806 | |
| Asp Gly Ser Phe Asp Pro Asn Cys Cys Phe Ser Ile Tyr His Gly Ser | | |
| 110             115                 120 | | |
| cac cgc gag tcg ctg gac ctg gtc tcc acc agc agc gag gtg gcg cgc | 854 | |
| His Arg Glu Ser Leu Asp Leu Val Ser Thr Ser Ser Glu Val Ala Arg | | |
| 125                 130                 135                 140 | | |
| acc tgg gtc act ggc ctg cgc tac ctc atg gcc ggc atc agc gac gag | 902 | |
| Thr Trp Val Thr Gly Leu Arg Tyr Leu Met Ala Gly Ile Ser Asp Glu | | |
| 145                 150                 155 | | |
| gac agc ctg gct cgc cgc cag cgc acc agg gac cag tgg ctg aag cag | 950 | |
| Asp Ser Leu Ala Arg Arg Gln Arg Thr Arg Asp Gln Trp Leu Lys Gln | | |
| 160                 165                 170 | | |
| acg ttt gac gag gcc gac aag aac ggg gat ggc agc ctg agc att ggc | 998 | |
| Thr Phe Asp Glu Ala Asp Lys Asn Gly Asp Gly Ser Leu Ser Ile Gly | | |
| 175                 180                 185 | | |
| gag gtc ctg cag ctg ctg cac aag ctc aac gtg aac ctg ccc cgg cag | 1046 | |
| Glu Val Leu Gln Leu Leu His Lys Leu Asn Val Asn Leu Pro Arg Gln | | |
| 190                 195                 200 | | |
| agg gtg aag cag atg ttc agg gaa gcg gac acg gat gac cac caa ggg | 1094 | |
| Arg Val Lys Gln Met Phe Arg Glu Ala Asp Thr Asp Asp His Gln Gly | | |
| 205                 210                 215                 220 | | |
| acg ctg ggt ttt gaa gag ttc tgt gcc ttc tac aag atg atg tcc acc | 1142 | |
| Thr Leu Gly Phe Glu Glu Phe Cys Ala Phe Tyr Lys Met Met Ser Thr | | |
| 225                 230                 235 | | |

-continued

```
cgc cgg gac ctc tac ctg ctc atg ctg acc tac agc aac cac aag gac      1190
Arg Arg Asp Leu Tyr Leu Leu Met Leu Thr Tyr Ser Asn His Lys Asp
        240                 245                 250 cac ctg gat gcc gcc agc ctg cag cgc ttc ctg cag gtg gag cag aag      1238
His Leu Asp Ala Ala Ser Leu Gln Arg Phe Leu Gln Val Glu Gln Lys
    255                 260                 265 atg gcg ggt gtg acc ctc gag agc tgc cag gac atc atc gag cag ttt      1286
Met Ala Gly Val Thr Leu Glu Ser Cys Gln Asp Ile Ile Glu Gln Phe
270                 275                 280 gag cca tgc cca gaa aac aag agt aag ggg ctg ctg ggc att gat ggc      1334
Glu Pro Cys Pro Glu Asn Lys Ser Lys Gly Leu Leu Gly Ile Asp Gly
285                 290                 295                 300 ttc acc aac tac acc agg agc cct gct ggt gac atc ttc aac cct gag      1382
Phe Thr Asn Tyr Thr Arg Ser Pro Ala Gly Asp Ile Phe Asn Pro Glu
                305                 310                 315 cac cac cat gtg cac cag gac atg acg cag ccg ctg agc cac tac ttc      1430
His His His Val His Gln Asp Met Thr Gln Pro Leu Ser His Tyr Phe
        320                 325                 330 atc acc tcg tcc cac aac acc tac ctc gtg ggt gac cag ctc atg tcc      1478
Ile Thr Ser Ser His Asn Thr Tyr Leu Val Gly Asp Gln Leu Met Ser
    335                 340                 345 cag tca cgg gtg gac atg tat gct tgg gtc ctg cag gct ggc tgc cgc      1526
Gln Ser Arg Val Asp Met Tyr Ala Trp Val Leu Gln Ala Gly Cys Arg
350                 355                 360 tgc gtg gag gtg gac tgc tgg gat ggg ccc gac ggg gag ccc att gtg      1574
Cys Val Glu Val Asp Cys Trp Asp Gly Pro Asp Gly Glu Pro Ile Val
365                 370                 375                 380 cac cat ggc tac act ctg act tcc aag atc ctc ttc aaa gac gtc att      1622
His His Gly Tyr Thr Leu Thr Ser Lys Ile Leu Phe Lys Asp Val Ile
                385                 390                 395 gaa acc atc aac aaa tat gcc ttc atc aag aat gag tac cca gtg atc      1670
Glu Thr Ile Asn Lys Tyr Ala Phe Ile Lys Asn Glu Tyr Pro Val Ile
        400                 405                 410 ctg tcc atc gaa aac cac tgc agt gtc atc cag cag aag aaa atg gcc      1718
Leu Ser Ile Glu Asn His Cys Ser Val Ile Gln Gln Lys Lys Met Ala
    415                 420                 425 cag tat ctg act gac atc ctt ggg gac aag ctg gac ctg tca tca gtg      1766
Gln Tyr Leu Thr Asp Ile Leu Gly Asp Lys Leu Asp Leu Ser Ser Val
430                 435                 440 agc agt gaa gat gcc acc aca ctc ccc tct cca cag atg ctc aag ggc      1814
Ser Ser Glu Asp Ala Thr Thr Leu Pro Ser Pro Gln Met Leu Lys Gly
445                 450                 455                 460 aag atc ctc gtg aag ggg aag aag ctc cca gcc aac atc agc gag gat      1862
Lys Ile Leu Val Lys Gly Lys Lys Leu Pro Ala Asn Ile Ser Glu Asp
                465                 470                 475 gcg gag gaa ggc gag gtg tct gat gag gac agt gct gat gag att gac      1910
Ala Glu Glu Gly Glu Val Ser Asp Glu Asp Ser Ala Asp Glu Ile Asp
        480                 485                 490 gat gac tgc aag ctc ctc aat ggg gat gca tcc acc aat cga aag cgt      1958
Asp Asp Cys Lys Leu Leu Asn Gly Asp Ala Ser Thr Asn Arg Lys Arg
    495                 500                 505 gta gaa aac act gct aag agg aaa ctg gat tcc ctc atc aaa gag tcg      2006
Val Glu Asn Thr Ala Lys Arg Lys Leu Asp Ser Leu Ile Lys Glu Ser
510                 515                 520 aag att cgg gac tgt gag gac ccc aac aac ttc tcc gtc tcc aca ctg      2054
Lys Ile Arg Asp Cys Glu Asp Pro Asn Asn Phe Ser Val Ser Thr Leu
525                 530                 535                 540 tcc cca tct gga aag ctc gga cgc aag agc aag gct gaa gag gac gtg      2102
Ser Pro Ser Gly Lys Leu Gly Arg Lys Ser Lys Ala Glu Glu Asp Val
                545                 550                 555
```

-continued

| | |
|---|---|
| gag tct ggg gag gat gcc ggg gcc agc aga cgc aat ggc cgc ctc gtc<br>Glu Ser Gly Glu Asp Ala Gly Ala Ser Arg Arg Asn Gly Arg Leu Val<br>          560                    565                   570 | 2150 |
| gtg gga agc ttc tcc agg cgc aag aag aag ggc agc aag ctg aag aag<br>Val Gly Ser Phe Ser Arg Arg Lys Lys Lys Gly Ser Lys Leu Lys Lys<br>    575                    580                    585 | 2198 |
| gcg gcc agc gtg gag gag gga gat gag ggt cag gac tcc ccg gga ggc<br>Ala Ala Ser Val Glu Glu Gly Asp Glu Gly Gln Asp Ser Pro Gly Gly<br>          590                    595                   600 | 2246 |
| cag agc cga ggg gcg acc cgg cag aag aag acc atg aag ctg tcc cgg<br>Gln Ser Arg Gly Ala Thr Arg Gln Lys Lys Thr Met Lys Leu Ser Arg<br>605                    610                    615                   620 | 2294 |
| gcc ctc tct gac ctg gtg aag tac acc aag tcc gtg gcc acc cac gac<br>Ala Leu Ser Asp Leu Val Lys Tyr Thr Lys Ser Val Ala Thr His Asp<br>                    625                    630                   635 | 2342 |
| ata gag atg gag gcg gcg tcc agc tgg cag gtg tcg tcc ttc agc gag<br>Ile Glu Met Glu Ala Ala Ser Ser Trp Gln Val Ser Ser Phe Ser Glu<br>          640                    645                    650 | 2390 |
| acc aag gcc cac cag att ctg cag cag aag ccg gcg cag tac cta cgc<br>Thr Lys Ala His Gln Ile Leu Gln Gln Lys Pro Ala Gln Tyr Leu Arg<br>                655                    660                   665 | 2438 |
| ttc aac cag cag cag ctc tcc cgc atc tac ccc tcc tcc tac cgt gtg<br>Phe Asn Gln Gln Gln Leu Ser Arg Ile Tyr Pro Ser Ser Tyr Arg Val<br>670                    675                    680 | 2486 |
| gac tcc agc aac tac aac ccg cag ccc ttc tgg aac gcc ggc tgc caa<br>Asp Ser Ser Asn Tyr Asn Pro Gln Pro Phe Trp Asn Ala Gly Cys Gln<br>685                    690                    695                   700 | 2534 |
| atg gtt gcc ctg aac tac cag tca gag ggg cgg atg ctg cag ctg aac<br>Met Val Ala Leu Asn Tyr Gln Ser Glu Gly Arg Met Leu Gln Leu Asn<br>                    705                    710                   715 | 2582 |
| cga gcc aag ttc agc gcc aac ggt ggc tgc ggc tac gta ctc aag cct<br>Arg Ala Lys Phe Ser Ala Asn Gly Gly Cys Gly Tyr Val Leu Lys Pro<br>          720                    725                    730 | 2630 |
| ggg tgc atg tgc cag ggc gtg ttc aac ccc aac tcg gag gac ccc ctg<br>Gly Cys Met Cys Gln Gly Val Phe Asn Pro Asn Ser Glu Asp Pro Leu<br>                735                    740                   745 | 2678 |
| ccc ggg cag ctc aag aag cag ctg gtg ctc cgg atc atc agt ggc cag<br>Pro Gly Gln Leu Lys Lys Gln Leu Val Leu Arg Ile Ile Ser Gly Gln<br>    750                    755                    760 | 2726 |
| cag ctt ccc aag ccg cgc gac tcc atg ctg ggg gac cgt ggg gag atc<br>Gln Leu Pro Lys Pro Arg Asp Ser Met Leu Gly Asp Arg Gly Glu Ile<br>765                    770                    775                   780 | 2774 |
| atc gac ccc ttt gtg gag gtg gag atc att ggg ctc cct gtg gac tgc<br>Ile Asp Pro Phe Val Glu Val Glu Ile Ile Gly Leu Pro Val Asp Cys<br>                    785                    790                   795 | 2822 |
| agc agg gag cag acc cgc gtg gtg gac gac aac ggg ttc aac ccc acc<br>Ser Arg Glu Gln Thr Arg Val Val Asp Asp Asn Gly Phe Asn Pro Thr<br>          800                    805                    810 | 2870 |
| tgg gag gag acc ctg gtt ttc atg gtg cac atg ccg gag atc gcg ctg<br>Trp Glu Glu Thr Leu Val Phe Met Val His Met Pro Glu Ile Ala Leu<br>               815                    820                   825 | 2918 |
| gtc cgc ttc ctc gtc tgg gac cac gat ccc atc ggg cgt gac ttc att<br>Val Arg Phe Leu Val Trp Asp His Asp Pro Ile Gly Arg Asp Phe Ile<br>    830                    835                    840 | 2966 |
| ggc cag agg acg ctg gcc ttc agc agc atg atg cca ggc tac aga cac<br>Gly Gln Arg Thr Leu Ala Phe Ser Ser Met Met Pro Gly Tyr Arg His<br>845                    850                    855                   860 | 3014 |
| gtg tac cta gaa ggg atg gaa gag gcc tcc atc ttc gtg cat gtg gct<br>Val Tyr Leu Glu Gly Met Glu Glu Ala Ser Ile Phe Val His Val Ala | 3062 |

|  |  |
|---|---|
| gtc agt gac atc agc ggt aag gtc aag cag gct ctg ggc cta aaa ggc<br>Val Ser Asp Ile Ser Gly Lys Val Lys Gln Ala Leu Gly Leu Lys Gly<br>880                            885                        890 | 3110 |
| ctc ttc ctc cga ggc cca aag ccc ggc tcg ctg gac agt cat gct gct<br>Leu Phe Leu Arg Gly Pro Lys Pro Gly Ser Leu Asp Ser His Ala Ala<br>         895                        900                        905 | 3158 |
| ggg cgg ccc ccg gcc cgg ccc tcc gtt agc cag cgg atc ctg cgg cgc<br>Gly Arg Pro Pro Ala Arg Pro Ser Val Ser Gln Arg Ile Leu Arg Arg<br>910                          915                        920 | 3206 |
| acg gcc agc gcc ccg acc aag agc cag aag ccg ggc cgc agg ggc ttc<br>Thr Ala Ser Ala Pro Thr Lys Ser Gln Lys Pro Gly Arg Arg Gly Phe<br>925                        930                        935                        940 | 3254 |
| ccg gag ctg gtc ctg ggt aca cgg gac aca ggc tcc aag ggg gtg gca<br>Pro Glu Leu Val Leu Gly Thr Arg Asp Thr Gly Ser Lys Gly Val Ala<br>                   945                        950                        955 | 3302 |
| gac gat gtg gtg ccc ccc ggg ccc gga cct gct ccg gaa gcc cca gcc<br>Asp Asp Val Val Pro Pro Gly Pro Gly Pro Ala Pro Glu Ala Pro Ala<br>960                          965                        970 | 3350 |
| cag gag ggg ccc ggc agc ggc agc ccc cga ggt aag gcg cca gct gcg<br>Gln Glu Gly Pro Gly Ser Gly Ser Pro Arg Gly Lys Ala Pro Ala Ala<br>         975                        980                        985 | 3398 |
| gtg gca gag aag agc cct gtg cga gtg cgg ccc cgt gtc ctg gac<br>Val Ala Glu Lys Ser Pro Val Arg Val Arg Pro Pro Arg Val Leu Asp<br>990                          995                        1000 | 3446 |
| ggc ccc ggg cct gct ggg atg gcc gcc aca tgc atg aag tgt gtg gtg<br>Gly Pro Gly Pro Ala Gly Met Ala Ala Thr Cys Met Lys Cys Val Val<br>1005                       1010                      1015                      1020 | 3494 |
| gga tcc tgc gcc ggc gtg aac acc ggg ggc ctg cag agg gag cgg cca<br>Gly Ser Cys Ala Gly Val Asn Thr Gly Gly Leu Gln Arg Glu Arg Pro<br>                   1025                      1030                      1035 | 3542 |
| ccc agc ccg ggg cct gca agc agg cag gca gcc att cgc cag cag ccc<br>Pro Ser Pro Gly Pro Ala Ser Arg Gln Ala Ala Ile Arg Gln Gln Pro<br>1040                       1045                      1050 | 3590 |
| cgg gcc cgg gct gac tca ctg ggg gcc ccc tgc tgt ggc ctg gac cct<br>Arg Ala Arg Ala Asp Ser Leu Gly Ala Pro Cys Cys Gly Leu Asp Pro<br>                   1055                      1060                      1065 | 3638 |
| cac gct atc ccg ggg aga agc aga gag gcc ccc aag ggt cct ggg gcc<br>His Ala Ile Pro Gly Arg Ser Arg Glu Ala Pro Lys Gly Pro Gly Ala<br>1070                       1075                      1080 | 3686 |
| tgg agg cag ggt cca ggc ggt agc ggc tcc atg tcc tcg gac tcc agc<br>Trp Arg Gln Gly Pro Gly Gly Ser Gly Ser Met Ser Ser Asp Ser Ser<br>1085                       1090                      1095                      1100 | 3734 |
| agc cca gac agc ccg ggc atc ccc gaa agg tcc ccc cgc tgg cct gag<br>Ser Pro Asp Ser Pro Gly Ile Pro Glu Arg Ser Pro Arg Trp Pro Glu<br>                   1105                      1110                      1115 | 3782 |
| ggt gcc tgc agg caa ccg ggg gcc ctg cag gga gag atg agt gcc ttg<br>Gly Ala Cys Arg Gln Pro Gly Ala Leu Gln Gly Glu Met Ser Ala Leu<br>1120                       1125                      1130 | 3830 |
| ttt gct caa aag ctg gag gag atc agg agt aaa tcc ccc atg ttc tcc<br>Phe Ala Gln Lys Leu Glu Glu Ile Arg Ser Lys Ser Pro Met Phe Ser<br>1135                       1140                      1145 | 3878 |
| gcc ggt aag ccc ctc ttg ccc tgc gtg gtc ctc ccg cac gcc cct ggc<br>Ala Gly Lys Pro Leu Leu Pro Cys Val Val Leu Pro His Ala Pro Gly<br>1150                       1155                      1160 | 3926 |
| atg gct ggg cct ggg tca cct gct gct gct tct gcg tgg acg gtg tcg<br>Met Ala Gly Pro Gly Ser Pro Ala Ala Ala Ser Ala Trp Thr Val Ser<br>1165                       1170                      1175                      1180 | 3974 |
| cct cgt gtg ctc gtg ctc gtg gct ctg tat ccg tgg cac tgt ctc cgt | 4022 |

```
                Pro Arg Val Leu Val Leu Val Ala Leu Tyr Pro Trp His Cys Leu Arg
                            1185                1190                1195 ggc act ctg ctc cct tgg ctt gcc tgt ggc cca tag ccccagccct              4068
Gly Thr Leu Leu Pro Trp Leu Ala Cys Gly Pro  *
            1200                1205 cctgtctgag cttgaggccc tgggacttgg gtggagctgg tttgaggccc gacaggctgg       4128
gaagaaccag ctgctcttgc tgagggtctg gggccgggac tgtggcctga catgctgggc       4188
ccctccggct gggcgcttcc ccaaactcac ctcctgggcg gctggcgacc tgcatggccc       4248
ctgatgcctt tcctgggact gggggccatg taccatccca ttcccacctc cctctagggc       4308
aggctccagg ggtccctact gggaagtctg atgtgggcag gtagtgcagc tgctgggcgt       4368
ctcctgcgcc cctgggacgc ctggagcctg ctgagtgctg cgtggagtag attccctggg       4428
ccccagggct tcgctgcttt gggctgaagc accccactag aagggtgtct ccttagcctg       4488
gagggaggga catacacgga gcccgcccca caccaccctg cccctccaga cccccctgac       4548
caagctttcc tttctgcccc cacccacgct tgcctccgta gttaggaact gagagcggcg       4608
agtgacaggt aacggggccc agccccg                                          4635

<210> SEQ ID NO 2
<211> LENGTH: 1207
<212> TYPE: PRT
<213> ORGANISM: Homo sapiens

<400> SEQUENCE: 2

Met Ala Pro Pro Thr Ala Gly Pro Leu Pro Gly Pro Ala Leu Pro Pro
 1               5                  10                  15

Glu Asp Pro Gly Pro Asp Pro Glu Ser Arg Trp Leu Phe Leu Ser Ala
            20                  25                  30

Asn Ile Leu Pro Val Val Glu Arg Cys Met Gly Ala Met Gln Glu Gly
        35                  40                  45

Met Gln Met Val Lys Leu Arg Gly Gly Ser Lys Gly Leu Val Arg Phe
    50                  55                  60

Tyr Tyr Leu Asp Glu His Arg Ser Cys Ile Arg Trp Arg Pro Ser Arg
65                  70                  75                  80

Lys Asn Glu Lys Ala Lys Ile Ser Ile Asp Ser Ile Gln Glu Val Ser
                85                  90                  95

Glu Gly Arg Gln Ser Glu Val Phe Gln Arg Tyr Pro Asp Gly Ser Phe
            100                 105                 110

Asp Pro Asn Cys Cys Phe Ser Ile Tyr His Gly Ser His Arg Glu Ser
        115                 120                 125

Leu Asp Leu Val Ser Thr Ser Ser Glu Val Ala Arg Thr Trp Val Thr
    130                 135                 140

Gly Leu Arg Tyr Leu Met Ala Gly Ile Ser Asp Glu Asp Ser Leu Ala
145                 150                 155                 160

Arg Arg Gln Arg Thr Arg Asp Gln Trp Leu Lys Gln Thr Phe Asp Glu
                165                 170                 175

Ala Asp Lys Asn Gly Asp Gly Ser Leu Ser Ile Gly Glu Val Leu Gln
            180                 185                 190

Leu Leu His Lys Leu Asn Val Asn Leu Pro Arg Gln Arg Val Lys Gln
        195                 200                 205

Met Phe Arg Glu Ala Asp Thr Asp Asp His Gln Gly Thr Leu Gly Phe
    210                 215                 220

Glu Glu Phe Cys Ala Phe Tyr Lys Met Met Ser Thr Arg Arg Asp Leu
225                 230                 235                 240
```

-continued

```
Tyr Leu Leu Met Leu Thr Tyr Ser Asn His Lys Asp His Leu Asp Ala
                245                 250                 255

Ala Ser Leu Gln Arg Phe Leu Gln Val Glu Gln Lys Met Ala Gly Val
            260                 265                 270

Thr Leu Glu Ser Cys Gln Asp Ile Ile Glu Gln Phe Glu Pro Cys Pro
        275                 280                 285

Glu Asn Lys Ser Lys Gly Leu Leu Gly Ile Asp Gly Phe Thr Asn Tyr
    290                 295                 300

Thr Arg Ser Pro Ala Gly Asp Ile Phe Asn Pro Glu His His Val
305                 310                 315                 320

His Gln Asp Met Thr Gln Pro Leu Ser His Tyr Phe Ile Thr Ser Ser
                325                 330                 335

His Asn Thr Tyr Leu Val Gly Asp Gln Leu Met Ser Gln Ser Arg Val
            340                 345                 350

Asp Met Tyr Ala Trp Val Leu Gln Ala Gly Cys Arg Cys Val Glu Val
        355                 360                 365

Asp Cys Trp Asp Gly Pro Asp Gly Glu Pro Ile Val His His Gly Tyr
    370                 375                 380

Thr Leu Thr Ser Lys Ile Leu Phe Lys Asp Val Ile Glu Thr Ile Asn
385                 390                 395                 400

Lys Tyr Ala Phe Ile Lys Asn Glu Tyr Pro Val Ile Leu Ser Ile Glu
                405                 410                 415

Asn His Cys Ser Val Ile Gln Gln Lys Lys Met Ala Gln Tyr Leu Thr
            420                 425                 430

Asp Ile Leu Gly Asp Lys Leu Asp Leu Ser Ser Val Ser Ser Glu Asp
        435                 440                 445

Ala Thr Thr Leu Pro Ser Pro Gln Met Leu Lys Gly Lys Ile Leu Val
    450                 455                 460

Lys Gly Lys Lys Leu Pro Ala Asn Ile Ser Glu Asp Ala Glu Glu Gly
465                 470                 475                 480

Glu Val Ser Asp Glu Asp Ser Ala Asp Glu Ile Asp Asp Cys Lys
                485                 490                 495

Leu Leu Asn Gly Asp Ala Ser Thr Asn Arg Lys Arg Val Glu Asn Thr
            500                 505                 510

Ala Lys Arg Lys Leu Asp Ser Leu Ile Lys Glu Ser Lys Ile Arg Asp
        515                 520                 525

Cys Glu Asp Pro Asn Asn Phe Ser Val Ser Thr Leu Ser Pro Ser Gly
    530                 535                 540

Lys Leu Gly Arg Lys Ser Lys Ala Glu Glu Asp Val Glu Ser Gly Glu
545                 550                 555                 560

Asp Ala Gly Ala Ser Arg Arg Asn Gly Arg Leu Val Val Gly Ser Phe
                565                 570                 575

Ser Arg Arg Lys Lys Gly Ser Lys Leu Lys Ala Ala Ser Val
            580                 585                 590

Glu Glu Gly Asp Glu Gly Gln Asp Ser Pro Gly Gly Gln Ser Arg Gly
        595                 600                 605

Ala Thr Arg Gln Lys Lys Thr Met Lys Leu Ser Arg Ala Leu Ser Asp
    610                 615                 620

Leu Val Lys Tyr Thr Lys Ser Val Ala Thr His Asp Ile Glu Met Glu
625                 630                 635                 640

Ala Ala Ser Ser Trp Gln Val Ser Ser Phe Ser Glu Thr Lys Ala His
                645                 650                 655
```

-continued

```
Gln Ile Leu Gln Gln Lys Pro Ala Gln Tyr Leu Arg Phe Asn Gln Gln
            660                 665                 670
Gln Leu Ser Arg Ile Tyr Pro Ser Ser Tyr Arg Val Asp Ser Ser Asn
            675                 680                 685
Tyr Asn Pro Gln Pro Phe Trp Asn Ala Gly Cys Gln Met Val Ala Leu
            690                 695                 700
Asn Tyr Gln Ser Glu Gly Arg Met Leu Gln Leu Asn Arg Ala Lys Phe
705                 710                 715                 720
Ser Ala Asn Gly Gly Cys Gly Tyr Val Leu Lys Pro Gly Cys Met Cys
                725                 730                 735
Gln Gly Val Phe Asn Pro Asn Ser Glu Asp Pro Leu Pro Gly Gln Leu
            740                 745                 750
Lys Lys Gln Leu Val Leu Arg Ile Ile Ser Gly Gln Gln Leu Pro Lys
            755                 760                 765
Pro Arg Asp Ser Met Leu Gly Asp Arg Gly Glu Ile Ile Asp Pro Phe
            770                 775                 780
Val Glu Val Glu Ile Ile Gly Leu Pro Val Asp Cys Ser Arg Glu Gln
785                 790                 795                 800
Thr Arg Val Val Asp Asp Asn Gly Phe Asn Pro Thr Trp Glu Glu Thr
                805                 810                 815
Leu Val Phe Met Val His Met Pro Glu Ile Ala Leu Val Arg Phe Leu
            820                 825                 830
Val Trp Asp His Asp Pro Ile Gly Arg Asp Phe Ile Gly Gln Arg Thr
            835                 840                 845
Leu Ala Phe Ser Ser Met Met Pro Gly Tyr Arg His Val Tyr Leu Glu
            850                 855                 860
Gly Met Glu Glu Ala Ser Ile Phe Val His Val Ala Val Ser Asp Ile
865                 870                 875                 880
Ser Gly Lys Val Lys Gln Ala Leu Gly Leu Lys Gly Leu Phe Leu Arg
                885                 890                 895
Gly Pro Lys Pro Gly Ser Leu Asp Ser His Ala Ala Gly Arg Pro Pro
            900                 905                 910
Ala Arg Pro Ser Val Ser Gln Arg Ile Leu Arg Arg Thr Ala Ser Ala
            915                 920                 925
Pro Thr Lys Ser Gln Lys Pro Gly Arg Arg Gly Phe Pro Glu Leu Val
            930                 935                 940
Leu Gly Thr Arg Asp Thr Gly Ser Lys Gly Val Ala Asp Asp Val Val
945                 950                 955                 960
Pro Pro Gly Pro Gly Pro Ala Pro Glu Ala Pro Ala Gln Glu Gly Pro
                965                 970                 975
Gly Ser Gly Ser Pro Arg Gly Lys Ala Pro Ala Ala Val Ala Glu Lys
            980                 985                 990
Ser Pro Val Arg Val Arg Pro Arg Val Leu Asp Gly Pro Gly Pro
            995                 1000                1005
Ala Gly Met Ala Ala Thr Cys Met Lys Cys Val Val Gly Ser Cys Ala
            1010                1015                1020
Gly Val Asn Thr Gly Gly Leu Gln Arg Glu Pro Pro Ser Pro Gly
1025                1030                1035                1040
Pro Ala Ser Arg Gln Ala Ala Ile Arg Gln Pro Arg Ala Arg Ala
                1045                1050                1055
Asp Ser Leu Gly Ala Pro Cys Cys Gly Leu Asp Pro His Ala Ile Pro
            1060                1065                1070
Gly Arg Ser Arg Glu Ala Pro Lys Gly Pro Gly Ala Trp Arg Gln Gly
```

-continued

```
               1075                1080                1085
Pro Gly Gly Ser Gly Ser Met Ser Ser Asp Ser Ser Pro Asp Ser
    1090                1095                1100
Pro Gly Ile Pro Glu Arg Ser Pro Arg Trp Pro Glu Gly Ala Cys Arg
1105                1110                1115                1120
Gln Pro Gly Ala Leu Gln Gly Glu Met Ser Ala Leu Phe Ala Gln Lys
                1125                1130                1135
Leu Glu Glu Ile Arg Ser Lys Ser Pro Met Phe Ser Ala Gly Lys Pro
                    1140                1145                1150
Leu Leu Pro Cys Val Val Leu Pro His Ala Pro Gly Met Ala Gly Pro
            1155                1160                1165
Gly Ser Pro Ala Ala Ala Ser Ala Trp Thr Val Ser Pro Arg Val Leu
    1170                1175                1180
Val Leu Val Ala Leu Tyr Pro Trp His Cys Leu Arg Gly Thr Leu Leu
1185                1190                1195                1200
Pro Trp Leu Ala Cys Gly Pro
                1205

<210> SEQ ID NO 3
<211> LENGTH: 3624
<212> TYPE: DNA
<213> ORGANISM: Homo sapiens

<400> SEQUENCE: 3
atggctcccc cgacagccgg ccccttcct ggcccagctc ttccgcctga ggacccaggg      60
ccggatccgg agagcaggtg gctttcttg agcgccaaca ttctgcccgt ggtggagcgg     120
tgcatgggtg ccatgcaaga ggggatgcag atggtgaagc tgcgtggcgg ctccaagggc    180
ctggtccgct ctactacct ggacgagcac cgctcctgca tccgctggag gccctcacgc     240
aagaacgaga aggccaagat ctccatcgac tccatccagg aggtgagtga ggggcggcag    300
tcggaggtct tccagcgcta ccctgacggc agcttcgacc ccaactgctg cttcagcatc    360
taccacggca gccaccgcga gtcgctggac ctggtctcca ccagcagcga ggtgcgcgc     420 acctgggtca ctggcctgcg ctacctcatg gccggcatca gcgacgagga cagcctggct    480
cgccgccagc gcaccaggga ccagtggctg aagcagacgt ttgacgaggc gacaagaac     540 ggggatggca gcctgagcat ggcgaggtc ctgcagctgc tgcacaagct caacgtgaac     600
ctgccccggc agagggtgaa gcagatgttc agggaagcgg acacggatga ccaccaaggg    660
acgctgggtt ttgaagagtt ctgtgccttc tacaagatga tgtccacccg ccgggacctc    720
tacctgctca tgctgaccta cagcaaccac aaggaccacc tggatgccgc cagcctgcag    780
cgcttcctgc aggtggagca agatggcg gtgtgacccc tcgagagctg ccaggacatc      840
atcgagcagt ttgagccatg cccagaaaac aagagtaagg ggctgctggg cattgatggc    900
ttcaccaact acaccaggag ccctgctggt gacatcttca accctgagca ccaccatgtg    960
caccaggaca tgacgcagcc gctgagccac tacttcatca cctcgtccca aacacctac    1020 ctcgtgggtg accagctcat gtcccagtca cgggtgacaa tgtatgcttg ggtcctgcag   1080
gctggctgcc gctgcgtgga ggtggactgc tgggatgggc cgacgggga gcccattgtg    1140 caccatggct acactctgac ttccaagatc ctcttcaaag acgtcattga aaccatcaac   1200
aaatatgcct tcatcaagaa tgagtaccca gtgatcctgt ccatcgaaaa ccactgcagt   1260
gtcatccagc agaagaaaat ggcccagtat ctgactgaca tccttgggga caagctggac   1320
ctgtcatcag tgagcagtga agatgccacc acactcccct ctccacagat gctcaagggc   1380
```

```
aagatcctcg tgaaggggaa gaagctccca gccaacatca gcgaggatgc ggaggaaggc    1440
gaggtgtctg atgaggacag tgctgatgag attgacgatg actgcaagct cctcaatggg    1500
gatgcatcca ccaatcgaaa gcgtgtagaa aacactgcta agaggaaact ggattccctc    1560
atcaaagagt cgaagattcg ggactgtgag gaccccaaca acttctccgt ctccacactg    1620
tccccatctg gaaagctcgg acgcaagagc aaggctgaag aggacgtgga gtctggggag    1680
gatgccgggg ccagcagacg caatggccgc ctcgtcgtgg gaagcttctc caggcgcaag    1740
aagaagggca gcaagctgaa gaaggcggcc agcgtggagg aggagatgga gggtcaggac    1800
tccccgggag gccagagccg aggggcgacc cggcagaaga gaccatgaa  gctgtcccgg    1860 gccctctctg acctggtgaa gtacaccaag tccgtggcca cccacgacat agagatggag    1920
gcggcgtcca gctggcaggt gtcgtccttc agcgagacca aggcccacca gattctgcag    1980
cagaagccgg cgcagtacct acgcttcaac cagcagcagc tctcccgcat ctacccctcc    2040
tcctaccgtg tggactccag caactacaac ccgcagccct ctggaacgc  cggctgccaa    2100 atggttgccc tgaactacca gtcagagggg cggatgctgc agctgaaccg agccaagttc    2160
agcgccaacg gtggctgcgg ctacgtactc aagcctgggt gcatgtgcca gggcgtgttc    2220
aaccccaact cggaggaccc cctgcccggg cagctcaaga agcagctggt gctccggatc    2280
atcagtggcc agcagcttcc caagccgcgc gactccatgc tgggggaccg tggggagatc    2340
atcgacccct ttgtggaggt ggagatcatt gggctccctg tggactgcag cagggagcag    2400
acccgcgtgg tggacgacaa cggggttcaac cccacctggg aggagaccct ggttttcatg    2460
gtgcacatgc cggagatcgc gctggtccgc ttcctcgtct ggaccacga  tcccatcggg    2520 cgtgacttca ttggccagag gacgctggcc ttcagcagca tgatgccagg ctacagacac    2580
gtgtacctag aagggatgga agaggcctcc atcttcgtgc atgtggctgt cagtgacatc    2640
agcggtaagg tcaagcaggc tctgggccta aaaggcctct tcctccgagg cccaaagccc    2700
ggctcgctgg acagtcatgc tgctgggcgg ccccccggcc ggccctccgt tagccagcgg    2760
atcctgcggc gcacggccag cgccccgacc aagagccaga agccgggccg caggggcttc    2820
ccggagctgg tcctgggtac acgggacaca ggctccaagg gggtggcaga cgatgtggtg    2880
cccccccggg ccggacctgc tccggaagcc ccagcccagg aggggcccgg cagcggcagc    2940
ccccgaggta aggcgccagc tgcggtggca gagaagagcc ctgtgcgagt gcggcccccg    3000
cgtgtcctgg acgccccgg gcctgctggg atggccgcca catgcatgaa gtgtgtggtg    3060
ggatcctgcg ccggcgtgaa caccgggggc ctgcagaggg agcggccacc cagcccgggg    3120
cctgcaagca ggcaggcagc cattcgccag cagccccggg cccgggctga ctcactgggg    3180
gccccctgct gtggcctgga ccctcacgct atcccgggga gaagcagaga ggcccccaag    3240
ggtcctgggg cctggaggca gggtccaggc ggtagcggct ccatgtcctc ggactccagc    3300
agcccagaca gcccgggcat ccccgaaagg tcccccgct  ggcctgaggg tgcctgcagg    3360
caaccggggg ccctgcaggg agagatgagt gccttgtttg ctcaaaagct ggaggagatc    3420
aggagtaaat cccccatgtt ctccgccggt aagcccctct tgccctgcgt ggtcctcccg    3480
cacgcccctg gcatggctgg gcctgggtca cctgctgctg cttctgcgtg gacggtgtcg    3540
cctcgtgtgc tcgtgctcgt ggctctgtat ccgtggcact gtctccgtgg cactctgctc    3600
ccttggcttg cctgtggccc atag                                          3624
```

<210> SEQ ID NO 4

```
<211> LENGTH: 85
<212> TYPE: PRT
<213> ORGANISM: Artificial Sequence
<220> FEATURE:
<223> OTHER INFORMATION: Consensus amino acid

<400> SEQUENCE: 4

Val Ile Lys Glu Gly Trp Leu Leu Lys Ser Lys Ser Trp Lys Lys
 1               5                  10                  15

Arg Tyr Phe Val Leu Phe Asn Asn Val Leu Leu Tyr Tyr Lys Asp Ser
            20                  25                  30

Lys Lys Lys Pro Lys Gly Ser Ile Pro Leu Ser Gly Cys Gln Val Glu
        35                  40                  45

Lys Pro Asp Lys Asn Cys Phe Glu Ile Arg Thr Asp Arg Thr Leu Leu
    50                  55                  60

Leu Gln Ala Glu Ser Glu Glu Arg Lys Glu Trp Val Lys Ala Ile
65                  70                  75                  80

Gln Ser Ala Ile Arg
            85

<210> SEQ ID NO 5
<211> LENGTH: 29
<212> TYPE: PRT
<213> ORGANISM: Artificial Sequence
<220> FEATURE:
<223> OTHER INFORMATION: Consensus amino acid

<400> SEQUENCE: 5

Glu Leu Lys Glu Ala Phe Lys Glu Phe Asp Lys Asp Gly Asp Gly Lys
 1               5                  10                  15

Ile Ser Phe Glu Glu Phe Lys Ala Ala Leu Lys Lys Leu
            20                  25

<210> SEQ ID NO 6
<211> LENGTH: 29
<212> TYPE: PRT
<213> ORGANISM: Artificial Sequence
<220> FEATURE:
<223> OTHER INFORMATION: Consensus amino acid

<400> SEQUENCE: 6

Glu Leu Lys Glu Ala Phe Lys Glu Phe Asp Lys Asp Gly Asp Gly Lys
 1               5                  10                  15

Ile Ser Phe Glu Glu Phe Lys Ala Ala Leu Lys Lys Leu
            20                  25

<210> SEQ ID NO 7
<211> LENGTH: 153
<212> TYPE: PRT
<213> ORGANISM: Artificial Sequence
<220> FEATURE:
<223> OTHER INFORMATION: Consensus amino acid

<400> SEQUENCE: 7

Asp Met Ser Ile Pro Leu Ser His Tyr Phe Ile Ser Ser His Asn
 1               5                  10                  15

Thr Tyr Leu Thr Gly Lys Gln Leu Trp Gly Lys Ser Ser Val Glu Ser
            20                  25                  30

Tyr Arg Gln Gln Leu Asp Ala Gly Cys Arg Cys Val Glu Leu Asp Cys
        35                  40                  45

Trp Asp Gly Lys Pro Asp Asp Glu Pro Ile Ile Tyr His Gly His Thr
    50                  55                  60
```

-continued

```
Leu Thr Leu Glu Ile Lys Leu Lys Asp Val Leu Glu Ala Ile Lys Asp
 65                  70                  75                  80

Phe Ala Phe Lys Pro Thr Ser Pro Tyr Pro Val Ile Leu Ser Leu Glu
                 85                  90                  95

Asn His Cys Asn Ser Asp Asp Gln Gln Arg Lys Met Ala Lys Tyr Phe
            100                 105                 110

Lys Glu Ile Phe Gly Asp Met Leu Leu Thr Lys Pro Thr Leu Asp Ser
        115                 120                 125

Leu Thr Thr Glu Pro Gly Leu Pro Leu Pro Ser Leu Lys Asp Leu Arg
    130                 135                 140

Gly Lys Ile Leu Leu Lys Asn Lys Lys
145                 150
```

<210> SEQ ID NO 8
<211> LENGTH: 128
<212> TYPE: PRT
<213> ORGANISM: Artificial Sequence
<220> FEATURE:
<223> OTHER INFORMATION: Consensus amino acid

<400> SEQUENCE: 8

```
Glu Leu Ser Asn Leu Val Asn Tyr Ile Gln Ser Ile Lys Phe Arg Ser
  1               5                  10                  15

Phe Glu Leu Ser Gly Glu Lys Asn Thr Ser Tyr Glu Ile Ser Ser
                 20                  25                  30

Phe Ser Glu Arg Lys Val Lys Ala Lys Leu Leu Lys Glu Ser Pro
             35                  40                  45

Val Glu Phe Val Lys Tyr Asn Lys Arg Gln Leu Ser Arg Val Tyr Pro
 50                  55                  60

Lys Gly Thr Arg Val Asp Ser Ser Asn Phe Met Pro Gln Val Phe Trp
 65                  70                  75                  80

Asn Ala Gly Cys Gln Met Val Ala Leu Asn Phe Gln Thr Ser Asp Leu
             85                  90                  95

Pro Met Gln Ile Asn Asp Gly Met Phe Glu Tyr Asn Gly Gly Gln Pro
            100                 105                 110

Asp Gly Ser Phe Lys Ser Gly Tyr Leu Leu Lys Pro Glu Phe Leu Arg
        115                 120                 125
```

<210> SEQ ID NO 9
<211> LENGTH: 95
<212> TYPE: PRT
<213> ORGANISM: Artificial Sequence
<220> FEATURE:
<223> OTHER INFORMATION: Consensus amino acid

<400> SEQUENCE: 9

```
Leu Thr Val Thr Val Ile Glu Ala Arg Asn Leu Pro Lys Met Asp Lys
  1               5                  10                  15

Val Asn Gly Arg Leu Ser Asp Pro Tyr Val Lys Val Ser Leu Leu Gly
                 20                  25                  30

Asp Lys Lys Asp Leu Lys Lys Phe Lys Thr Lys Val Val Lys Lys Thr
             35                  40                  45

Asn Gly Leu Asn Pro Val Trp Asn Glu Thr Phe Val Phe Glu Lys
 50                  55                  60

Val Pro Leu Pro Glu Leu Ala Ser Lys Thr Leu Arg Phe Ala Val Tyr
 65                  70                  75                  80

Asp Glu Asp Arg Phe Ser Arg Asp Asp Phe Ile Gly Gln Val Thr
```

<210> SEQ ID NO 10
<211> LENGTH: 325
<212> TYPE: PRT
<213> ORGANISM: Artificial Sequence
<220> FEATURE:
<223> OTHER INFORMATION: Consensus amino acid

<400> SEQUENCE: 10

```
Gln Val Lys Gln Ala Leu Gly Leu Lys Gly Leu Phe Leu Arg Gly Pro
  1               5                  10                  15

Lys Pro Gly Ser Leu Asp Ser His Ala Ala Gly Arg Pro Pro Ala Arg
             20                  25                  30

Pro Ser Val Ser Gln Arg Ile Leu Arg Arg Thr Ala Ser Ala Pro Thr
         35                  40                  45

Lys Ser Gln Lys Pro Gly Arg Arg Gly Phe Pro Glu Leu Val Leu Gly
     50                  55                  60

Thr Arg Asp Thr Gly Ser Lys Gly Val Ala Asp Val Val Pro Pro
 65                  70                  75                  80

Gly Pro Gly Pro Ala Pro Glu Ala Pro Ala Gln Glu Gly Pro Gly Ser
                 85                  90                  95

Gly Ser Pro Arg Gly Lys Ala Pro Ala Ala Val Ala Glu Lys Ser Pro
            100                 105                 110

Val Arg Val Arg Pro Pro Arg Val Leu Asp Gly Pro Gly Pro Ala Gly
            115                 120                 125

Met Ala Ala Thr Cys Met Lys Cys Val Val Gly Ser Cys Ala Gly Val
        130                 135                 140

Asn Thr Gly Gly Leu Gln Arg Glu Arg Pro Pro Ser Pro Gly Pro Ala
145                 150                 155                 160

Ser Arg Gln Ala Ala Ile Arg Gln Gln Pro Arg Ala Arg Ala Asp Ser
                165                 170                 175

Leu Gly Ala Pro Cys Cys Gly Leu Asp Pro His Ala Ile Pro Gly Arg
            180                 185                 190

Ser Arg Glu Ala Pro Lys Gly Pro Gly Ala Trp Arg Gln Gly Pro Gly
            195                 200                 205

Gly Ser Gly Ser Met Ser Ser Asp Ser Ser Pro Asp Ser Pro Gly
        210                 215                 220

Ile Pro Glu Arg Ser Pro Arg Trp Pro Glu Gly Ala Cys Arg Gln Pro
225                 230                 235                 240

Gly Ala Leu Gln Gly Glu Met Ser Ala Leu Phe Ala Gln Lys Leu Glu
                245                 250                 255

Glu Ile Arg Ser Lys Ser Pro Met Phe Ser Ala Gly Lys Pro Leu Leu
            260                 265                 270

Pro Cys Val Val Leu Pro His Ala Pro Gly Met Ala Gly Pro Gly Ser
        275                 280                 285

Pro Ala Ala Ala Ser Ala Trp Thr Val Ser Pro Arg Val Leu Val Leu
    290                 295                 300

Val Ala Leu Tyr Pro Trp His Cys Leu Arg Gly Thr Leu Leu Pro Trp
305                 310                 315                 320

Leu Ala Cys Gly Pro
                325
```

<210> SEQ ID NO 11
<211> LENGTH: 158
<212> TYPE: PRT

```
<213> ORGANISM: Artificial Sequence
<220> FEATURE:
<223> OTHER INFORMATION: Consensus amino acid

<400> SEQUENCE: 11

Ser Pro Asp Cys Asn Val Phe Asp Pro Glu His Lys Gln Val His Gln
 1               5                  10                  15

Asp Met Asn Gln Pro Leu Ser His Tyr Phe Ile Asn Ser Ser His Asn
            20                  25                  30

Thr Tyr Leu Thr Gly Asn Gln Leu Ser Ser Gly Glu Ser Ser Val Glu
        35                  40                  45

Met Tyr Arg Gln Ala Leu Leu Lys Gly Cys Arg Cys Ile Glu Leu Asp
50                  55                  60

Cys Trp Asp Gly Lys Asp Gly Asp Pro Glu Pro Ile Ile Thr His Gly
65                  70                  75                  80

His Thr Met Thr Thr Glu Ile Ser Phe Lys Asp Cys Leu Glu Ala Ile
                85                  90                  95

Lys Glu His Ala Phe Val Thr Ser Glu Tyr Pro Val Ile Leu Ser Leu
                100                 105                 110

Glu Asn His Cys Asp Ser Thr Pro Gln Gln Gln Ala Lys Met Ala Glu
            115                 120                 125

Tyr Cys Lys Glu Val Phe Gly Asp Met Leu Phe Thr Glu Pro Leu Glu
130                 135                 140

Glu Ser Pro Leu Glu Pro Gly Lys Glu Leu Pro Ser Pro Glu
145                 150                 155

<210> SEQ ID NO 12
<211> LENGTH: 41
<212> TYPE: PRT
<213> ORGANISM: Artificial Sequence
<220> FEATURE:
<223> OTHER INFORMATION: Consensus amino acid

<400> SEQUENCE: 12

Lys Arg Lys Ile Leu Ile Lys Asn Lys Lys Leu Lys Glu His Ser Glu
 1               5                  10                  15

Glu Lys Glu Ser Glu Glu Lys Lys Thr Asp Glu Glu Thr Glu Ser Glu
            20                  25                  30

Glu Glu Asp Glu Met Gly Ser Asp Ala
        35                  40

<210> SEQ ID NO 13
<211> LENGTH: 18
<212> TYPE: PRT
<213> ORGANISM: Artificial Sequence
<220> FEATURE:
<223> OTHER INFORMATION: Consensus amino acid

<400> SEQUENCE: 13

Pro Gly Lys Glu Leu Pro Ser Pro Glu Glu Leu Lys Arg Lys Ile Leu
 1               5                  10                  15

Ile Lys

<210> SEQ ID NO 14
<211> LENGTH: 181
<212> TYPE: PRT
<213> ORGANISM: Artificial Sequence
<220> FEATURE:
<223> OTHER INFORMATION: Consensus amino acid

<400> SEQUENCE: 14
```

Cys Leu Gln Phe Met Gln Lys Gly Ser Glu Leu Lys Lys Val Arg Ser
1               5                   10                  15

Asn Ser Trp Lys Tyr Asn Arg Tyr Phe Thr Leu Asp Asp Met Gln
            20                  25                  30

Thr Leu Trp Trp Glu Pro His Trp Phe Ser Lys Lys Asp Ser Glu Lys
        35                  40                  45

Pro Lys Phe Asp Ile Ser Asp Ile Lys Glu Ile Arg Met Gly Lys Asn
    50                  55                  60

Thr Glu Thr Phe Arg Asn Asn Gly Lys Glu Phe Gln Ile Gln Glu Pro
65                  70                  75                  80

Glu Asp Cys Cys Phe Ser Ile Ile Phe Gly Glu Asn Tyr Phe His Glu
                85                  90                  95

Ser Leu Asp Leu Val Ala Asn Ser Ala Asp Val Ala Asn Ile Trp Val
            100                 105                 110

Ser Gly Leu Arg Tyr Leu Val Asp Tyr Ala Lys His Met Leu Asp Asn
            115                 120                 125

Tyr Gln Glu Gln Leu Asp Gln Trp Leu Arg Glu Trp Phe Gln Gln Ala
130                 135                 140

Asp Arg Asn Lys Asp Ser Arg Met Ser Phe Arg Glu Ala Gln Asn Leu
145                 150                 155                 160

Leu Lys Leu Met Asn Val Gln Met Asp Glu Gly Tyr Ala Phe Ser Ile
                165                 170                 175

Phe Arg Glu Cys Asp
            180

<210> SEQ ID NO 15
<211> LENGTH: 134
<212> TYPE: PRT
<213> ORGANISM: Artificial Sequence
<220> FEATURE:
<223> OTHER INFORMATION: Consensus amino acid

<400> SEQUENCE: 15

Phe Asp Glu Phe Asp Thr Asp Gly Asn Gly His Leu Asp Glu Gln Thr
1               5                   10                  15

Ala Phe Lys Cys Ile Lys His Leu Asn Pro Arg Leu Lys His His Lys
            20                  25                  30

Ile Thr Asn Lys Phe Lys Glu Ile Thr Ile Lys Ser Lys Glu Lys Glu
        35                  40                  45

Arg Thr Lys Ile Thr Lys Glu His Phe Val Asp Leu Tyr Lys Glu Leu
    50                  55                  60

Gly Thr Arg Pro Glu Val Tyr Phe Leu Met Val Gln Tyr Ser Lys Asn
65                  70                  75                  80

Lys Asp Tyr Leu Asp Cys Gln Asp Leu Met Leu Phe Leu Glu Thr Glu
                85                  90                  95

Gln Gly Met Val His Val Thr Glu Asp Asn Cys Leu Asp Ile Ile Glu
            100                 105                 110

Gln Tyr Glu Pro Cys Ser Glu Gly Arg Glu Asn Gly Trp Met Thr Ile
            115                 120                 125

Asp Gly Phe Thr Ser Tyr
130

<210> SEQ ID NO 16
<211> LENGTH: 92
<212> TYPE: PRT
<213> ORGANISM: Artificial Sequence -continued

```
<220> FEATURE:
<223> OTHER INFORMATION: Consensus amino acid

<400> SEQUENCE: 16

Phe Ser Ser Leu Val Pro Gly Tyr Arg His Val Tyr Leu Glu Gly Leu
 1               5                  10                  15

Thr Glu Ala Ser Ile Phe Val His Ile Thr Ile Asn Glu Ile Tyr Gly
            20                  25                  30

Lys Asn Arg Gln Leu Gln Gly Leu Lys Gly Leu Phe Asn Lys Asn Pro
        35                  40                  45

Arg His Ser Ser Ser Glu Asn Asn Ser His Tyr Val Arg Lys Arg Ser
    50                  55                  60

Ile Gly Asp Arg Ile Leu Arg Arg Thr Ala Ser Ala Pro Ala Lys Gly
65                  70                  75                  80

Arg Lys Lys Ser Lys Met Gly Phe Gln Glu Met Val
                85                  90

<210> SEQ ID NO 17
<211> LENGTH: 51
<212> TYPE: PRT
<213> ORGANISM: Artificial Sequence
<220> FEATURE:
<223> OTHER INFORMATION: Consensus amino acid
<221> NAME/KEY: VARIANT
<222> LOCATION: (1)...(51)
<223> OTHER INFORMATION: Xaa = Any Amino Acid

<400> SEQUENCE: 17

Asp Xaa Asp Asn Ser Ile Leu Val Phe Tyr Trp Asp Glu Asn Ser Thr
 1               5                  10                  15

Gly Asp Asn Gln Gly His Arg Lys Gly Pro Leu Ile Val Met Cys Asp
            20                  25                  30

Glu Asn Gln Ser Thr Ala Gly Cys Xaa Xaa Asp Glu Leu Ile Val Met
        35                  40                  45

Phe Tyr Trp
    50
```

32544, A NOVEL HUMAN PHOSPHOLIPASE C AND USES THEREOF

This application claims priority on U.S. Application Ser. No. 60/246,808 filed Nov. 8, 2000, which is relied on and incorporated herein by reference in its entirety.

BACKGROUND OF THE INVENTION

Phospholipase C (PLC) belongs to a family of enzymes, also known as disulfide isomerases, which play an important role in mediating signal transduction pathways. Many extracellular signaling molecules including hormones, growth factors, neurotransmitters, and immunoglobulin bind to their respective cell surface receptors and activate PLCS. Activated PLCs then catalyze the hydrolysis of phosphatidyl-inositol-4,5-bisphosphate (PIP2), a component of the plasma membrane, to produce diacylglycerol and inositol 1,4,5-trisphosphate (IP3).

In their respective biochemical pathways, IP3 and diacylglycerol serve as second messengers and trigger a series of intracellular responses. IP3 induces the release of calcium from internal cellular storage, and diacylglycerol activates protein kinase C (PKC). Both pathways are part of transmembrane signal transduction mechanisms, which regulate numerous cellular processes, including secretion, neural activity, metabolism, and proliferation.

PLC molecules have been found in a broad spectrum of organisms including bacteria, simple eukaryotes, plants and animals (Munnik et al., Biochim. Biophys. Acta. 1389:222–272, (1998)). Several distinct isoforms of PLC have been identified in animals and are categorized as PLC-beta, PLC-gamma, and PLC-delta. Subtypes are designated by adding Arabic numbers after the Greek letters, e.g., PLC-beta-1. PLCs have a molecular mass of 62–68 kDa, and their amino acid sequences show two regions of significant similarity.

SUMMARY OF THE INVENTION

The present invention is based, in part, on the discovery of a novel human phospholipase, referred to herein as "32544". The nucleotide sequence of a cDNA encoding 32544 is shown in SEQ ID NO:1, and the amino acid sequence of a 32544 polypeptide is shown in SEQ ID NO:2. In addition, the nucleotide sequence of the coding region is depicted in SEQ ID NO:3.

Accordingly, in one aspect, the invention features a nucleic acid molecule which encodes a 32544 protein or polypeptide, e.g., a biologically active portion of the 32544 protein. In a preferred embodiment, the isolated nucleic acid molecule encodes a polypeptide having the amino acid sequence of SEQ ID NO:2. In other embodiments, the invention provides an isolated 32544 nucleic acid molecule having the nucleotide sequence shown in SEQ ID NO:1 or SEQ ID NO:3. In still other embodiments, the invention provides nucleic acid molecules that are substantially identical (e.g., naturally occurring allelic variants) to the nucleotide sequence shown in SEQ ID NO:1 or SEQ ID NO:3. In other embodiments, the invention provides a nucleic acid molecule which hybridizes under stringent hybridization conditions to a nucleic acid molecule comprising the nucleotide sequence of SEQ ID NO:1 or SEQ ID NO:3, wherein the nucleic acid encodes a full length 32544 protein or an active fragment thereof.

In a related aspect, the invention further provides nucleic acid constructs which include a 32544 nucleic acid molecule described herein. In certain embodiments, the nucleic acid molecules of the invention are operatively linked to native or heterologous regulatory sequences. Also included, are vectors and host cells containing the 32544 nucleic acid molecules of the invention e.g., vectors and host cells suitable for producing 32544 nucleic acid molecules and polypeptides.

In another related aspect, the invention provides nucleic acid fragments suitable as primers or hybridization probes for the detection of 32544-encoding nucleic acids.

In still another related aspect, isolated nucleic acid molecules that are antisense to a 32544 encoding nucleic acid molecule are provided.

In another aspect, the invention features, 32544 polypeptides, and biologically active or antigenic fragments thereof that are useful, e.g., as reagents or targets in assays applicable to treatment and diagnosis of 32544-mediated or related disorders. In another embodiment, the invention provides 32544 polypeptides having a 32544 activity. Preferred polypeptides are 32544 proteins including at least one domain, e.g., a PLC-X domain (from about amino acids 323–468 of SEQ ID NO:2), a PLC-Y domain (from about amino acids 621–736 of SEQ ID NO:2), a calcium binding (C2) domain (from about amino acids 756–848 of SEQ ID NO:2), or a pleckstrin homology (PH) domain (from about amino acids 44–151 of SEQ ID NO:2), and, preferably, having a 32544 activity, e.g., an activity as described herein, e.g., the ability to catalyze the hydrolysis of phosphatidyl-inositol-4,5-bisphosphate (PIP2) producing diacylglycerol and inositol 1,4,5-trisphosphate (IP3).

In other embodiments, the invention provides 32544 polypeptides, e.g., a 32544 polypeptide having the amino acid sequence shown in SEQ ID NO:2; an amino acid sequence that is substantially identical to the amino acid sequence shown in SEQ ID NO:2; or an amino acid sequence encoded by a nucleic acid molecule having a nucleotide sequence which hybridizes under stringent hybridization conditions to a nucleic acid molecule comprising the nucleotide sequence of SEQ ID NO:1 or SEQ ID NO:3; wherein the nucleic acid encodes a full length 32544 protein or an active fragment thereof.

In a related aspect, the invention further provides nucleic acid constructs which include a 32544 nucleic acid molecule described herein.

In a related aspect, the invention provides 32544 polypeptides or fragments operatively linked to non-32544 polypeptides to form fusion proteins.

In another aspect, the invention features antibodies and antigen-binding fragments thereof, that react with, or more preferably specifically bind 32544 polypeptides.

In another aspect, the invention provides methods of screening for compounds that modulate the expression or activity of the 32544 polypeptides or nucleic acids.

In still another aspect, the invention provides a process for modulating 32544 polypeptide or nucleic acid expression or activity, e.g. using the screened compounds. In certain embodiments, the methods involve treatment of conditions related to aberrant activity or expression of the 32544 polypeptides or nucleic acids, such as conditions involving aberrant or deficient cellular proliferation or differentiation.

The invention also provides assays for determining the activity of or the presence or absence of 32544 polypeptides or nucleic acid molecules in a biological sample, including for disease diagnosis.

In further aspect the invention provides assays for determining the presence or absence of a genetic alteration in a 32544 polypeptide or nucleic acid molecule, including for disease diagnosis.

BRIEF DESCRIPTION OF THE DRAWINGS

FIGS. 1A–C depicts a cDNA sequence (SEQ ID NO:1) and predicted amino acid sequence (SEQ ID NO:2) of human 32544. The methionine-initiated open reading frame of human 32544 (without the 5' and 3' untranslated regions) extends from nucleotide position 1 to position 3621 of SEQ ID NO:3, not including the terminal codon.

FIG. 3 depicts an alignment of the PH domain of human 32544 with a consensus amino acid sequence derived from a hidden Markov model (HMM) from PFAM. The upper sequences are the consensus amino acid sequence (SEQ ID NO:4), while the lower amino acid sequences correspond to amino acids 44 to 151 of SEQ ID NO:2.

FIGS. 4a–b depict an alignment of the EF hand domain of human 32544 with a consensus amino acid sequence derived from a hidden Markov model (HMM) from PFAM. The upper sequences are the consensus amino acid sequence (SEQ ID NOs:5–6), while the lower amino acid sequences correspond to amino acids 169 to 197 and 205 to 234 of SEQ ID NO:2.

FIG. 5 depicts an alignment of the phosphatidylinositol-specific phospholipase X domain of human 32544 with a consensus amino acid sequence derived from a hidden Markov model (HMM) from PFAM. The upper sequences are the consensus amino acid sequence (SEQ ID NO:7), while the lower amino acid sequences correspond to amino acids 323 to 468 of SEQ ID NO:2.

FIG. 6 depicts an alignment of the phosphatidylinositol-specific phospholipase Y domain of human 32544 with a consensus amino acid sequence derived from a hidden Markov model (HMM) from PFAM. The upper sequences are the consensus amino acid sequence (SEQ ID NO:8), while the lower amino acid sequences correspond to amino acids 621 to 736 of SEQ ID NO:2.

FIG. 7 depicts an alignment of the C2 domain of human 32544 with a consensus amino acid sequence derived from a hidden Markov model (HMM) from PFAM. The upper sequences are the consensus amino acid sequence (SEQ ID NO:9), while the lower amino acid sequences correspond to amino acids 756 to 848 of SEQ ID NO:2.

FIG. 8 depicts a BLAST alignment of human 32544 with a consensus amino acid sequence derived from a ProDomain "KIAA0450" (PD183899) (Release 2001.1; www.toulouse.inra.fr/prodom.html). The lower sequence is amino acid residues 101 to 425 of the 425 amino acid consensus sequence (SEQ ID NO:10), while the upper amino acid sequence corresponds to the "KIAA0450" domain of human 32544, amino acid residues 883 to 1207 of SEQ ID NO:2.

FIGS. 9a–c depict a BLAST alignment of human 32544 with a consensus amino acid sequence derived from a ProDomain "phospholipase phosphodiesterase hydrolase phosphoinositide-specific 1-phosphatidylinositol-45-bisphosphate degradation tranducer lipid beta" (PD001214) (Release 2001.1; www.toulouse.inra.fr/prodom.html). The lower sequence is amino acid residues 2 to 159, 162 to 202, and 151 to 168 of the 219 amino acid consensus sequence (SEQ ID NOs: 1–13), while the upper amino acid sequence corresponds to the "phospholipase phosphodiesterase hydrolase phosphoinositide-specific 1-phosphatidylinositol-45-bisphosphate degradation tranducer lipid beta" domain of human 32544, amino acid residues 307 to 456, 514 to 562, and 742 to 759 of SEQ ID NO:2. FIG. 9a depicts the first local alignment, FIG. 9b the second, and FIG. 9c the third.

FIG. 10 depicts a BLAST alignment of human 32544 with a consensus amino acid sequence derived from a ProDomain "phospholipase C delta calcium-binding PLC-III hydrolase phosphodiesterase lipid PLC-delta-1 1-phosphatidylinositol-45-bisphosphate" (PD186804) (Release 2001.1; www.toulouse.inra.fr/prodom.html). The lower sequence is amino acid residues 14 to 194 of the 203 amino acid consensus sequence (SEQ ID NO:14), while the upper amino acid sequence corresponds to the "phospholipase C delta calcium-binding PLC-III hydrolase phosphodiesterase lipid PLC-delta-1-phosphatidylinositol-45-bisphosphate" domain of human 32544, amino acid residues 41 to 214 of SEQ ID NO:2.

FIG. 11 depicts a BLAST alignment of human 32544 with a consensus amino acid sequence derived from a ProDomain "phospholipase binding C KDA-INS145P3 K10F12.3" (PD023751) (Release 2001.1; http://www.toulouse.inra.fr/prodom.html). The lower sequence is amino acid residues 2 to 135 of the 136 amino acid consensus sequence (SEQ ID NO:15), while the upper amino acid sequence corresponds to the "phospholipase binding CKDA-INS145P3 K10F12.3" domain of human 32544, amino acid residues 174 to 304 of SEQ ID NO:2.

FIG. 12 depicts a BLAST alignment of human 32544 with a consensus amino acid sequence derived from a ProDomain "FLJ12548 similar FIS cDNA phosphatidylinositol-45-bisphosphate NT2RM4000657 delta phosphodiesterase weakly 1-" (PD308221) (Release 2001.1; www.toulouse.inra.fr/prodom.html). The lower sequence is amino acid residues 2 to 93 of the 187 amino acid consensus sequence (SEQ ID NO:16), while the upper amino acid sequence corresponds to the "FLJ12548 similar FIS cDNA phosphatidylinositol-45-bisphosphate NT2RM4000657 delta phosphodiesterase weakly 1-" domain of human 32544, amino acid residues 851 to 944 of SEQ ID NO:2.

Figure 2:
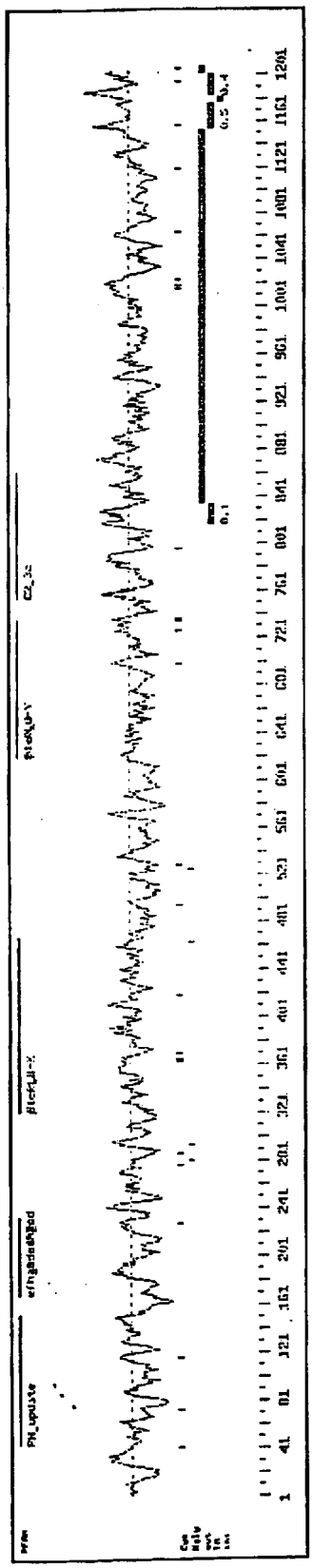
FIG. 2 depicts a hydropathy plot of human 32544. Relatively hydrophobic residues are shown above the dashed horizontal line, and relatively hydrophilic residues are below the dashed horizontal line. The location of the transmembrane domains, and the extracellular and intracellular portions is also indicated. The cysteine residues (cys) and N-glycosylation sites (Ngly) are indicated by short vertical lines just below the hydropathy trace. The numbers corresponding to the amino acid sequence of human 32544 are indicated. Polypeptides of the invention include fragments which include: all or part of a hydrophobic sequence, e.g., a sequence above the dashed line, e.g., the sequence from about amino acid 25 to 40, from about 180 to 190, and from about 815 to 830 SEQ ID NO:2; all or part of a hydrophilic sequence, e.g., a sequence below the dashed line, e.g., the sequence from about amino acid 60 to 80, from about 160 to 180, and from about 590 to 610 of SEQ ID NO:2; a sequence which includes a Cys, or a glycosylation site.

Other features and advantages of the invention will be apparent from the following detailed description, and from the claims.

DETAILED DESCRIPTION

Human 32544

The human 32544 sequence (FIG. 1; SEQ ID NO:1), which is approximately 4635 nucleotides long including untranslated regions, contains a predicted methionine-initiated coding sequence of about 3621 nucleotides (nucleotides 435–4055 of SEQ ID NO:1; SEQ ID NO:3), not including the terminal codon. The coding sequence encodes a 1207 amino acid protein (SEQ ID NO:2).

This mature protein form is approximately 1207 amino acid residues in length (from about amino acid 1 to amino acid 1207 of SEQ ID NO:2). Human 32544 may contain the following regions or other structural features:

- a tyrosine kinase phosphorylation site (PS00007) from about amino acid residues 620–628 of SEQ ID NO:2;
- three amidation sites (PS00009) from about amino acid residues 465–468, 546–549, and 935–938 of SEQ ID NO:2;
- an EF-hand calcium-binding domain (PS00018) from about amino acid residues 178–190;
- four N-glycosylation sites (PS00001) located at about amino acids 290–293, 303–306, 472–475, and 534–537 of SEQ ID NO:2;
- one cAMP- and cGMP-dependent protein kinase phosphorylation site (PS00004) at about amino acids 581–584 of SEQ ID NO:2;
- seventeen predicted protein kinase C sites (PS00005) at about amino acids 79–81, 124–126, 235–237, 387–389, 504–506, 512–514, 543–545, 565–567, 577–579, 615–617, 681–683, 881–883, 918–920, 932–934, 980–982, 1111–1113, and 1180–1182 of SEQ ID NO:2; and
- eighteen predicted casein kinase II phosphorylation sites (PS00006) located at about amino acids 91–94, 124–127, 134–137, 154–157, 173–176, 186–189, 236–239, 276–279, 350–353, 445–448, 483–486, 487–490, 550–553, 558–561, 591–594, 649–652, 812–815, and 1100–1103 of SEQ ID NO:2.

For general information regarding PFAM identifiers, PS prefix and PF prefix domain identification numbers, refer to Sonnhammer et al. (1997) *Protein* 28:405–420 and www.psc.edu/general/software/packages/pfam/pfam.html.

To identify the presence of a "phospholipase family" domain in a 32544 protein sequence (Pfam accession number 00387 and 00388), and make the determination that a polypeptide or protein of interest has a particular profile, the amino acid sequence of the protein can be searched against a database of HMMs (e.g., the Pfam database, release 2.1) using the default parameters (www.sanger.ac.uk/Software/Pfam/HMM_search). For example, the hmmsf program, which is available as part of the HMMER package of search programs, is a family specific default program for MIL-PAT0063 and a score of 15 is the default threshold score for determining a hit. Alternatively, the threshold score for determining a hit can be lowered (e.g., to 8 bits). A description of the Pfam database can be found in Sonnhammer et al., (1997) *Proteins* 28(3):405–420 and a detailed description of HMMs can be found, for example, in Gribskov et al., (1990) *Meth. Enzymol.* 183:146–159; Gribskov et al., (1987) *Proc. Natl. Acad. Sci. USA* 84:4355–4358; Krogh et al., (1994) *J. Mol. Biol.* 235:1501–1531; and Stultz et al., (1993) *Protein Sci.* 2:305–314, the contents of which are incorporated herein by reference.

The 32544 protein contains a significant number of structural characteristics in common with members of the phospholipase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional domains such as a pleckstrin homology domain, a phosphatidylinositol-specific phospholipase domain X (PLC-X) domain, a phosphatidylinositol-specific phospholipase domain Y (PLC-Y) domain, an EF hand domain, or a C2 domain. Members of this family can also have common functional characteristics, e.g., the ability to hydrolyze phosphatidylinositols.

A 32544 polypeptide can include an "EF hand domain" or regions homologous with an "EF hand domain". As used herein, the term "EF hand domain" refers to a protein domain having an amino acid sequence of about 10 to 50, preferably about 10 to 40, more preferably about 29–30 amino acid residues. By an "EF hand domain" is meant a domain that consists of a twelve residue loop flanked on both side by a twelve residue alpha-helical domain. In an EF-hand loop the calcium ion is coordinated in a pentagonal bipyramidal configuration. The six residues involved in the binding are in positions 1, 3, 5, 7, 9 and 12; these residues are denoted by X, Y, Z, –Y, –X and –Z. The invariant Glu or Asp at position 12 provides two oxygens for liganding Ca (bidentate ligand). As used herein, the term "EF hand" includes an amino acid sequence of about 28 amino acid residues in length and having a bit score for the alignment of the sequence to the EF hand domain (HMM) of at least 10. Preferably, an EF hand domain includes at least about 10–50 amino acids, more preferably about 10–35 amino acid residues, or about 20–30 amino acids and has a bit score for the alignment of the sequence to the EF hand domain (HMM) of at least 15, 20, or greater. An alignment of the EF hand domain (amino acids 169 to 197 and 205 to 234 of SEQ ID NO:2) of human EF hand with a consensus amino acid sequence derived from a hidden Markov model is depicted in FIG. 4.

Preferably, the EF hand domain includes the following amino acid consensus sequence having Prosite signature as PS00018, or sequences homologous thereto:

D-x-[DNS]-{ILVFYW}-[DENSTG]-[DNQGHRK]-{GP}-[LIVMC]-[DENQSTAGC]-x(2)-[DE]-[LIVMFYW](SEQ ID NO:17).

In the above conserved motif, and other motifs described herein, the standard IUPAC one-letter code for the amino acids is used. Each element in the pattern is separated by a dash (-); square brackets ([ ]) indicate the particular residues that are accepted at that position; x indicates that any residue is accepted at that position; and numbers in parentheses (()) indicate the number of residues represented by the accompanying amino acid. The EF hand domain of 32544 is found in the N-terminal cytoplasmic domain.

A 32544 polypeptide can include a "pleckstrin homology (PH) domain" or regions homologous with a "PH domain". As used herein, the term "PH domain" refers to a protein domain having an amino acid sequence of about 10 to 200, preferably about 50 to 150, more preferably about 108 amino acid residues. By "PH domain" is meant a domain that can function as a recognition site for a phosphatidylinositol, e.g., a 3,4,5-trisphosphate (PIP3) or another kinase ligand product, and can function as a means to localize PLC to the cytoplasmic face of the plasma membrane. As used herein, the term "PH domain" includes an amino acid sequence of about 108 amino acid residues in length and having a bit score for the alignment of the sequence to the PH domain (HMM) of at least 10. Preferably, a PH domain includes at least about 10–200 amino acids, more preferably about 15–150 amino acid residues, or about 50–110 amino acids and has a bit score for the alignment of the sequence to the PH domain (HMM) of at least 15, 20, or greater. An alignment of the PH domain (amino acids 44 to 151 of SEQ ID NO:2) of human PH with a consensus amino acid sequence derived from a hidden Markov model is depicted in FIG. 3.

In a preferred embodiment 32544 polypeptide or protein has a "PH domain" or a region which includes at least about 10–200 amino acids, more preferably about 15–150 amino acid residues, or about 50–110 amino acid residues and has at least about 60%, 70% 80% 90% 95%, 99%, or 100% homology with a "PH domain," e.g., the PH domain of human 32544 (e.g., residues 44–151 of SEQ ID NO:2).

A 32544 polypeptide can also include a "phosphatidylinositol-specific phospholipase C domain X (referred to herein as "PLC-X domain")" or regions homologous with a "PLC-X domain". As used herein, the term "PLC-X domain" refers to a protein domain having an amino acid sequence of about 8 to 200, preferably about 15 to 170, more preferably about 145 amino acid residues. By "PLC-X domain" is meant a subdomain that composes the catalytic site of the phospholipase, e.g., PLC-X subdomain can fold together with another subdomain, e.g., phosphatidylinositol-specific phospholipase C domain Y such that a functioning catalytic site that hydrolyzes a phosphatidylinositol is formed, e.g., phosphatidylinositol 4, 5-bisphosphate, is formed.

The "PLC-X domain" includes an amino acid sequence of about 145 amino acid residues in length and can have a bit score for the alignment of the sequence to the phosphatidylinositol-specific phospholipase-C domain X (HMM) of at least 50. Preferably, a PLC-X domain includes at least about 15–170 amino acids, or at least about 20–150, or about 145 amino acids and has a bit score for the alignment of the sequence to the phosphatidylinositol-specific phospholipase-C domain X (HMM) of at least 60, 70, 80, 90, 100, 150, 200, 250, or greater. An alignment of the PLC-X domain (amino acids 323 to 468 of SEQ ID NO:2) of human 32544 with a consensus amino acid sequence derived from a hidden Markov model is depicted in FIG. 5.

In a preferred embodiment, the 32544 polypeptide or protein has a "PLC-X" or a region which includes at least about 8–200, more preferably about 15–170 or 20–150 amino acid residues and has at least about 60%, 70% 80% 90% 95%, 99%, or 100% homology with a "PLC-X domain," e.g., the PLC-X domain of human 32544 (e.g., residues 323–468 of SEQ ID NO:2).

A 32544 polypeptide can include a "phosphatidylinositol-specific phospholipase C domain Y (referred to herein as PLC-Y domain)" or regions homologous with a "PLC-Y domain". As used herein, the term "PLC-Y domain" refers to a protein domain having an amino acid sequence of about 8 to 200, preferably about 15 to 170, more preferably about 117 amino acid residues. By "PLC-Y domain" is meant a subdomain that composes the catalytic site of the phospholipase, e.g., the subdomain can fold together with another subdomain, e.g., PLC-X domain such that a functioning catalytic site that hydrolyzes a phosphatidylinositol, e.g., phosphatidylinositol 4, 5-bisphosphate, is formed.

The "PLC-Y domain" includes an amino acid sequence of about 117 amino acid residues in length and can have a bit score for the alignment of the sequence to the PLC-Y domain (HMM) of at least 50. Preferably, a PLC-Y domain includes at least about 15–170 amino acids, or at least about 20–150, or about 117 amino acids and has a bit score for the alignment of the sequence to the PLC-Y domain (HMM) of at least 60, 70, 80, 90, 100, 110, 120, 140, 160, 180, or greater. An alignment of the PLC-Y domain (amino acids 621 to 736 of SEQ ID NO:2) of human 32544 with a consensus amino acid sequence derived from a hidden Markov model is depicted in FIG. 6.

In a preferred embodiment 32544 polypeptide or protein has a "PLC-Y domain" or a region which includes at least about 8–200, more preferably about 15–170 or 20–150 amino acid residues and has at least about 60%, 70% 80% 90% 95%, 99%, or 100% homology with a "PLC-Y domain" e.g., PLC-Y domain of human 32544 (e.g., residues 621–736 of SEQ ID NO:2).

A 32544 polypeptide can include a "calcium (Ca2+) binding domain (referred to as "C2 domain") or regions homologous with a "C2 domain". As used herein, the term "C2 domain" refers to a protein domain having an amino acid sequence of about 8 to 200, preferably about 15 to 170, more preferably about 20 to 100, or still more preferably about 90 amino acid residues. By "C2 domain" is meant a domain that can mediate interaction with calcium or phospholipids.

The "C2 domain" includes an amino acid sequence of about 90 amino acid residues in length and can have a bit score for the alignment of the sequence to the phosphatidylinositol-specific phospholipase-C domain Y (HMM) of at least 50. Preferably, a C2 domain includes at least about 8–200, or at least about 15–170, or at least 20–100, or about 90 amino acids and has a bit score for the alignment of the sequence to the C2 domain (HMM) of at least 60, 70, 80, 85, or greater. An alignment of the C2 domain (amino acids 756 to 848 of SEQ ID NO:2) of human 32544 with a consensus amino acid sequence derived from a hidden Markov model is depicted in FIG. 7.

In a preferred embodiment, a 32544 polypeptide or protein has a "C2 domain" or a region which includes at least about 10–200, more preferably about 15–170 or 20–100 amino acid residues and has at least about 60%, 70% 80% 90% 95%, 99%, or 100% homology with a "C2 domain," e.g., the C2 domain of human 32544 (e.g., residues 756–848 of SEQ ID NO:2).

To identify the presence of a "PH" domain, "PLC-X domain," "PLC-Y domain," or a "C2" domain in a 32544 protein sequence, and make the determination that a polypeptide or protein of interest has a particular profile, the amino acid sequence of the protein can be searched against a database of HMMs (e.g., the Pfam database, release 2.1) using the default parameters (www.sanger.ac.uk/Software/Pfam/HMM_search). For example, the hmmsf program, which is available as part of the HMMER package of search programs, is a family specific default program for MIL-PAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al.(1990) *Meth. Enzymol.* 183:146–159; Gribskov et al.(1987) *Proc. Natl. Acad. Sci. USA* 84:4355–4358; Krogh et al.(1994) *J. Mol. Biol.* 235:1501–1531; and Stultz et al.(1993) *Protein Sci.* 2:305–314, the contents of which are incorporated herein by reference. A search was performed against the HMM database resulting in the identification of a "PH domain" domain in the amino acid sequence of human 32544 at about residues 44–151 of SEQ ID NO:2 (see FIG. 3); a "C2 domain" in the amino acid sequence of human 32544 at about residues 756–848 of SEQ ID NO:2 (see FIG. 7); an EF hand domain in the amino acid sequence of human 32544 at about residues 169 to 197 of SEQ. ID. NO:2 (see FIG. 4); a "PLC-Y domain" in the amino acid sequence of human 32544 at about residues 621–736 of SEQ ID NO:2 (see FIG. 6); and a "PLC-X domain" in the amino acid sequence of human 32544 at about residues 323–468 of SEQ ID NO:2 (see FIG. 5).

To identify the presence of a "phospholipase" domain such as a PI-PLC-X domain in a 32544 protein sequence, and make the determination that a polypeptide or protein of interest has a particular profile, the amino acid sequence of the protein can be searched against a database of domains, e.g., the ProDom database (Corpet et al. (1999), *Nucl. Acids Res.* 27:263–267). The ProDom protein domain database consists of an automatic compilation of homologous domains. Current versions of ProDom are built using recursive PSI-BLAST searches (Altschul SF et al. (1997) *Nucleic Acids Res.* 25:3389–3402; Gouzy et al. (1999) *Computers and Chemistry* 23:333–340) of the SWISS-PROT 38 and TREMBL protein databases. The database automatically generates a consensus sequence for each domain. A BLAST search was performed against the HMM database resulting in the identification of a phospholipase domain in the amino acid sequence of human 32544.

The phospholipase domain is homologous to ProDom family PD183899 ("KIAA0450" SEQ ID NO:10, Pro-Domain Release 2001.1; www.toulouse.inra.fr/prodom.html). An alignment of the phospholipase domain (amino acids 883 to 1207 of SEQ ID NO:2) of human 32544 with a consensus amino acid sequence (SEQ ID NO:10) derived from a hidden Markov model is depicted in FIG. 8. The consensus sequence for SEQ ID NO:8 is 77% identical over amino acids 883 to 1207 of SEQ ID NO:2 as shown in FIG. 8.

The phospholipase domain is homologous to ProDom family PD001214 ("phospholipase phosphodiesterase hydrolase phosphoinositide-specific 1-phosphatidylinositol-45-bisphosphate degradation tranducer lipid beta" SEQ ID NOs:11–13, ProDomain Release 2001.1; www.toulouse.inra.fr/prodom.html). An alignment of the phospholipase domain (amino acids 307 to 456, 514 to 562, and 742 to 759 of SEQ ID NO:2) of human 32544 with a consensus amino acid sequence (SEQ ID NO:10) derived from a hidden Markov model is depicted in FIG. 9. The consensus sequence for SEQ ID NO:11 is 55% identical over amino acids 307 to 456 of SEQ ID NO:2; the consensus sequence for SEQ ID NO:12 is 30% identical over amino acids 514 to 562 of SEQ ID NO:2; and the consensus sequence for SEQ ID NO:13 is 33% identical over amino acids 742 to 759 of SEQ ID NO:2 as shown in FIG. 9.

The phospholipase domain is homologous to ProDom family PD186804 ("phospholipase C delta calcium-binding PLC-III hydrolase phosphodiesterase lipid PLC-delta-1 1-phosphatidylinositol-45-bisphosphate" SEQ ID NO:14, ProDomain Release 2001.1; www.toulouse.inra.fr/prodom.html). An alignment of the phospholipase domain (amino acids 41 to 214 of SEQ ID NO:2) of human 32544 with a consensus amino acid sequence (SEQ ID NO:14) derived from a hidden Markov model is depicted in FIG. 10. The consensus sequence for SEQ ID NO:14 is 37% identical over amino acids 41 to 214 of SEQ ID NO:2 as shown in FIG. 10.

The phospholipase domain is homologous to ProDom family PD023751 ("phospholipase binding C KDA-INS145P3 K10F12.3" SEQ ID NO:15, ProDomain Release 2001.1; www.toulouse.inra.fr/prodom.html). An alignment of the phospholipase domain (amino acids 174 to 304 of SEQ ID NO:2) of human 32544 with a consensus amino acid sequence (SEQ ID NO:15) derived from a hidden Markov model is depicted in FIG. 11. The consensus sequence for SEQ ID NO:14 is 39% identical over amino acids 174 to 304 of SEQ ID NO:2 as shown in FIG. 11.

The phospholipase domain is homologous to ProDom family PD308221 ("FLJ12548 similar FIS cDNA phosphatidylinositol-45-bisphosphate NT2RM4000657 delta phosphodiesterase weakly 1-" SEQ ID NO:16, Pro-Domain Release 2001.1; www.toulouse.inra.fr/prodom.html). An alignment of the phospholipase domain (amino acids 851 to 944 of SEQ ID NO:2) of human 32544 with a consensus amino acid sequence (SEQ ID NO:15) derived from a hidden Markov model is depicted in FIG. 12. The consensus sequence for SEQ ID NO:16 is 39% identical over amino acids 851 to 944 of SEQ ID NO:2 as shown in FIG. 12.

An additional method to identify the presence of a "phospholipase" domain in a 32544 protein sequence, and make the determination that a polypeptide or protein of interest has a particular profile, the amino acid sequence of the protein can be searched against a SMART database (Simple Modular Architecture Research Tool, http://smart.embl-heidelberg.de/) of HMMs as described in Schultz et al. (1998), *Proc. Natl. Acad. Sci. USA* 95:5857 and Schultz et al. (2000) *Nucl. Acids Res* 28:231. The database contains domains identified by profiling with the hidden Markov models of the HMMer2 search program (R. Durbin et al. (1998) *Biological sequence analysis: probabilistic models of proteins and nucleic acids.* Cambridge University Press.; http://hmmer.wustl.edu/). The database also is extensively annotated and monitored by experts to enhance accuracy. A search was performed against the HMM database resulting in the identification of a "PH_update" domain in the amino acid sequence of human 32544 at about residues 44 to 153 of SEQ ID NO:2 (see FIG. 1); a "efh_1" domain in the amino acid sequence of human 32544 at about residues 169 to 197 and 205 to 234 of SEQ ID NO:2; a "plcx_3" domain in the amino acid sequence of human 32544 at about residues 322 to 467 of SEQ ID NO:2; a "plcy_3" domain in the amino acid sequence of human 32544 at about residues 622 to 736 of SEQ ID NO:2; and a "C2_3c" domain in the amino acid sequence of human 32544 at about residues 755 to 863 of SEQ ID NO:2.

A 32544 polypeptide can include at least one, two, and preferably three "transmembrane domains" or regions homologous with a "transmembrane domain". As used herein, the term "transmembrane domain" includes an amino acid sequence of about 10 to 40 amino acid residues in length and spans the plasma membrane. Transmembrane domains are rich in hydrophobic residues, e.g., at least 50%, 60%, 70%, 80%, 90%, 95% or more of the amino acids of a transmembrane domain are hydrophobic, e.g., leucines, isoleucines, tyrosines, or tryptophans. Transmembrane domains typically have alpha-helical structures and are described in, for example, Zagotta, W. N. et al., (1996) *Annual Rev. Neurosci.* 19:235–263, the contents of which are incorporated herein by reference.

In a preferred embodiment, a 32544 polypeptide or protein has at least one, two, and preferably three "transmembrane domains" or a region which includes at least about 12 to 35 more preferably about 15 to 30 or 15 to 25 amino acid residues and has at least about 60%, 70% 80% 90% 95%, 99%, or 100% homology with a "transmembrane domain," e.g., the transmembrane domains of human 32544 (e.g., residues 817 to 834,1153 to 1176, and 1183 to 1200 of SEQ ID NO:2). The transmembrane domains of human 32544 is visualized in the hydropathy plot (FIG. 2) as regions of about 15 to 25 amino acids where the hydropathy trace is mostly above the horizontal line.

To identify the presence of a "transmembrane" domain in a 32544 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) *Biochemistry* 33:3038–3049).

A 32544 polypeptide can include at least one, two, three, and preferably four "non-transmembrane regions." As used herein, the term "non-transmembrane region" includes an amino acid sequence not identified as a transmembrane domain. The non-transmembrane regions in 32544 are located at about amino acids 1 to 816, 835 to 1152, 1177 to 1182, and 1201 to 1207 of SEQ ID NO:2.

The non-transmembrane regions of 32544 include at least one, and preferably two cytoplasmic regions. When located at the N-terminus, the cytoplasmic region is referred to herein as the "N-terminal cytoplasmic domain." As used herein, an "N-terminal cytoplasmic domain" includes an amino acid sequence having about 1 to 1000, preferably about 1 to 900, more preferably about 1 to 850, or even more preferably about 1 to 816 amino acid residues in length and is located inside of a cell or within the cytoplasm of a cell. The C-terminal amino acid residue of an "N-terminal cytoplasmic domain" is adjacent to an N-terminal amino acid residue of a transmembrane domain in a 32544 protein. For example, an N-terminal cytoplasmic domain is located at about amino acid residues 1 to 816 of SEQ ID NO:2.

In a preferred embodiment, a polypeptide or protein has an N-terminal cytoplasmic domain or a region which includes at least about 5, preferably about 1 to 1000, and more preferably about 1 to 850 amino acid residues and has at least about 60%, 70% 80% 90% 95%, 99%, or 100% homology with an "N-terminal cytoplasmic domain," e.g., the N-terminal cytoplasmic domain of human 32544 (e.g., residues 1 to 816 of SEQ ID NO:2).

In another embodiment, a 32544 protein includes at least one cytoplasmic loop. As used herein, the term "loop" includes an amino acid sequence that resides outside of a phospholipid membrane, having a length of at least about 4, preferably about 5 to 10, more preferably about 6 to 8 amino acid residues, and has an amino acid sequence that connects two transmembrane domains within a protein or polypeptide. Accordingly, the N-terminal amino acid of a loop is adjacent to a C-terminal amino acid of a transmembrane domain in a 32544 molecule, and the C-terminal amino acid of a loop is adjacent to an N-terminal amino acid of a transmembrane domain in a 32544 molecule. As used herein, a "cytoplasmic loop" includes a loop located inside of a cell or within the cytoplasm of a cell. For example, a "cytoplasmic loop" can be found at about amino acid residues 1177 to 1182 of SEQ ID NO:2.

In a preferred embodiment, a 32544 polypeptide or protein has a cytoplasmic loop or a region which includes at least about 4, preferably about 5 to 10, and more preferably about 6 to 8 amino acid residues and has at least about 60%, 70% 80% 90% 95%, 99%, or 100% homology with a cytoplasmic loop," e.g., a cytoplasmic loop of human 32544 (e.g., residues 1177 to 1182 of SEQ ID NO:2).

The non-transmembrane regions of 32544 also include at least one, and preferably two, non-cytoplasmic regions. When located at the C-terminus, the non-cytoplasmic region is referred to herein as the "C-terminal non-cytoplasmic domain." As used herein, a "C-terminal non-cytoplasmic domain" includes an amino acid sequence having about 1 to 10, preferably about 1 to 9, more preferably about 1 to 8, or even more preferably about 1 to 7 amino acid residues in length and is located outside of a cell. The N-terminal amino acid residue of an "C-terminal non-cytoplasmic domain" is adjacent to a C-terminal amino acid residue of a transmembrane domain in a 32544 protein. For example, a C-terminal non-cytoplasmic domain is located at about amino acid residues 1201 to 1207 of SEQ ID NO:2.

In a preferred embodiment, a polypeptide or protein has a C-terminal non-cytoplasmic domain or a region which includes at least about 5, preferably about 1 to 10, and more preferably about 1 to 7 amino acid residues and has at least about 60%, 70% 80% 90% 95%, 99%, or 100% homology with a "C-terminal non-cytoplasmic domain," e.g., the C-terminal cytoplasmic domain of human 32544 (e.g., residues 1201 to 1207 of SEQ ID NO:2).

In another embodiment, a 32544 protein includes at least one non-cytoplasmic loop. As used herein, a "non-cytoplasmic loop" includes an amino acid sequence located outside of a cell or within an intracellular organelle. Non-cytoplasmic loops include extracellular domains (i.e., outside of the cell) and intracellular domains (i.e., within the cell). When referring to membrane-bound proteins found in intracellular organelles (e.g., mitochondria, endoplasmic reticulum, peroxisomes microsomes, vesicles, endosomes, and lysosomes), non-cytoplasmic loops include those domains of the protein that reside in the lumen of the organelle or the matrix or the intermembrane space. For example, a "non-cytoplasmic loop" can be found at about amino acid residues 835 to 1152 of SEQ ID NO:2.

In a preferred embodiment, a 32544 polypeptide or protein has at least one non-cytoplasmic loop or a region which includes at least about 4, preferably about 5 to 350, more preferably about 6 to 319 amino acid residues and has at least about 60%, 70% 80% 90% 95%, 99%, or 100% homology with a "non-cytoplasmic loop," e.g., at least one non-cytoplasmic loop of human 32544 (e.g., residues 835 to 1152 of SEQ ID NO:2).

A 32544 family member can include at least one PI-PLC-X domain, at least one PI-PLC-Y domain, at least one C2 domain, at least one, preferably two EF hand domains, at least one PH domain domain; and at least one two, three, four, five, six and preferably seven transmembrane or non-transmembrane domains. Furthermore, a 32544 family member can include at least one tyrosine kinase phosphorylation site (PS00007); at least one, two, preferably three amidation sites (PS00009); at least one EF-hand calcium-binding domain (PS000018); at least one, two, three, preferably four N-glycosylation sites (PS00001); at least one cAMP- and cGMP-dependent protein kinase phosphorylation site (PS00004); at least one, two, three, four, five, six, seven, eight, nine, ten, eleven, twelve, thirteen, fourteen, fifteen, sixteen and preferably seventeen protein kinase C sites (PS00005); and at least one, two, three, four, five, six, seven, eight, nine, ten, eleven, twelve, thirteen, fourteen, fifteen, sixteen, seventeen and preferably eighteen casein kinase II phosphorylation sites (PS00006).

As the 32544 polypeptides of the invention may modulate 32544-mediated activities, they may be useful as of for developing novel diagnostic and therapeutic agents for 32544-mediated or related disorders, as described below. As used herein, a "32544 activity", "biological activity of 32544" or "functional activity of 32544", refers to an activity exerted by a 32544 protein, polypeptide or nucleic acid molecule on e.g., a 32544-responsive cell or on a 32544 substrate, e.g., a protein substrate, as determined in vivo or in vitro. In one embodiment, a 32544 activity is a direct activity, such as an association with a 32544 target molecule. A "target molecule" or "binding partner" is a molecule with which a 32544 protein binds or interacts with in nature. In an exemplary embodiment, it is a receptor, e.g., a tyrosine kinase receptor. In another embodiment, 32544 can associate with a second messenger molecule such as a specialized adaptor molecule; with inositol phosphates and inositol lipids; membrane proteins; or with a guanine nucleotide binding-regulatory protein (G-protein). A 32544 activity can also be an indirect activity, e.g., a cellular signaling activity mediated by interaction of the 32544 protein with a receptor or another signaling molecule. For example, the 32544 proteins of the present invention can have one or more of the following activities: (1) transduction of transmembrane signals; (2) lipid-metabolizing activity, e.g., 32544 can catalyze the hydrolysis of phosphatidyl-inositol-4,5-bisphophate (PIP2) producing diacylglycerol and inositol 1,4,5-trisphophate; (3) the regulation of transmission of signals from cellular receptors such as hormones such as serotonin, growth factors such as platelet-derived growth factor (PDGF), fibroblast growth factor (FGF), and nerve growth factor (NGF), neurotransmitters and immunoglobulins; (4) modulation of cell proliferation; (5) modulation of cell differenciation; (6) modulation of cell migration; (7) modulation of fertilization; (8) modulation of hypertension; (9) treatment of pain; and (10) the ability to antagonize or inhibit, competitively or non-competitively, any of 1–9.

Based on the above-described sequence similarities, the 32544 molecules of the present invention are predicted to have similar biological activities as members of the PLC family. Members of the PLC family play a very important role in transmembrane signal transduction. Extracellular signaling molecules including hormones, growth factors, neurotransmitters, and immunoglobulins bind to their respective cell surface receptors and activate phospholipase-C. PLC molecules have many functions including: glycogenolysis in liver cells, histamine secretion by mast cells, serotonin release by blood platelets, aggregation by blood platelets, insulin release by pancreatic islet cells, epinephrine secretion by adrenal chromaffin cells, and smooth muscle contraction. In general, biological systems that are activated by receptor tyrosine kinase cause the activation of phospholipase-C. The role of an activated PLC is to catalyze the hydrolysis of phosphatidyl-inositol-4,5-bisphosphate (PIP2), a minor component of the plasma membrane, to produce diacylglycerol and inositol 1,4,5-trisphosphate (IP3). Inositol trisphosphate releases calcium from intracellular stores and increases the influx of calcium from the extracellular fluid. The calcium ions directly regulate target enzymes and indirectly affect other enzymes by functioning as a second messenger and interacting with calcium-binding proteins, such as troponin C and calmodulin. For example, calcium ions regulate muscle contraction, glycogen breakdown and exocytosis. Diacylglycerol, a product of the hydrolysis by PLCs, acts as a second messenger by activating protein kinase C. Activated protein kinase C phosphorylates a great number of intracellular proteins at the serine and threonine residues and modulates different signaling pathways. For example, the phosphorylation of glycogen synthase by protein kinase C stops the synthesis of glycogen. Moreover, protein kinase C controls cell division and proliferation. Both pathways are part of transmembrane signal transduction mechanisms, which regulate cellular processes, which include secretion, neural activity, metabolism, differenciation and proliferation.

Thus, the 32544 molecules can act as novel diagnostic targets and therapeutic agents for controlling disorders caused by abnormal or aberrant PLC activity. Evidence indicates that a high percentage of primary human mammary carcinomas concomitantly show abnormally high levels of PLC-gamma-1 (Kassis et al., *Clin Cancer Res.*, Aug;5(8) :2251–60, 1999). Likewise, studies on spontaneous hypertensive rats have suggested that one of the main causes for the hypertension is an abnormal activation of PLC-delta-1 resulting from point mutations in the X and Y regions of the PLC amino acid sequence (Sanada et al., *Hypertension* 33(4):1036–42, 1999). Therefore, the 32544 molecules can act as novel diagnostic targets and therapeutic agents for controlling one or more of cellular proliferative and/or differentiative disorders, disorders associated with bone metabolism, immune disorders, hematopoietic disorders, cardiovascular disorders, liver disorders, viral diseases, pain or metabolic disorders.

Further, it has been shown that the activation of PLC-delta isozymes, a member of phosphoinositide-specific phospholipase C family, may occur as an event secondary to the receptor-mediated activation of other PLC isozymes or calcium channels. More recently, it has been also shown that phospholipase C-delta 1 is activated upon bradykinin stimulation. In this situation it appears that PLC-delta 1 is activated by capacitative calcium entry occurring subsequent to IP3 production and calcium release after PLC-beta activation. This regulation of PLC-delta 1 has an important meaning since it may represent a positive feedback mechanism in that the signaling mediated by PLC-beta linked receptors can be potentiated and prolonged. In addition, the activation of PLC-delat 1 after bradykinin stimulation is associated with ah increase in intracellular calcium leading to the potentiation of norepinephrine (the main neurotransmitter in sympathetic neurons) secretion. Furthermore, expression of PLC-delta 1 increases in neurons after glutamate treatment. This increase can be prevented by removal of extracellular calcium, NMDA antagonist or NO synthase inhibitor.

Phospholipase C-delta 1 appears to be an important mediator in the signaling pathways of hyperlagesic agents, like bradykinin, and glutamate, one of the main neurotransmiters in the spinal cord involved in nociceptive transmission. Furthermore, phospholipase C-delta 1 induces release of a sympathetic neurotransmitter that has been involved in maintenance of some types of pain states. Thus, antagonizing 32544 may be beneficial for the treatment of pain.

As used herein, a "phospholipase family-associated disorder" includes a disorder, disease or condition which is caused or characterized by a misregulation (e.g., downregulation or upregulation) of a phospholipase family-mediated activity. Phospholipase family-associated disorders can detrimentally affect cellular functions such as cellular proliferation, growth, differentiation, or migration, cellular regulation of homeostasis, inter- or intra-cellular communication; tissue function, such as cardiac function or musculoskeletal function; systemic responses in an organism, such as nervous system responses, hormonal responses (e.g., insulin response), or immune responses; and protection of cells from toxic compounds (e.g., carcinogens, toxins, mutagens, and toxic byproducts of metabolic activity (e.g., reactive oxygen species)). Accordingly, 32544 protein may mediate various disorders, including cellular proliferative and/or differentiative disorders, hormonal disorders, immune disorders, brain disorders, heart disorders, blood vessel disorders, platelet disorders or pain or metabolic disorders. As the 32544 polypeptides of the invention may modulate 32544-mediated activities, they may be useful for developing novel diagnostic and therapeutic agents for 32544-mediated or related disorders, as described below.

Phospholipase-family proteins are key molecules involved in signal transduction through the hydrolysis of phosphatidylinositol into inositol 1,4,5-trisphosphate and diacylglycerol. Abnormalities in neurotransmitter signalling coupled to phosphatidylinositol-specific phospholipase have been reported in brain tissue from patients with schizophrenia. The regulation of phospholipase in different regions of the brain result in increased enzyme levels in some regions and decreased enzyme levels in other regions. Due to the activity of phospholipase in response to G-protein-coupled receptors by neuroendocrine growth factors, phosphatidylinositol specific phospholipase has also been suggested to be involved in small cell lung carcinoma and non-small cell lung carcinoma proliferation. The 32544 polypeptides share a common domain with known phospholipase-family members and is expected to have similar effects in cellular metabolism. Accordingly, 32544 may play a role in signal transduction and alteration of neurotransmitter signalling and thus the 32544 compositions of the invention (e.g., nucleic acids, polypeptides, proteins, antibodies) can be used to modulate cellular immune response, and furthermore can be used in screening assays to identify agents for modulating cellular signal transduction, as well as in detection or diagnostic assays to identify conditions such as schizophrenia, small cell lung carcinoma and non-small cell lung carcinoma.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genitourinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 32544 nucleic acid and protein of the invention can be used to monitor, treat and/or diagnose a variety of proliferative disorders. E.g., such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L., (1991) Crit. Rev. in Oncol./Hemotol. 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Phospholipase family-associated or related disorders also include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

Phospholipase family-associated or related disorders also include immune disorders, such as autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, *Herpes simplex virus Type 2, Varicella-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Additionally, 32544 may play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L., (1987) *Pain*, New York:McGraw-Hill); pain associated with muscoloskeletal disorders, e.g., joint pain; tooth pain; headaches; pain associated with surgery; pain related to irritable bowel syndrome; or chest pain.

The 32544 protein, fragments thereof, and derivatives and other variants of the sequence in SEQ ID NO:2 are collectively referred to as "polypeptides or proteins of the invention" or "32544 polypeptides or proteins". Nucleic acid molecules encoding such polypeptides or proteins are collectively referred to as "nucleic acids of the invention" or "32544 nucleic acids."32544 molecules refer to 32544 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1–6.3.6. Aqueous and nonaqueous methods are described in that reference and either can be used. A preferred, example of stringent hybridization conditions are hybridization in 6×sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions are hybridization in 6×sodium chloride/sodium citrate (SSC) at about 45° C., followed by one or more washes in 0.2×SSC, 0.1% SDS at 60° C. Preferably, stringent hybridization conditions are hybridization in 6×sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1, or SEQ ID NO:3, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 32544 protein, preferably a mammalian 32544 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 32544 protein having less than about 30%, 20%, 10% and more preferably 5% (by dry weight), of non-32544 protein (also referred to herein as a "contaminating protein"), or of chemical precursors or non-32544 chemicals. When the 32544 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 32544 (e.g., the sequence of SEQ ID NO:1 or SEQ ID NO:3 without abolishing or more preferably, without substantially altering a biological activity, whereas an "essential" amino acid residue results in such a change. For example, amino acid residues that are conserved among the polypeptides of the present invention, e.g., those present in the phospholipase family domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 32544 protein is preferably replaced with another amino acid residue from the same side chain family. Alternatively, in another embodiment, mutations can be introduced randomly along all or part of a 32544 coding sequence, such as by saturation mutagenesis, and the resultant mutants can be screened for 32544 biological activity to identify mutants that retain activity. Following mutagenesis of SEQ ID NO:1 or SEQ ID NO:3, the encoded protein can be expressed recombinantly and the activity of the protein can be determined.

As used herein, a "biologically active portion" of a 32544 protein includes a fragment of a 32544 protein which participates in an interaction between a 32544 molecule and a non-32544 molecule. Biologically active portions of a 32544 protein include peptides comprising amino acid sequences sufficiently homologous to or derived from the amino acid sequence of the 32544 protein, e.g., the amino acid sequence shown in SEQ ID NO:2, which include less amino acids than the full length 32544 proteins, and exhibit at least one activity of a 32544 protein. Typically, biologically active portions comprise a domain or motif with at least one activity of the 32544 protein, e.g., (1) transmembrane signal transduction; (2) lipid-metabolizing activity, e.g., 32544 can catalyze the hydrolysis of phosphatidylinositol-4,5-bisphosphate (PIP2) producing diacylglycerol and inositol 1,4,5-trisphosphate; (3) the regulation of transmission of signals from cellular receptors, e.g., hormones, growth factors, neurotransmitters and immunoglobulins; (4) modulation of cell proliferation; (5) modulation of cell differenciation; (6) modulation of cell migration; (7) modulation of fertilization; and (8) modulation of hypertension. A biologically active portion of a 32544 protein can be a polypeptide which is, for example, 10, 25, 50, 100, 200 or more amino acids in length. Biologically active portions of a 32544 protein can be used as targets for developing agents which modulate a 32544 mediated activity, e.g., phospholipase family activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 32544 amino acid sequence of SEQ ID NO:2 having 1207 amino acid residues, at least 362, preferably at least 483, more preferably at least 604, even more preferably at least 724, and even more preferably at least 845, 966 or 1086 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990) *J. Mol. Biol.* 215:403–10. BLAST nucleotide searches can be performed with the NBLAST program, score =100, wordlength=12 to obtain nucleotide sequences homologous to 32544 nucleic acid molecules of the invention. BLAST protein searches can be performed with the XBLAST program, score=50, wordlength=3 to obtain amino acid sequences homologous to 32544 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See www.ncbi.nlm.nih.gov.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 32544 polypeptide described herein, e.g., a full length 32544 protein or a fragment thereof, e.g., a biologically active portion of 32544 protein. Also included is a nucleic acid fragment suitable for use as a hybridization probe, which can be used, e.g., to a identify nucleic acid molecule encoding a polypeptide of the invention, 32544 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of these nucleotide sequences. In one embodiment, the nucleic acid molecule includes sequences encoding the human 32544 protein (i.e., "the coding region", from nucleotides 435–4055 of SEQ ID NO:1, not including the terminal codon), as well as 5' untranslated sequences (nucleotides 1–434 of SEQ ID NO:1). Alternatively, the nucleic acid molecule can include only the coding region of SEQ ID NO:1 (e.g., nucleotides 435–4055 of SEQ ID NO:1, corresponding to SEQ ID NO:3) and, e.g., no flanking sequences which normally accompany the subject sequence. In another embodiment, the nucleic acid molecule encodes a sequence corresponding to the mature protein of SEQ ID NO:2.

In another embodiment, an isolated nucleic acid molecule of the invention includes a nucleic acid molecule which is a complement of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3 such that it can hybridize to the nucleotide sequence shown in SEQ ID NO:1 or SEQ ID NO:3, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the nucleotide sequence shown in SEQ ID NO:1 or SEQ ID NO:3. In the case of an isolated nucleic acid molecule which is longer than or equivalent in length to the reference sequence, e.g., SEQ ID NO:1, or SEQ ID NO:3, the comparison is made with the full length of the reference sequence. Where the isolated nucleic acid molecule is shorter than the reference sequence, e.g., shorter than SEQ ID NO:1, or SEQ ID NO:3, the comparison is made to a segment of the reference sequence of the same length (excluding any loop required by the homology calculation).

32544 Nucleic Acid Fragments

A nucleic acid molecule of the invention can include only a portion of the nucleic acid sequence of SEQ ID NO:1 or SEQ ID NO:3. For example, such a nucleic acid molecule can include a fragment which can be used as a probe or primer or a fragment encoding a portion of a 32544 protein, e.g., an immunogenic or biologically active portion of a 32544 protein. A fragment can comprise e.g., nucleotides 275 to 598 of SEQ ID NO:1, which encodes a PH domain of human 32544; nucleotides 1112 to 1549 of SEQ ID NO:1, which encodes the PLC-X domain of human 32544; or nucleotides 2006 to 2353 of SEQ ID NO:1, which encodes the PLC-Y domain of human 32544. The nucleotide sequence determined from the cloning of the 32544 gene allows for the generation of probes and primers designed for use in identifying and/or cloning other 32544 family members, or fragments thereof, as well as 32544 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include a PH domain and a C2 domain. In a preferred embodiment the fragment is at least, 50, 100, 200, 300, 400, 500, 600, 700, or 900 base pairs in length. 32544 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: PH domain (from about amino acids 44–151 of SEQ ID NO:2); a PLC-X domain (from about amino acids 323–468 of SEQ ID NO:2); a PLC-Y domain (from about amino acids 621–736 of SEQ ID NO:2); or a C2 domain (from about amino acids 756–848 of SEQ ID NO:2). In another embodiment a set of primers is provided, e.g., primers suitable for use in a PCR, which can be used to amplify a selected region of a 32544 sequence. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying a domain or region described herein are provided, e.g., all or a portion of any of the following regions: a PLC-X domain (from about amino acids 323–468 of SEQ ID NO:2), a PLC-Y (from about amino acids 621–736 of SEQ ID NO:2), a C2 domain (from about amino acids 756–848 of SEQ ID NO:2), or a PH domain (from about amino acids 44–151 of SEQ ID NO:2).

In another embodiment a set of primers is provided, e.g., primers suitable for use in a PCR, which can be used to amplify a selected region of a 32544 sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of the following regions are provided: a phospholipase family domain (e.g., about nucleotides 1401–1838 of SEQ ID NO:1).

A nucleic acid fragment can encode an epitope bearing region of a polypeptide described herein.

A nucleic acid fragment encoding a "biologically active portion of a 32544 polypeptide" can be prepared by isolating a portion of the nucleotide sequence of SEQ ID NO:1 or SEQ ID NO:3, which encodes a polypeptide having a 32544 biological activity (e.g., the biological activities of the 32544 proteins as described herein), expressing the encoded portion of the 32544 protein (e.g., by recombinant expression in vitro) and assessing the activity of the encoded portion of the 32544 protein. For example, a nucleic acid fragment encoding a biologically active portion of 32544 includes a phospholipase family domain (e.g., about nucleotides 1401–1838 of SEQ ID NO:1). A nucleic acid fragment encoding a biologically active portion of a 32544 polypeptide, may comprise a nucleotide sequence which is greater than 300–1200 or more nucleotides in length.

In preferred embodiments, nucleic acids include a nucleotide sequence which is about 300, 400, 500, 600, 700, 800, 900, 1000, 1100, 1200 nucleotides in length and hybridizes under stringent hybridization conditions to a nucleic acid molecule of SEQ ID NO:1 or SEQ ID NO:3.

32544 Nucleic Acid Variants

The invention further encompasses nucleic acid molecules that differ from the nucleotide sequence shown in SEQ ID NO:1 or SEQ ID NO:3. Such differences can be due to degeneracy of the genetic code (and result in a nucleic acid which encodes the same 32544 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non preferred, for a particular expression system. E.g., the nucleic acid can be one in which at least one colon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1 or SEQ ID NO:3, e.g., as follows: by at least one but less than 10, 20, 30, or 40 nucleotides; at least one but less than 1%, 5%, 10% or 20% of the in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:2 or a fragment of this sequence. Such nucleic acid molecules can readily be obtained as being able to hybridize under stringent conditions, to the nucleotide sequence shown in SEQ ID NO:3 or a fragment of this sequence. Nucleic acid molecules corresponding to orthologs, homologs, and allelic variants of the 32544 cDNAs of the invention can further be isolated by mapping to the same chromosome or locus as the 32544 gene. Preferred variants include those that are correlated with phospholipase family activity.

Allelic variants of 32544, e.g., human 32544, include both functional and non-functional proteins. Functional allelic variants are naturally occurring amino acid sequence variants of the 32544 protein within a population that maintain the ability to function similar to the 32544 protein, e.g., to hydrolyze phosphatidylinositol 4,5-bisphosphate to produce inositol 1,4,5-trisphosphate and diacylglycerol.

Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 32544, e.g., human 32544, protein within a population that do not have the ability to hydrolyze phosphatidylinositol. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 32544 family members and, thus, which have a nucleotide sequence which differs from the 32544 sequences of SEQ ID NO:1 or SEQ ID NO:3 are intended to be within the scope of the invention.

Antisense Nucleic Acid Molecules, Ribozymes and Modified 32544 Nucleic Acid Molecules In another aspect, the invention features, an isolated nucleic acid molecule which is antisense to 32544. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 32544 coding strand, or to only a portion thereof (e.g., the coding region of human 32544 corresponding to SEQ ID NO:3). In another embodiment, the antisense nucleic acid molecule is antisense to a "non-coding region" of the coding strand of a nucleotide sequence encoding 32544 (e.g., the 5' and 3' untranslated regions).

An antisense nucleic acid can be designed such that it is complementary to the entire coding region of 32544 mRNA, but more preferably is an oligonucleotide which is antisense to only a portion of the coding or noncoding region of 32544 mRNA. For example, the antisense oligonucleotide can be complementary to the region surrounding the translation start site of 32544 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 32544 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., (1987) *Nucleic Acids. Res.* 15:6625–6641). The antisense nucleic acid molecule can also comprise a 2'-o-methylribonucleotide (Inoue et al., (1987) *Nucleic Acids Res.* 15:6131–6148) or a chimeric RNA-DNA analogue (Inoue et al., (1987) *FEBS Lett.* 215:327–330).

In still another embodiment, an antisense nucleic acid of the invention is a ribozyme. A ribozyme having specificity for a 32544-encoding nucleic acid can include one or more sequences complementary to the nucleotide sequence of a 32544 cDNA disclosed herein (i.e., SEQ ID NO:1, or SEQ ID NO:3), and a sequence having known catalytic sequence responsible for mRNA cleavage (see U.S. Pat. No. 5,093,246 or Haseloff and Gerlach, (1988) *Nature* 334:585–591). For example, a derivative of a Tetrahymena L-19 IVS RNA can be constructed in which the nucleotide sequence of the active site is complementary to the nucleotide sequence to be cleaved in a 32544-encoding mRNA. See, e.g., Cech et al. U.S. Pat. No. 4,987,071; and Cech et al. U.S. Pat. No. 5,116,742. Alternatively, 32544 mRNA can be used to select a catalytic RNA having a specific ribonuclease activity from a pool of RNA molecules. See, e.g., Bartel, D. and Szostak, J. W. (1993) *Science* 261:1411–1418.

32544 gene expression can be inhibited by targeting nucleotide sequences complementary to the regulatory region of the 32544 (e.g., the 32544 promoter and/or enhancers) to form triple helical structures that prevent transcription of the 32544 gene in target cells. See generally, Helene, C., (1991) *Anticancer Drug Des.* 6(6):569–84; Helene, C. et al., (1992) *Ann. NY Acad. Sci.* 660:27–36; and Maher, L. J., (1992) *Bioassays* 14(12):807–15. The potential sequences that can be targeted for triple helix formation can be increased by creating a so-called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemmiluminescent, fluorescent, radioactive, or colorimetric.

A 32544 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al., (1996) *Bioorganic & Medicinal Chemistry* 4 (1): 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al., (1996) supra; Perry-O'Keefe et al., *Proc. Natl. Acad. Sci.* 93: 14670–675.

PNAs of 32544 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 32544 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B., (1996) supra)); or as probes or primers for DNA sequencing or hybridization (Hyrup B. et al., (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al., (1989) *Proc. Natl. Acad. Sci. USA* 86:6553–6556; Lemaitre et al., (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al., (1988) *Bio-Techniques* 6:958–976) or intercalating agents. (See, e.g., Zon, (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 32544 nucleic acid of the invention, two complementary regions one having a fluorophore and one a quencher such that the molecular beacon is useful for quantitating the presence of the 32544 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. 5,876,930.

Isolated 32544 Polypeptides

In another aspect, the invention features, an isolated 32544 protein, or fragment, e.g., a biologically active portion, for use as immunogens or antigens to raise or test (or more generally to bind) anti-32544 antibodies. 32544 protein can be isolated from cells or tissue sources using standard protein purification techniques. 32544 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., gylcosylation or cleavage, present when expressed in a native cell.

In a preferred embodiment, a 32544 polypeptide has one or more of the following characteristics:

(i) it has the ability to promote the hydrolysis of a phosphatidylinositol;

(ii) it has the ability to promote the transduction of transmembrane signals;

(iii) it has lipid-metabolizing activity, e.g., 32544 can catalyze the hydrolysis of phosphatidyl-inositol-4,5-bisphophate (PIP2) producing diacylglycerol and inositol 1,4,5-trisphosphate;

(iv) it has the ability to regulate the transmission of signals from cellular receptors such as hormones such as serotonin, growth factors such as platelet-derived growth factor (PDGF), fibroblast growth factor (FGF), and nerve growth factor (NGF), neurotransmitters and immunoglobulins;

(v) it has the ability to modulate cell proliferation;

(vi) it has the ability to modulate cell differenciation;

(vii) it has the ability to modulate cell migration;

(viii) it has the ability to modulate fertilization;

(ix) it has the ability to modulate hypertension;

(x) it has the ability to treat pain;

(xi) it has a molecular weight (e.g., deduced molecular weight), amino acid composition or other physical characteristic of 32544 of SEQ ID NO:2;

(xii) it has an overall sequence similarity of at least 60%, more preferably at least 70, 80, 90, or 95%, with a polypeptide of SEQ ID NO:2;

(xiii) it has a PH domain which is preferably about 70%, 80%, 90% or 95% identical to amino acid residues 44–151 of SEQ ID NO:2;

(xiv) it has a PLC-X domain which is preferably about 70%, 80%, 90% or 95% identical to amino acid residues 323–468 of SEQ ID NO:2;

(xv) it has a PLC-Y domain which is preferably about 70%, 80%, 90% or 95% identical to amino acid residues 621–736 of SEQ ID NO:2;

(xvi) it has a C2 domain which is preferably about 70%, 80%, 90% or 95% identical to amino acid residues 756–848 of SEQ ID NO:2; or (xvii) it has at least 70%, preferably 80%, and most preferably 90% identity to the cysteines found amino acid sequence of the native protein.

In a preferred embodiment the 32544 protein, or fragment thereof, differs from the corresponding sequence in SEQ ID NO:2. In one embodiment, it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. The differences are, preferably, differences or changes at a non essential residue or a conservative substitution. In a preferred embodiment, the differences are not in one or more of the following domains: the PH domain, PLC-X domain, PLC-Y domain, the EF hand domain or the C2 domain. In another preferred embodiment one or more differences are in one or more of the following domains: the PH domain, PLC-X domain, PLC-Y domain, EF hand domain or the C2 domain.

Other embodiments include a protein that contain one or more changes in amino acid sequence, e.g., a change in an amino acid residue which is not essential for activity. Such 32544 proteins differ in amino acid sequence from SEQ ID NO:2, yet retain biological activity.

In one embodiment, a biologically active portion of a 32544 protein includes at least one or more of the following domains: the PH domain, PLC-X domain, PLC-Y domain, or the C2 domain. Moreover, other biologically active portions, in which other regions of the protein are deleted, can be prepared by recombinant techniques and evaluated for one or more of the functional activities of a native 32544 protein.

In a preferred embodiment, the 32544 protein has an amino acid sequence shown in SEQ ID NO:2. In other embodiments, the 32544 protein is substantially identical to SEQ ID NO:2. In yet another embodiment, the 32544 protein is substantially identical to SEQ ID NO:2 and retains the functional activity of the protein of SEQ ID NO:2, as described in detail above. Accordingly, in another embodiment, the 32544 protein is a protein which includes an amino acid sequence at least about 60%, 65%, 70%, 75%, 80%, 85%, 90%, 95%, 98% or more identical to SEQ ID NO:2.

32544 Chimeric or Fusion Proteins

In another aspect, the invention provides 32544 chimeric or fusion proteins. As used herein, a 32544 "chimeric protein" or "fusion protein" includes a 32544 polypeptide linked to a non-32544 polypeptide. A "non-32544 polypeptide" refers to a polypeptide having an amino acid sequence corresponding to a protein which is not substantially homologous to the 32544 protein, e.g., a protein which is different from the 32544 protein and which is derived from the same or a different organism. The 32544 polypeptide of the fusion protein can correspond to all or a portion e.g., a fragment described herein of a 32544 amino acid sequence. In a preferred embodiment, a 32544 fusion protein includes at least one (or two) biologically active portion of a 32544 protein. The non-32544 polypeptide can be fused to the N-terminus or C-terminus of the 32544 polypeptide.

The fusion protein can include a moiety which has a high affinity for a ligand. For example, the fusion protein can be a GST-32544 fusion protein in which the 32544 sequences are fused to the C-terminus of the GST sequences. Such fusion proteins can facilitate the purification of recombinant 32544. Alternatively, the fusion protein can be a 32544 protein containing a heterologous signal sequence at its N-terminus. In certain host cells (e.g., mammalian host cells), expression and/or secretion of 32544 can be increased through use of a heterologous signal sequence.

Fusion proteins can include all or a part of a serum protein, e.g., an IgG constant region, or human serum albumin.

The 32544 fusion proteins of the invention can be incorporated into pharmaceutical compositions and administered to a subject in vivo. The 32544 fusion proteins can be used to affect the bioavailability of a 32544 substrate. 32544 fusion proteins may be useful therapeutically for the treatment of disorders caused by, for example, (i) aberrant modification or mutation of a gene encoding a 32544 protein; (ii) mis-regulation of the 32544 gene; and (iii) aberrant post-translational modification of a 32544 protein.

Moreover, the 32544-fusion proteins of the invention can be used as immunogens to produce anti-32544 antibodies in a subject, to purify 32544 ligands and in screening assays to identify molecules which inhibit the interaction of 32544 with a 32544 substrate.

Expression vectors are commercially available that already encode a fusion moiety (e.g., a GST polypeptide). A 32544-encoding nucleic acid can be cloned into such an expression vector such that the fusion moiety is linked in-frame to the 32544 protein.

Variants of 32544 Proteins

In another aspect, the invention also features a variant of a 32544 polypeptide, e.g., which functions as an agonist (mimetics) or as an antagonist. Variants of the 32544 proteins can be generated by mutagenesis, e.g., discrete point mutation, the insertion or deletion of sequences or the truncation of a 32544 protein. An agonist of the 32544 proteins can retain substantially the same, or a subset, of the biological activities of the naturally occurring form of a 32544 protein. An antagonist of a 32544 protein can inhibit one or more of the activities of the naturally occurring form of the 32544 protein by, for example, competitively modulating a 32544-mediated activity of a 32544 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 32544 protein.

Variants of a 32544 protein can be identified by screening combinatorial libraries of mutants, e.g., truncation mutants, of a 32544 protein for agonist or antagonist activity.

Libraries of fragments e.g., N terminal, C terminal, or internal fragments, of a 32544 protein coding sequence can be used to generate a variegated population of fragments for screening and subsequent selection of variants of a 32544 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 32544 variants (Arkin and Yourvan, (1992) *Proc. Natl. Acad. Sci. USA* 89:7811–7815; Delgrave et al., (1993) *Protein Engineering* 6(3):327–331).

Cell based assays can be exploited to analyze a variegated 32544 library. For example, a library of expression vectors can be transfected into a cell line, e.g., a cell line, which ordinarily responds to 32544 in a substrate-dependent manner. The transfected cells are then contacted with 32544 and the effect of the expression of the mutant on signaling by the 32544 substrate can be detected, e.g., by measuring inositol 1,4,5-trisphosphate or diacylglycerol. Plasmid DNA can then be recovered from the cells which score for inhibition, or alternatively, potentiation of signaling by the 32544 substrate, and the individual clones further characterized.

In another aspect, the invention features a method of making a 32544 polypeptide, e.g., a peptide having a non-wild type activity, e.g., an antagonist, agonist, or super agonist of a naturally occurring 32544 polypeptide, e.g., a naturally occurring 32544 polypeptide. The method includes: altering the sequence of a 32544 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 32544 polypeptide a biological activity of a naturally occurring 32544 polypeptide. The method includes: altering the sequence, e.g., by substitution or deletion of one or more residues, of a 32544 polypeptide, e.g., altering the sequence of a non-conserved region, or a domain or residue described herein, and testing the altered polypeptide for the desired activity.

Anti-32544 Antibodies

In another aspect, the invention provides an anti-32544 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 32544 protein or, antigenic peptide fragment of 32544 can be used as an immunogen or can be used to identify anti-32544 antibodies made with other immunogens, e.g., cells, membrane preparations, and the like. The antigenic peptide of 32544 should include at least 8 amino acid residues of the amino acid sequence shown in SEQ ID NO:2 and encompasses an epitope of 32544. Preferably, the antigenic peptide includes at least 10 amino acid residues, more preferably at least 15 amino acid residues, even more preferably at least 20 amino acid residues, and most preferably at least 30 amino acid residues.

Fragments of 32544 which include, e.g., residues 960–980 of SEQ ID NO:2 can be, e.g., used as immunogens, or used to be hydrophilic regions of the 32544 protein. Similarly, a fragment of 32544 which includes, e.g., residues 1010–1025 of SEQ ID NO:2 can be used to make an antibody against what is believed to be a hydrophobic region of the 32544 protein; a fragment of 32544 which includes, e.g., residues 323–468 of SEQ ID NO:2 can be used to make an antibody against what is believed to be the phospholipase family region of the 32544 protein.

Antibodies reactive with, or specific for, any of these regions, or other regions or domains described herein are provided.

In a preferred embodiment the antibody fails to bind an Fc receptor, e.g. it is a type which does not support Fc receptor binding or has been modified, e.g., by deletion or other mutation, such that is does not have a functional Fc receptor binding region.

Preferred epitopes encompassed by the antigenic peptide are regions of 32544 are located on the surface of the protein, e.g., hydrophilic regions, as well as regions with high antigenicity. For example, an Emini surface probability analysis of the human 32544 protein sequence can be used to indicate the regions that have a particularly high probability of being localized to the surface of the 32544 protein and are thus likely to constitute surface residues useful for targeting antibody production.

In a preferred embodiment the antibody binds an epitope on any domain or region on 32544 proteins described herein.

Chimeric, humanized, but most preferably, completely human antibodies are desirable for applications which include repeated administration, e.g., therapeutic treatment (and some diagnostic applications) of human patients.

The anti-32544 antibody can be a single chain antibody. A single-chain antibody (scFV) may be engineered (see, for example, Colcher, D. et al., *Ann. NY Acad. Sci.* 1999 Jun 30;880:263–80; and Reiter, Y., *Clin. Cancer Res.* 1996 Feb;2(2):245–52). The single chain antibody can be dimerized or multimerized to generate multivalent antibodies having specificities for different epitopes of the same target 32544 protein.

An anti-32544 antibody (e.g., monoclonal antibody) can be used to isolate 32544 by standard techniques, such as affinity chromatography or immunoprecipitation. Moreover, an anti-32544 antibody can be used to detect 32544 protein (e.g., in a cellular lysate or cell supernatant) in order to evaluate the abundance and pattern of expression of the protein. Anti-32544 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavid/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 32544 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 32544 proteins, mutant forms of 32544 proteins, fusion proteins, and the like).

The recombinant expression vectors of the invention can be designed for expression of 32544 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S., (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 32544 activity assays, (e.g., direct assays or competitive assays described in detail below), or to generate antibodies specific for 32544 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six (6) weeks).

To maximize recombinant protein expression in *E. coli* is to express the protein in host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 32544 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al., (1987) *Genes Dev.* 1:268–277), lymphoid-specific promoters (Calame and Eaton, (1988) *Adv. Immunol.* 43:235–275), in particular promoters of T cell receptors (Winoto and Baltimore, (1989) *EMBO J.* 8:729–733) and immunoglobulins (Banerji et al., (1983) *Cell* 33:729–740; Queen and Baltimore, (1983) *Cell* 33:741–748), neuron-specific promoters (e.g., the neurofilament promoter; Byrne and Ruddle, (1989) *Proc. Natl. Acad. Sci. USA* 86:5473–5477), pancreas-specific promoters (Edlund et al., (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, (1990) Science 249:374–379) and the α-fetoprotein promoter (Campes and Tilghman, (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, *Reviews— Trends in Genetics*, Vol. 1(1) 1986.

Another aspect the invention provides a host cell which includes a nucleic acid molecule described herein, e.g., a 32544 nucleic acid molecule within a recombinant expression vector or a 32544 nucleic acid molecule containing sequences which allow it to homologously recombine into a specific site of the host cell's genome. The terms "host cell" and "recombinant host cell" are used interchangeably herein. Such terms refer not only to the particular subject cell but rather also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 32544 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 32544 protein. Accordingly, the invention further provides methods for producing a 32544 protein using the host cells of the invention. In one embodiment, the method includes culturing the host cell of the invention (into which a recombinant expression vector encoding a 32544 protein has been introduced) in a suitable medium such that a 32544 protein is produced. In another embodiment, the method further includes isolating a 32544 protein from the medium or the host cell.

In another aspect, the invention features, a cell or purified preparation of cells which include a 32544 transgene, or which otherwise misexpress 32544. The cell preparation can consist of human or non-human cells, e.g., rodent cells, e.g., mouse or rat cells, rabbit cells, or pig cells. In preferred embodiments, the cell or cells include a 32544 transgene, e.g., a heterologous form of a 32544, e.g., a gene derived from humans (in the case of a non-human cell). The 32544 transgene can be misexpressed, e.g., overexpressed or underexpressed. In other preferred embodiments, the cell or cells include a gene which misexpress an endogenous 32544, e.g., a gene the expression of which is disrupted, e.g., a knockout. Such cells can serve as a model for studying disorders which are related to mutated or misexpressed 32544 alleles or for use in drug screening.

In another aspect, the invention features, a human cell, e.g., a hematopoietic stem cell, transformed with nucleic acid which encodes a subject 32544 polypeptide.

Also provided are cells or a purified preparation thereof, e.g., human cells, in which an endogenous 32544 is under the control of a regulatory sequence that does not normally control the expression of the endogenous 32544 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 32544 gene. For example, an endogenous 32544 gene, e.g., a gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published on May 16, 1991.

Transgenic Animals

The invention provides non-human transgenic animals. Such animals are useful for studying the function and/or activity of a 32544 protein and for identifying and/or evaluating modulators of 32544 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 32544 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 32544 protein to particular cells. A transgenic founder animal can be identified based upon the presence of a 32544 transgene in its genome and/or expression of 32544 mRNA in tissues or cells of the animals. A transgenic founder animal can then be used to breed additional animals carrying the transgene. Moreover, transgenic animals carrying a transgene encoding a 32544 protein can further be bred to other transgenic animals carrying other transgenes. 32544 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 32544 protein (e.g., via a recombinant expression vector in a host cell in gene therapy applications), to detect a 32544 mRNA (e.g., in a biological sample) or a genetic alteration in a 32544 gene, and to modulate 32544 activity, as described further below. The 32544 proteins can be used to treat disorders characterized by insufficient or excessive production of a 32544 substrate or production of 32544 inhibitors. In addition, the 32544 proteins can be used to screen for naturally occurring 32544 substrates, to screen for drugs or compounds which modulate 32544 activity, as well as to treat disorders characterized by insufficient or excessive production of 32544 protein or production of 32544 protein forms which have decreased, aberrant or unwanted activity compared to 32544 wild-type protein. Such disorders include those characterized by aberrant signaling or aberrant, e.g., hyperproliferative, cell growth. Moreover, the anti-32544 antibodies of the invention can be used to detect and isolate 32544 proteins, regulate the bioavailability of 32544 proteins, and modulate 32544 activity.

A method of evaluating a compound for the ability to interact with, e.g., bind, a subject 32544 polypeptide is provided. The method includes: contacting the compound with the subject 32544 polypeptide; and evaluating ability of the compound to interact with, e.g., to bind or form a complex with the subject 32544 polypeptide. This method can be performed in vitro, e.g., in a cell free system, or in vivo, e.g., in a two-hybrid interaction trap assay. This method can be used to identify naturally occurring molecules which interact with subject 32544 polypeptide. It can also be used to find natural or synthetic inhibitors of subject 32544 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 32544 proteins, have a stimulatory or inhibitory effect on, for example, 32544 expression or 32544 activity, or have a stimulatory or inhibitory effect on, for example, the expression or activity of a 32544 substrate. Compounds thus identified can be used to modulate the activity of target gene products (e.g., 32544 genes) in a therapeutic protocol, to elaborate the biological function of the target gene product, or to identify compounds that disrupt normal target gene interactions.

In one embodiment, the invention provides assays for screening candidate or test compounds which are substrates of a 32544 protein or polypeptide or a biologically active portion thereof. In another embodiment, the invention provides assays for screening candidate or test compounds which bind to or modulate the activity of a 32544 protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al., *J. Med. Chem.* 1994, 37: 2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A*. 90:6909; Erb et al., (1994) *Proc. Natl. Acad. Sci. USA* 91:11422; Zuckermann et al., (1994). *J. Med. Chem.* 37:2678; Cho et al., (1993) *Science* 261:1303; Carrell et al., (1994) *Angew. Chem. Int. Ed. Engl.* 33:2059; Carell et al., (1994) *Angew. Chem. Int. Ed. Engl.* 33:2061; and in Gallop et al., (1994) *J. Med. Chem.* 37:1233.

Libraries of compounds may be presented in solution (e.g., Houghten, (1992) *Biotechniques* 13:412–421), or on beads (Lam, (1991) *Nature* 354:82–84), chips (Fodor, (1993) *Nature* 364:555–556), bacteria or spores (Ladner, U.S. Pat. No. 5,223,409), plasmids (Cull et al., (1992) *Proc. Natl. Acad. Sci. USA* 89:1865–1869) or on phage (Scott and Smith, (1990) *Science* 249:386–390); (Devlin, (1990) *Science* 249:404–406); (Cwirla et al., (1990) *Proc. Natl. Acad. Sci.* 87:6378–6382); (Felici, (1991) *J. Mol. Biol.* 222:301–310); (Ladner supra.).

In one embodiment, an assay is a cell-based assay in which a cell which expresses a 32544 protein or biologically active portion thereof is contacted with a test compound, and the ability of the test compound to modulate 32544 activity is determined. Determining the ability of the test compound to modulate 32544 activity can be accomplished by monitoring, for example, phospholipase family activity. The cell, for example, can be of mammalian origin, e.g., human. Cell homogenates, or fractions, preferably membrane containing fractions, can also be tested.

The ability of the test compound to modulate 32544 binding to a compound, e.g., a 32544 substrate, or to bind to 32544 can also be evaluated. This can be accomplished, for example, by coupling the compound, e.g., the substrate, with a radioisotope or enzymatic label such that binding of the compound, e.g., the substrate, to 32544 can be determined by detecting the labeled compound, e.g., substrate, in a complex. Alternatively, 32544 could be coupled with a radioisotope or enzymatic label to monitor the ability of a test compound to modulate 32544 binding to a 32544 substrate in a complex. For example, compounds (e.g., 32544 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 32544 substrate) to interact with 32544 with or without the labeling of any of the interactants can be evaluated. For example, a microphysiometer can be used to detect the interaction of a compound with 32544 without the labeling of either the compound or the 32544. McConnell, H. M. et al., (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 32544.

In yet another embodiment, a cell-free assay is provided in which a 32544 protein or biologically active portion thereof is contacted with a test compound and the ability of the test compound to bind to the 32544 protein or biologically active portion thereof is evaluated. Preferred biologically active portions of the 32544 proteins to be used in assays of the present invention include fragments which participate in interactions with non-32544 molecules, e.g., fragments with high surface probability scores.

Soluble and/or membrane-bound forms of isolated proteins (e.g., 32544 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

In one embodiment, assays are performed where the ability of an agent to block phospholipase family activity within a cell is evaluated.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 32544 protein to bind to a target molecule can be accomplished using real-time Biomolecular Interaction Analysis (BIA) (see, e.g., Sjolander, S. and Urbaniczky, C., (1991) *Anal. Chem.* 63:2338–2345 and Szabo et al., (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 32544, an anti-32544 antibody or its target molecule to facilitate separation of complexed from uncomplexed forms of one or both of the proteins, as well as to accommodate automation of the assay. Binding of a test compound to a 32544 protein, or interaction of a 32544 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/32544 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 32544 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 32544 binding or activity determined using standard techniques.

Other techniques for immobilizing either a 32544 protein or a target molecule on matrices include using conjugation of biotin and streptavidin. Biotinylated 32544 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 32544 protein or target molecules but which do not interfere with binding of the 32544 protein to its target molecule. Such antibodies can be derivatized to the wells of the plate, and unbound target or 32544 protein trapped in the wells by antibody conjugation. Methods for detecting such complexes, in addition to those described above for the GST-immobilized complexes, include immunodetection of complexes using antibodies reactive with the 32544 protein or target molecule, as well as enzyme-linked assays which rely on detecting an enzymatic activity associated with the 32544 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochein Sci* 1993 Aug;18(8):284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N.H., *J. Mol. Recognit.* 1998 Winter; 11(1–6):141–8; Hage, D. S., and Tweed, S.A., *J. Chromatogr. B Biomed. Sci. Appl.* 1997 Oct. 10;699 (1–2) :499–525). Further, fluorescence energy transfer may also be conveniently utilized, as described herein, to detect binding without further purification of the complex from solution.

In a preferred embodiment, the assay includes contacting the 32544 protein or biologically active portion thereof with a known compound which binds 32544 to form an assay mixture, contacting the assay mixture with a test compound, and determining the ability of the test compound to interact with a 32544 protein, wherein determining the ability of the test compound to interact with a 32544 protein includes determining the ability of the test compound to preferentially bind to 32544 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 32544 genes herein identified. In an alternative embodiment, the invention provides methods for determining the ability of the test compound to modulate the activity of a 32544 protein through modulation of the activity of a downstream effector of a 32544 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immnobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 32544 proteins can be used as "bait proteins" in a two-hybrid assay or three-hybrid assay (see, e.g., U.S. Pat. No. 5,283,317; Zervos et al., (1993) *Cell* 72:223–232; Madura et al., (1993) *J. Biol. Chem.* 268:12046–12054; Bartel et al., (1993) *Biotechniques* 14:920–924; Iwabuchi et al., (1993) *Oncogene* 8:1693–1696; and Brent WO94/10300), to identify other proteins, which bind to or interact with 32544 ("32544-binding proteins" or "32544-bp") and are involved in 32544 activity. Such 32544-bps can be activators or inhibitors of signals by the 32544 proteins or 32544 targets as, for example, downstream elements of a 32544-mediated signaling pathway.

The two-hybrid system is based on the modular nature of most transcription factors, which consist of separable DNA-binding and activation domains. Briefly, the assay utilizes two different DNA constructs. In one construct, the gene that codes for a 32544 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 32544 protein can be the fused to the activator domain.) If the "bait" and the "prey" proteins are able to interact, in vivo, forming a 32544-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 32544 protein.

In another embodiment, modulators of 32544 expression are identified. For example, a cell or cell free mixture is contacted with a candidate compound and the expression of 32544 mRNA or protein evaluated relative to the level of expression of 32544 mRNA or protein in the absence of the candidate compound. When expression of 32544 mRNA or protein is greater in the presence of the candidate compound than in its absence, the candidate compound is identified as a stimulator of 32544 mRNA or protein expression. Alternatively, when expression of 32544 mRNA or protein is less (statistically significantly less) in the presence of the candidate compound than in its absence, the candidate compound is identified as an inhibitor of 32544 mRNA or protein expression. The level of 32544 mRNA or protein expression can be determined by methods described herein for detecting 32544 mRNA or protein.

In another aspect, the invention pertains to a combination of two or more of the assays described herein. For example, a modulating agent can be identified using a cell-based or a cell free assay, and the ability of the agent to modulate the activity of a 32544 protein can be confirmed in vivo, e.g., in an animal.

This invention further pertains to novel agents identified by the above-described screening assays. Accordingly, it is within the scope of this invention to further use an agent identified as described herein (e.g., a 32544 modulating agent, an antisense 32544 nucleic acid molecule, a 32544-specific antibody, or a 32544-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 32544 with a disease; (ii) identify an individual from a minute biological sample (tissue typing); and (iii) aid in forensic identification of a biological sample. These applications are described in the subsections below.

Chromosome Mapping

The 32544 nucleotide sequences or portions thereof can be used to map the location of the 32544 genes on a chromosome. This process is called chromosome mapping. Chromosome mapping is useful in correlating the 32544 sequences with genes associated with disease.

Briefly, 32544 genes can be mapped to chromosomes by preparing PCR primers (preferably 15–25 bp in length) from the 32544 nucleotide sequences. These primers can then be used for PCR screening of somatic cell hybrids containing individual human chromosomes. Only those hybrids containing the human gene corresponding to the 32544 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al., (1983) Science 220:919–924).

Other mapping strategies e.g., in situ hybridization (described in Fan, Y. et al., (1990) Proc. Natl. Acad. Sci. USA, 87:6223–27), pre-screening with labeled flow-sorted chromosomes, and pre-selection by hybridization to chromosome specific cDNA libraries can be used to map 32544 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al., (1987) Nature, 325:783–787.

Moreover, differences in the DNA sequences between individuals affected and unaffected with a disease associated with the 32544 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 32544 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 32544 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 32544 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 32544 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The 32544 nucleotide sequences described herein can further be used to provide polynucleotide reagents, e.g., labeled or labelable probes which can be used in, for example, an in situ hybridization technique, to identify a specific tissue, e.g., a tissue containing phospholipase family activity. This can be very useful in cases where a forensic pathologist is presented with a tissue of unknown origin. Panels of such 32544 probes can be used to identify tissue by species and/or by organ type.

In a similar fashion, these reagents, e.g., 32544 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 32544.

Such disorders include, e.g., a disorder associated with the misexpression of 32544, or lipid metabolism related disorder.

The method includes one or more of the following:
detecting, in a tissue of the subject, the presence or absence of a mutation which affects the expression of the 32544 gene, or detecting the presence or absence of a mutation in a region which controls the expression of the gene, e.g., a mutation in the 5' control region;
detecting, in a tissue of the subject, the presence or absence of a mutation which alters the structure of the 32544 gene;
detecting, in a tissue of the subject, the misexpression of the 32544 gene, at the mRNA level, e.g., detecting a non-wild type level of a mRNA;
detecting, in a tissue of the subject, the misexpression of the gene, at the protein level, e.g., detecting a non-wild type level of a 32544 polypeptide.

In preferred embodiments the method includes: ascertaining the existence of at least one of: a deletion of one or more nucleotides from the 32544 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1 naturally occurring mutants thereof or 5' or 3' flanking sequences naturally associated with the 32544 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 32544 gene; the presence of a non-wild type splicing pattern of a messenger RNA transcript of the gene; or a non-wild type level of 32544.

Methods of the invention can be used prenatally or to determine if a subject's offspring will be at risk for a disorder.

In preferred embodiments the method includes determining the structure of a 32544 gene, an abnormal structure being indicative of risk for the disorder.

In preferred embodiments the method includes contacting a sample form the subject with an antibody to the 32544 protein or a nucleic acid, which hybridizes specifically with the gene. These and other embodiments are discussed below.

Diagnostic and Prognostic Assays

The presence, level, or absence of 32544 protein or nucleic acid in a biological sample can be evaluated by obtaining a biological sample from a test subject and contacting the biological sample with a compound or an agent capable of detecting 32544 protein or nucleic acid (e.g., mRNA, genomic DNA) that encodes 32544 protein such that the presence of 32544 protein or nucleic acid is detected in the biological sample. The term "biological sample" includes tissues, cells and biological fluids isolated from a subject, as well as tissues, cells and fluids present within a subject. A preferred biological sample is serum. The level of expression of the 32544 gene can be measured in a number of ways, including, but not limited to: measuring the mRNA encoded by the 32544 genes; measuring the amount of protein encoded by the 32544 genes; or measuring the activity of the protein encoded by the 32544 genes.

The level of mRNA corresponding to the 32544 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 32544 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to 32544 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 32544 genes.

The level of mRNA in a sample that is encoded by one of 32544 can be evaluated with nucleic acid amplification, e.g., by rtPCR (Mullis, 1987, U.S. Pat. No. 4,683,202), ligase chain reaction (Barany, 1991, *Proc. Natl. Acad. Sci. USA* 88:189–193), self sustained sequence replication (Guatelli et al., 1990, *Proc. Natl. Acad. Sci. USA* 87:1874–1878), transcriptional amplification system (Kwoh et al., 1989, *Proc. Natl Acad. Sci. USA* 86:1173–1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 32544 gene being analyzed.

In another embodiment, the methods further contacting a control sample with a compound or agent capable of detecting 32544 mRNA, or genomic DNA, and comparing the presence of 32544 mRNA or genomic DNA in the control sample with the presence of 32544 mRNA or genomic DNA in the test sample.

A variety of methods can be used to determine the level of protein encoded by 32544. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 32544 protein in a biological sample in vitro as well as in vivo. In vitro techniques for detection of 32544 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 32544 protein include introducing into a subject a labeled anti-32544 antibody. For example, the antibody can be labeled with a radioactive marker whose presence and location in a subject can be detected by standard imaging techniques.

In another embodiment, the methods further include contacting the control sample with a compound or agent capable of detecting 32544 protein, and comparing the presence of 32544 protein in the control sample with the presence of 32544 protein in the test sample.

The invention also includes kits for detecting the presence of 32544 in a biological sample. For example, the kit can include a compound or agent capable of detecting 32544 protein or mRNA in a biological sample; and a standard. The compound or agent can be packaged in a suitable container. The kit can further comprise instructions for using the kit to detect 32544 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 32544 expression or activity. As used herein, the term "unwanted" includes an unwanted phenomenon involved in a biological response such as pain or deregulated cell proliferation.

In one embodiment, a disease or disorder associated with aberrant or unwanted 32544 expression or activity is identified. A test sample is obtained from a subject and 32544 protein or nucleic acid (e.g., mRNA or genomic DNA) is evaluated, wherein the level, e.g., the presence or absence, of 32544 protein or nucleic acid is diagnostic for a subject having or at risk of developing a disease or disorder associated with aberrant or unwanted 32544 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 32544 expression or activity. For example, such methods can be used to determine whether a subject can be effectively treated with an agent for a cellular growth related disorder.

The methods of the invention can also be used to detect genetic alterations in a 32544 gene, thereby determining if a subject with the altered gene is at risk for a disorder characterized by misregulation in 32544 protein activity or nucleic acid expression, such as a cellular growth related disorder. In preferred embodiments, the methods include detecting, in a sample from the subject, the presence or absence of a genetic alteration characterized by at least one of an alteration affecting the integrity of a gene encoding a 32544-protein, or the mis-expression of the 32544 gene. For example, such genetic alterations can be detected by ascertaining the existence of at least one of 1) a deletion of one or more nucleotides from a 32544 gene; 2) an addition of one or more nucleotides to a 32544 gene; 3) a substitution of one or more nucleotides of a 32544 gene, 4) a chromosomal rearrangement of a 32544 gene; 5) an alteration in the level of a messenger RNA transcript of a 32544 gene, 6) aberrant modification of a 32544 gene, such as of the methylation pattern of the genomic DNA, 7) the presence of a non-wild type splicing pattern of a messenger RNA transcript of a 32544 gene, 8) a non-wild type level of a 32544-protein, 9) allelic loss of a 32544 gene, and 10) inappropriate post-translational modification of a 32544-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 32544-gene. This method can include the steps of collecting a sample of cells from a subject, isolating nucleic acid (e.g., genomic, mRNA or both) from the sample, contacting the nucleic acid sample with one or more primers which specifically hybridize to a 32544 gene under conditions such that hybridization and amplification of the 32544-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al., (1988) *Bio-Technology* 6:1197), or other nucleic acid amplification methods, followed by the detection of the amplified molecules using techniques known to those of skill in the art.

In another embodiment, mutations in a 32544 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 32544 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al., (1996) *Human Mutation* 7: 244–255; Kozal, M. J. et al., (1996) *Nature Medicine* 2:753–759). For example, genetic mutations in 32544 can be identified in two dimensional arrays containing light-generated DNA probes as described in Cronin, M. T. et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 32544 gene and detect mutations by comparing the sequence of the sample 32544 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 32544 gene include methods in which protection from cleavage agents is used to detect mismatched bases in RNA/RNA or RNA/DNA heteroduplexes (Myers et al., (1985) *Science* 230:1242; Cotton et al., (1988) *Proc. Natl. Acad. Sci. USA* 85:4397; Saleeba et al., (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 32544 cDNAs obtained from samples of cells. For example, the mutY enzyme of *E. coli* cleaves A at G/A mismatches and the thymidine DNA glycosylase from HeLa cells cleaves T at G/T mismatches (Hsu et al., (1994) *Carcinogenesis* 15:1657–1662; U.S. Pat. No. 5,459,039).

In other embodiments, alterations in electrophoretic mobility will be used to identify mutations in 32544 genes.

For example, single strand conformation polymorphism (SSCP) may be used to detect differences in electrophoretic mobility between mutant and wild type nucleic acids (Orita et al., (1989) *Proc. Natl. Acad. Sci. USA*: 86:2766, see also Cotton, (1993) *Mutat. Res.* 285:125–144; and Hayashi, (1992) *Genet. Anal. Tech. Appl* 9:73–79). Single-stranded DNA fragments of sample and control 32544 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., (1991) *Trends Genet*. 7:5).

In yet another embodiment, the movement of mutant or wild-type fragments in polyacrylamide gels containing a gradient of denaturant is assayed using denaturing gradient gel electrophoresis (DGGE) (Myers et al., (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner, (1987) *Biophys. Chem.* 265:12753).

Examples of other techniques for detecting point mutations include, but are not limited to, selective oligonucleotide hybridization, selective amplification, or selective primer extension (Saiki et al., (1986) *Nature* 324:163); Saiki et al., (1989) *Proc. Natl. Acad. Sci. USA* 86:6230).

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al., (1989) *Nucleic Acids Res.* 17:2437–2448) or at the extreme 3' end of one primer where, under appropriate conditions, mismatch can prevent, or reduce polymerase extension (Prossner, (1993) *Tibtech* 11:238). In addition it may be desirable to introduce a novel restriction site in the region of the mutation to create cleavage-based detection (Gasparini et al., (1992) *Mol. Cell Probes* 6:1). It is anticipated that in certain embodiments amplification may also be performed using Taq ligase for amplification (Barany, (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 32544 gene.

Use of 32544 Molecules as Surrogate Markers

The 32544 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 32544 molecules of the invention may be detected, and may be correlated with one or more biological states in vivo. For example, the 32544 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 32544 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 32544 marker) transcription or expression, the amplified marker may be in a quantity which is more readily detectable than the drug itself. Also, the marker may be more easily detected due to the nature of the marker itself; for example, using the methods described herein, anti-32544 antibodies may be employed in an immune-based detection system for a 32544 protein marker, or 32544-specific radiolabeled probes may be used to detect a 32544 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect*. 90: 229–238; Schentag (1999) *Am. J Health-Syst. Pharm.* 56 Suppl. 3: S21–S24; and Nicolau (1999) *Am, J. Health-Syst. Pharm.* 56 Suppl. 3: S16–S20.

The 32544 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 32544 protein or RNA) for specific tumor markers in a subject, a drug or course of treatment may be selected that is optimized for the treatment of the specific tumor likely to be present in the subject. Similarly, the presence or absence of a specific sequence mutation in 32544 DNA may correlate 32544 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-32544 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polytheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al., ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980. The nucleic acid molecules of the invention can be inserted into vectors and used as gene therapy vectors. Gene therapy vectors can be delivered to a subject by, for example, intravenous injection, local administration (see U.S. Pat. 5,328,470) or by stereotactic injection (see e.g., Chen et al., (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 32544 expression or activity. "Treatment", as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 32544 molecules of the present invention or 32544 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 32544 expression or activity, by administering to the subject a 32544 or an agent which modulates 32544 expression or at least one 32544 activity. Subjects at risk for a disease which is caused or contributed to by aberrant or unwanted 32544 expression or activity can be identified by, for example, any or a combination of diagnostic or prognostic assays as described herein. Administration of a prophylactic agent can occur prior to the manifestation of symptoms characteristic of the 32544 aberrance, such that a disease or disorder is prevented or, alternatively, delayed in its progression. Depending on the type of 32544 aberrance, for example, a 32544, 32544 agonist or 32544 antagonist agent can be used for treating the subject. The appropriate agent can be determined based on screening assays described herein.

It is possible that some 32544 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 32544 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 32544 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 32544 expression is through the use of aptamer molecules specific for 32544 protein. Aptamers are nucleic acid molecules having a tertiary structure which permits them to specifically bind to protein ligands (see, e.g., Osborne, et al., Curr. Opin. Chem. Biol. 1997, 1(1): 5–9; and Patel, D. J., Curr. Opin. Chem. Biol. 1997 Jun;1(1):32–46). Since nucleic acid molecules may in many cases be more conveniently introduced into target cells than therapeutic protein molecules may be, aptamers offer a method by which 32544 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 32544 disorders. For a description of antibodies, see the Antibody section above.

In circumstances wherein injection of an animal or a human subject with a 32544 protein or epitope for stimulating antibody production is harmful to the subject, it is possible to generate an immune response against 32544 through the use of anti-idiotypic antibodies (see, for example, Herlyn, D., Ann. Med. 1999;31(1):66–78; and Bhattacharya-Chatterjee, M., and Foon, K. A., Cancer Treat. Res. 1998;94:51–68). If an anti-idiotypic antibody is introduced into a mammal or human subject, it should stimulate the production of anti-anti-idiotypic antibodies, which should be specific to the 32544 protein. Vaccines directed to a disease characterized by 32544 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al., (1993, Proc. Natl. Acad. Sci. USA 90:7889–7893).

The identified compounds that inhibit target gene expression, synthesis and/or activity can be administered to a patient at therapeutically effective doses to prevent, treat or ameliorate 32544 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 32544 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al., (1996) *Current Opinion in Biotechnology* 7:89–94 and in Shea, K. J., (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al., (1993) *Nature* 361:645–647. Through the use of isotope-labeling, the "free" concentration of compound which modulates the expression or activity of 32544 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al., (1995) *Analytical Chemistry* 67:2142–2144.

Another aspect of the invention pertains to methods of modulating 32544 expression or activity for therapeutic purposes. Accordingly, in an exemplary embodiment, the modulatory method of the invention involves contacting a cell with a 32544 or agent that modulates one or more of the activities of 32544 protein activity associated with the cell. An agent that modulates 32544 protein activity can be an agent as described herein, such as a nucleic acid or a protein, a naturally-occurring target molecule of a 32544 protein (e.g., a 32544 substrate or receptor), a 32544 antibody, a 32544 agonist or antagonist, a peptidomimetic of a 32544 agonist or antagonist, or other small molecule.

In one embodiment, the agent stimulates one or 32544 activities. Examples of such stimulatory agents include active 32544 protein and a nucleic acid molecule encoding 32544. In another embodiment, the agent inhibits one or more 32544 activities. Examples of such inhibitory agents include antisense 32544 nucleic acid molecules, anti-32544 antibodies, and 32544 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 32544 protein or nucleic acid molecule. In one embodiment, the method involves administering an agent (e.g., an agent identified by a screening assay described herein), or combination of agents that modulates (e.g., upregulates or downregulates) 32544 expression or activity. In another embodiment, the method involves administering a 32544 protein or nucleic acid molecule as therapy to compensate for reduced, aberrant, or unwanted 32544 expression or activity.

Stimulation of 32544 activity is desirable in situations in which 32544 is abnormally downregulated and/or in which increased 32544 activity is likely to have a beneficial effect. For example, stimulation of 32544 activity is desirable in situations in which a 32544 is downregulated and/or in which increased 32544 activity is likely to have a beneficial effect. Likewise, inhibition of 32544 activity is desirable in situations in which 32544 is abnormally upregulated and/or in which decreased 32544 activity is likely to have a beneficial effect.

The 32544 molecules can act as novel diagnostic targets and therapeutic agents for controlling one or more of cellular proliferative and/or differentiative disorders, cardiovascular disorders, immune disorders, brain disorders, and pain disorders or metabolic disorders as described above, as well as disorders associated with bone metabolism, hematopoietic disorders, liver disorders, or viral diseases.

Aberrant expression and/or activity of 32544 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 32544 molecules effects in bone cells, e.g. osteoclasts and osteoblasts, that may in turn result in bone formation and degeneration. For example, 32544 molecules may support different activities of bone resorbing osteoclasts such as the stimulation of differentiation of monocytes and mononuclear phagocytes into osteoclasts. Accordingly, 32544 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Examples of hematopoietic disorders include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolsim, for example, fibrosis resulting from a storage disorder such as Gaucher's disease (lipid abnormalities) or a glycogen storage disease, Al -antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 32544 molecules may play an important role in the etiology of certain viral diseases, including but not limited to, Hepatitis B, Hepatitis C and Herpes Simplex Virus (HSV). Modulators of 32544 activity could be used to control viral diseases. The modulators can be used in the treatment and/or diagnosis of viral infected tissue or virus-associated tissue fibrosis, especially liver and liver fibrosis. Also, 32544 modulators can be used in the treatment and/or diagnosis of virus-associated carcinoma, especially hepatocellular cancer.

Pharmacogenomics

The 32544 molecules of the present invention, as well as agents, or modulators which have a stimulatory or inhibitory effect on 32544 activity (e.g., 32544 gene expression) as identified by a screening assay described herein can be administered to individuals to treat (prophylactically or therapeutically) 32544 associated disorders (e.g., cellular growth related disorders) associated with aberrant or unwanted 32544 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 32544 molecule or 32544 modulator as well as tailoring the dosage and/or therapeutic regimen of treatment with a 32544 molecule or 32544 modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11) :983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 32544 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 32544 molecule or 32544 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 32544 molecule or 32544 modulator, such as a modulator identified by one of the exemplary screening assays described herein.

The present invention further provides methods for identifying new agents, or combinations, that are based on identifying agents that modulate the activity of one or more of the gene products encoded by one or more of the 32544 genes of the present invention, wherein these products may be associated with resistance of the cells to a therapeutic agent. Specifically, the activity of the proteins encoded by the 32544 genes of the present invention can be used as a basis for identifying agents for overcoming agent resistance. By blocking the activity of one or more of the resistance proteins, target cells, e.g., cancer cells, will become sensitive to treatment with an agent that the unmodified target cells were resistant to.

Monitoring the influence of agents (e.g., drugs) on the expression or activity of a 32544 protein can be applied in clinical trials. For example, the effectiveness of an agent determined by a screening assay as described herein to increase 32544 gene expression, protein levels, or upregulate 32544 activity, can be monitored in clinical trials of subjects exhibiting decreased 32544 gene expression, protein levels, or downregulated 32544 activity. Alternatively, the effectiveness of an agent determined by a screening assay to decrease 32544 gene expression, protein levels, or downregulate 32544 activity, can be monitored in clinical trials of subjects exhibiting increased 32544 gene expression, protein levels, or upregulated 32544 activity. In such clinical trials, the expression or activity of a 32544 gene, and preferably, other genes that have been implicated in, for example, a 32544-associated disorder can be used as a "read out" or markers of the phenotype of a particular cell.
Other Embodiments In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 32544, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 32544 nucleic acid, polypeptide, or antibody.

The capture probes can be a set of nucleic acids from a selected sample, e.g., a sample of nucleic acids derived from a control or non-stimulated tissue or cell.

The method can include contacting the 32544 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 32544. Such methods can be used to diagnose a subject, e.g., to evaluate risk for a disease or disorder, to evaluate suitability of a selected treatment for a subject, to evaluate whether a subject has a disease or disorder. 32544 is associated with phospholipase family activity, thus it is useful for disorders associated with abnormal lipid metabolism.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or mis express 32544 or from a cell or subject in which a 32544 mediated response has been elicited, e.g., by contact of the cell with 32544 nucleic acid or protein, or administration to the cell or subject 32544 nucleic acid or protein; contacting the array with one or more inquiry probe, wherein an inquiry probe can be a nucleic acid, polypeptide, or antibody (which is preferably other than 32544 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 32544 (or does not express as highly as in the case of the 32544 positive plurality of capture probes) or from a cell or subject which in which a 32544 mediated response has not been elicited (or has been elicited to a lesser extent than in the first sample); contacting the array with one or more inquiry probes (which is preferably other than a 32544 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 32544, e.g., analyzing structure, function, or relatedness to other nucleic acid or amino acid sequences. The method includes: providing a 32544 nucleic acid or amino acid sequence; comparing the 32544 sequence with one or more preferably a plurality of sequences from a collection of sequences, e.g., a nucleic acid or protein sequence database; to thereby analyze 32544.

Preferred databases include GenBank™. The method can include evaluating the sequence identity between a 32544 sequence and a database sequence. The method can be performed by accessing the database at a second site, e.g., over the internet.

In another aspect, the invention features, a set of oligonucleotides, useful, e.g., for identifying SNP's, or identifying specific alleles of 32544. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with different labels, such that an oligonucleotides which hybridizes to one allele provides a signal that is distinguishable from an oligonucleotides which hybridizes to a second allele.

This invention is further illustrated by the following examples which should not be construed as limiting. The contents of all references, patents and published patent applications cited throughout this application are incorporated herein by reference.

EXAMPLES

Example 1
Identification and Characterization of Human 32544 cDNA

The human 32544 sequence (FIG. 1; SEQ ID NO:1), which is approximately 4635 nucleotides long including untranslated regions, contains a predicted methionine-initiated coding sequence of about 3621 nucleotides (nucleotides 435 to 4055 of SEQ ID NO:1; SEQ ID NO:3). The coding sequence encodes a 1207 amino acid protein (SEQ ID NO:2).

Example 2
Tissue Distribution of 32544 mRNA

Northern blot hybridizations with various RNA samples can be performed under standard conditions and washed under stringent conditions, i.e., 0.2×SSC at 65° C. A DNA probe corresponding to all or a portion of the 32544 cDNA (SEQ ID NO:1) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 3
Gene Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Human 32544 expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human 32544 gene. Each human 32544 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100nM probe for β-2 microglobulin and 600 nM forward and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 32544 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 32544 gene is normalized by subtracting the Ct value of the β-2 microglobulin gene to obtain a ΔCt value using the following formula:

$$\Delta Ct = Ct_{human\ 59914\ and\ 59921} - Ct_{\beta\text{-}2\ microglobulin}.$$

Expression is then calibrated against a cDNA sample showing a comparatively low level of expression of the human 32544 gene. The ΔCt value for the calibrator sample is then subtracted from ΔCt for each tissue sample according to the following formula:

$$\Delta\Delta Ct = \Delta Ct_{sample} - \Delta Ct_{calibrator}.$$

Relative expression is then calculated using the arithmetic formula given by 2-ΔΔCt. Expression of the target human 32544 gene in each of the tissues tested is then graphically represented as discussed in more detail below.

TaqMan real-time quantitative RT-PCR was used to detect the presence of RNA transcript corresponding to human 32544 relative to a no template control in a panel of human tissues or cells.

Taqman in Pain human panel phase I shows the highest levels of expression in brain followed by spinal cord and skin as shown in Table 1.

TABLE 1

Phase 1.3.3 Expression of 32544 w/β2

| Tissue Type | Mean | β 2 Mean | ∂∂ Ct | Expression |
|---|---|---|---|---|
| Artery normal | 40 | 21.64 | 18.36 | 0 |
| Vein normal | 40 | 20.5 | 19.5 | 0 |
| Aortic SMC EARLY | 38.01 | 22.2 | 15.81 | 0 |
| Coronary SMC | 35.63 | 22.34 | 13.29 | 0 |
| Static HUVEC | 32.74 | 20.54 | 12.21 | 0.2111 |
| Shear HUVEC | 30.81 | 20.8 | 10.01 | 0.9698 |
| Heart normal | 31.85 | 18.59 | 13.26 | 0.1023 |
| Heart CHF | 32.4 | 18.99 | 13.4 | 0.0922 |
| Kidney | 29.62 | 20.52 | 9.11 | 1.816 |

TABLE 1-continued

Phase 1.3.3 Expression of 32544 w/β2

| Tissue Type | Mean | β 2 Mean | ∂∂ Ct | Expression |
|---|---|---|---|---|
| Skeletal Muscle | 37.45 | 21.58 | 15.88 | 0 |
| Adipose normal | 37.2 | 19.82 | 17.38 | 0 |
| Pancreas | 32.05 | 21.75 | 10.3 | 0.7932 |
| primary osteoblasts | 32.79 | 18.95 | 13.85 | 0.068 |
| Osteoclasts (diff) | 34.15 | 17.5 | 16.64 | 0.0098 |
| Skin normal | 28.11 | 21.22 | 6.89 | 8.4315 |
| Spinal cord normal | 26.61 | 20.09 | 6.51 | 10.9343 |
| Brain Cortex normal | 25.2 | 21.34 | 3.86 | 69.1082 |
| Brain Hypothalamus normal | 26.95 | 21.68 | 5.27 | 25.9162 |
| Nerve | 35.86 | 23.53 | 12.33 | 0 |
| DRG (Dorsal Root Ganglion) | 31.93 | 21.82 | 10.11 | 0.908 |
| Glial Cells (Astrocytes) | 33 | 22.48 | 10.52 | 0.6834 |
| Glioblastoma | 27.9 | 18.22 | 9.68 | 1.2191 |
| Breast normal | 30.43 | 21.04 | 9.39 | 1.4853 |
| Breast tumor | 27.82 | 18.72 | 9.1 | 1.8223 |
| Ovary normal | 32.47 | 20.2 | 12.27 | 0.2032 |
| Ovary Tumor | 33.69 | 21.48 | 12.21 | 0.2118 |
| Prostate Normal | 27.92 | 20.09 | 7.83 | 4.41 |
| Prostate Tumor | 26.64 | 18.15 | 8.49 | 2.7813 |
| Epithelial Cells (Prostate) | 25.16 | 21.37 | 3.79 | 72.544 |
| Colon normal | 29.86 | 18.44 | 11.41 | 0.3662 |
| Colon Tumor | 29.11 | 18.75 | 10.36 | 0.7635 |
| Lung normal | 31.66 | 18.36 | 13.3 | 0.0992 |
| Lung tumor | 25.68 | 18.57 | 7.12 | 7.189 |
| Lung COPD | 30.35 | 19.09 | 11.26 | 0.4092 |
| Colon IBD | 31.69 | 18.66 | 13.04 | 0.1191 |
| Liver normal | 31.84 | 20.32 | 11.53 | 0.3382 |
| Liver fibrosis | 32.08 | 21.57 | 10.51 | 0.6858 |
| Dermal Cells- fibroblasts | 33.99 | 20.45 | 13.54 | 0.084 |
| Spleen normal | 28.81 | 19.6 | 9.21 | 1.6885 |
| Tonsil normal | 25.63 | 17.43 | 8.19 | 3.4242 |
| Lymph node | 27.29 | 18.74 | 8.54 | 2.6773 |
| Small Intestine | 30.25 | 19.73 | 10.52 | 0.681 |
| Skin-Decubitus | 29.14 | 20.52 | 8.62 | 2.5417 |
| Synovium | 31.92 | 20.16 | 11.77 | 0.2873 |
| BM-MNC (Bone marrow mononuclear cells) | 26.13 | 16.98 | 9.15 | 1.7603 |
| Activated PBMC | 29.23 | 16.22 | 13.02 | 0.1208 |

TABLE 2

Human Panel Phase I (Pain)

| Tissue Type | 32544 | β2.803 | ∂Ct | Expression |
|---|---|---|---|---|
| Adrenal Gland | 29.91 | 18.78 | 11.14 | 0.44 |
| Brain | 24.65 | 20.35 | 4.30 | 50.77 |
| Heart | 37.29 | 18.67 | 18.62 | 0.00 |
| Kidney | 28.78 | 18.68 | 10.10 | 0.91 |
| Liver | 30.86 | 19.12 | 11.74 | 0.29 |
| Lung | 30.90 | 16.68 | 14.22 | 0.05 |
| Mammary Gland | 28.45 | 18.34 | 10.11 | 0.90 |
| Pancreas | 31.06 | 21.66 | 9.40 | 1.49 |
| Placenta | 35.88 | 18.68 | 17.20 | 0.01 |
| Prostate | 26.57 | 18.13 | 8.44 | 2.88 |
| Salivary Gland | 27.37 | 18.68 | 8.70 | 2.41 |
| Muscle | 32.42 | 21.00 | 11.42 | 0.36 |
| Sm. Intestine | 29.76 | 19.11 | 10.66 | 0.62 |
| Spleen | 28.46 | 16.57 | 11.90 | 0.26 |
| Stomach | 30.91 | 18.63 | 12.28 | 0.20 |
| Teste | 27.58 | 20.20 | 7.38 | 6.02 |
| Thymus | 26.63 | 18.11 | 8.52 | 2.72 |
| Trachea | 27.11 | 18.68 | 8.43 | 2.90 |
| Uterus | 30.85 | 18.70 | 12.15 | 0.22 |
| Spinal Cord | 25.65 | 19.21 | 6.44 | 11.52 |
| DRG | 33.43 | 19.26 | 14.17 | 0.05 |
| Skin | 25.85 | 18.90 | 6.96 | 8.06 |

Taqman experiments with the rat probe showed similar pattern of expression in the Phase I panel than the human probe. This rat Phase I panel also showed high levels of expression of 32544 in the sympathetic neurons of the superior cervical ganglia.

TABLE 3

Rat Panel Phase I

| Tissue | r32544 | 18S | ∂Ct | Expression |
|---|---|---|---|---|
| Brain | 25.07 | 12.12 | 12.96 | 0.13 |
| Spinal Cord | 29.68 | 12.74 | 16.95 | 0.01 |
| DRG | 32.10 | 12.37 | 19.73 | 0.00 |
| SCG | 26.18 | 13.21 | 12.97 | 0.12 |
| Optic Nerve | 28.44 | 11.66 | 16.78 | 0.01 |
| Hairy Skin | 28.39 | 13.40 | 14.99 | 0.03 |
| Gastro Muscle | 29.87 | 12.07 | 17.80 | 0.00 |
| Heart | 35.78 | 12.92 | 22.86 | 0.00 |
| Kidney | 35.65 | 13.59 | 22.06 | 0.00 |
| Liver | 39.15 | 12.83 | 26.32 | 0.00 |
| Lung | 32.41 | 13.35 | 19.06 | 0.00 |
| Spleen | 34.22 | 12.68 | 21.54 | 0.00 |
| Aorta | 32.66 | 12.69 | 19.98 | 0.00 |
| Adrenal Gland | 32.73 | 12.21 | 20.52 | 0.00 |
| Salivary Gland | 32.09 | 12.28 | 19.81 | 0.00 |
| Thyroid | 27.45 | 12.14 | 15.31 | 0.02 |
| Prostate | 32.75 | 12.23 | 20.52 | 0.00 |
| Thymus | 31.06 | 12.30 | 18.77 | 0.00 |
| Trachea | 28.79 | 13.18 | 15.61 | 0.02 |
| Esophagus | 27.26 | 12.02 | 15.24 | 0.03 |
| Duodenum | 29.89 | 13.49 | 16.40 | 0.01 |
| Diaphragm | 36.36 | 13.31 | 23.06 | 0.00 |
| Colon | 28.43 | 13.87 | 14.56 | 0.04 |

Rat Panel Phase II (Table 4) showed no regulation of 32544 in the DRG after CFA treatment. However, 32544 is up-regulated about six fold in DRG after CCI and about 10 folds in axotomized DRG.

TABLE 4

Rat Panel Phase II

| Tissue | r32544 | 18S | ∂Ct | Expression |
|---|---|---|---|---|
| Naïve DRG | 32.18 | 11.44 | 20.74 | 0.001 |
| I DRG CCI 3 | 29.00 | 11.50 | 17.50 | 0.005 |
| I DRG CCI 7 | 28.80 | 11.18 | 17.62 | 0.005 |
| I DRG CCI 10 | 29.16 | 11.09 | 18.07 | 0.004 |
| I DRG CCI 14 | 31.93 | 13.19 | 18.75 | 0.002 |
| I DRG CCI 28 | 29.87 | 11.26 | 18.61 | 0.002 |
| Naïve DRG | 32.03 | 11.50 | 20.53 | 0.001 |
| I DRG CFA 1 | 32.53 | 11.24 | 21.30 | 0.000 |
| I DRG CFA 3 | 32.60 | 11.37 | 21.24 | 0.000 |
| I DRG CFA 7 | 32.50 | 11.37 | 21.13 | 0.000 |
| I DRG CFA 10 | 32.45 | 11.31 | 21.14 | 0.000 |
| I DRG CFA 14 | 32.21 | 11.33 | 20.88 | 0.001 |
| I DRG CFA 28 | 32.41 | 11.34 | 21.08 | 0.000 |
| Naïve DRG | 32.35 | 11.42 | 20.93 | 0.001 |
| I DRG AXT 1 | 30.26 | 11.01 | 19.25 | 0.002 |
| I DRG AXT 3 | 28.42 | 11.61 | 16.82 | 0.009 |
| I DRG AXT 7 | 27.96 | 11.44 | 16.52 | 0.011 |
| I DRG AXT 14 | 27.53 | 11.36 | 16.18 | 0.014 |

TABLE 5

Rat Panel Phase III

| Tissue | r32544 | 18S | ∂Ct | Expression |
|---|---|---|---|---|
| Naïve SC | 25.13 | 11.76 | 13.37 | 0.09 |
| I SC CCI 3 | 23.63 | 11.13 | 12.50 | 0.17 |
| I SC CCI 7 | 24.35 | 12.08 | 12.27 | 0.20 |
| I SC CCI 10 | 24.28 | 12.47 | 11.81 | 0.28 |
| I SC CCI 14 | 24.25 | 11.53 | 12.72 | 0.15 |
| I SC CCI 28 | 24.83 | 12.13 | 12.70 | 0.15 |

TABLE 5-continued

Rat Panel Phase III

| Tissue | r32544 | 18S | ∂Ct | Expression |
|---|---|---|---|---|
| Naïve SC | 25.27 | 11.83 | 13.44 | 0.09 |
| I SC CFA 3 | 24.73 | 11.63 | 13.10 | 0.11 |
| I SC CFA 7 | 24.66 | 11.63 | 13.03 | 0.12 |
| I SC CFA 10 | 24.61 | 11.37 | 13.24 | 0.10 |
| I SC CFA 14 | 24.84 | 12.28 | 12.56 | 0.17 |
| I SC CFA 28 | 24.08 | 12.14 | 11.95 | 0.25 |
| Naïve SC | 25.33 | 11.81 | 13.52 | 0.09 |
| I SC AXT 1 | 24.64 | 11.99 | 12.65 | 0.16 |
| I SC AXT 3 | 24.86 | 11.71 | 13.15 | 0.11 |
| I SC AXT 7 | 24.88 | 11.59 | 13.29 | 0.10 |
| I SC AXT 14 | 23.75 | 12.63 | 11.12 | 0.45 |

Example 4
In situ Hybridization of 33544

Human ISH hybridization probe e+f shows expression of the 33544 gene in human brain, DRG and spinal cord. Human ISH probes do not cross-react with rat tissues. Probe e+f cross-react with monkey tissues, however, it shows higher background compared to the human tissues. In the spinal cord 33544 is expressed in the dorsal horn and in the DRG only in a small subpopulation of neurons.

Example 5
Recombinant Expression of 32544 in Bacterial Cells

In this example, 32544 is expressed as a recombinant glutathione-S-transferase (GST) fusion polypeptide in *E. coli* and the fusion polypeptide is isolated and characterized. Specifically, 32544 is fused to GST and this fusion polypeptide is expressed in *E. coli*, e.g., strain PEB199. Expression of the GST-25934 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 6
Expression of Recombinant 32544 Protein in COS Cells

To express the 32544 gene in COS cells, the pCDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 32544 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 32544 DNA sequence is amplified by PCR using two primers. The 5' primer contains the restriction site of interest followed by approximately twenty nucleotides of the 32544 coding sequence starting from the initiation codon; the 3' end sequence contains complementary sequences to the other restriction site of interest, a translation stop codon, the HA tag or FLAG tag and the last 20 nucleotides of the 32544 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 32544 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 32544-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989. The expression of the 32544 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual,* Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 32544 coding sequence is cloned directly into the polylinker of the pCDNA/Amp vector using the appropriate restriction sites. The resulting plasmid is transfected into COS cells in the manner described above, and the expression of the 32544 polypeptide is detected by radiolabelling and immunoprecipitation using a 32544 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising the nucleotide sequence of SEQ ID NO:1 or a nucleotide sequence complementary to the nucleotide sequence of SEQ ID NO:1.

2. An isolated nucleic acid molecule comprising a nucleotide sequence encoding a polypeptide comprising the amino acid sequence of SEQ ID NO:2 or a nucleotide sequence complementary to a nucleotide sequence encoding a polypeptide comprising the amino acid sequence of SEQ ID NO:2.

3. An isolated nucleic acid molecule comprising a nucleotide sequence encoding a fusion polypeptide comprising the amino acid sequence of SEQ ID NO:2 and a heterologous polypeptide.

4. The isolated nucleic acid molecule of claim 1, further comprising vector nucleic acid sequences.

5. The isolated nucleic acid molecule of claim 2, further comprising vector nucleic acid sequences.

6. The isolated nucleic acid molecule of claim 3, further comprising vector nucleic acid sequences.

7. A host cell containing the nucleic acid molecule of claim 4.

8. A host cell containing the nucleic acid molecule of claim 5.

9. A host cell containing the nucleic acid molecule of claim 6.

10. The host cell of claim 7 which is a mammalian cell.

11. The host cell of claim 8 which is a mammalian cell.

12. The host cell of claim 9 which is a mammalian cell.

13. A method for producing a polypeptide comprising the amino acid sequence of SEQ ID NO:2, comprising culturing the host cell of claim 7 under conditions in which the nucleic acid molecule is expressed.

14. A method for producing a polypeptide qomprising the amino acid sequence of SEQ ID NO:2, comprising culturing the host claim 8 under conditions in which the nucleic acid molecule is expressed.

15. A method for producing a polypeptide comprising the amino acid sequence of SEQ ID NO:2, comprising culturing the host cell of claim 9 under conditions in which the nucleic acid molecule is expressed.

* * * * *

UNITED STATES PATENT AND TRADEMARK OFFICE
CERTIFICATE OF CORRECTION

PATENT NO. : 6,897,056 B2
DATED : May 24, 2005
INVENTOR(S) : Rachel E. Meyers et al.

It is certified that error appears in the above-identified patent and that said Letters Patent is hereby corrected as shown below:

<u>Column 102,</u>
Line 56, please change "qomprising" to -- comprising --.
Line 58, please change "the host claim 8" to -- the host cell of claim 8 --.

Signed and Sealed this

Ninth Day of August, 2005

JON W. DUDAS
*Director of the United States Patent and Trademark Office*